US012569689B2

(12) United States Patent
Galarneau et al.

(10) Patent No.: US 12,569,689 B2
(45) Date of Patent: *Mar. 10, 2026

(54) MEDICAL DEVICE AND METHOD FOR DETECTING ATRIOVENTRICULAR BLOCK

(71) Applicant: Medtronic, Inc., Minneapolis, MN (US)

(72) Inventors: Michelle M. Galarneau, Minneapolis, MN (US); Vincent P. Ganion, Blaine, MN (US); Saul E. Greenhut, Denver, CO (US); Yanina Grinberg, Plymouth, MN (US); Todd J. Sheldon, North Oaks, MN (US); Paul R. Solheim, Blaine, MN (US); Hyun J. Yoon, Vadnais Heights, MN (US)

(73) Assignee: Medtronic, Inc., Minneapolis, MN (US)

( * ) Notice: Subject to any disclaimer, the term of this patent is extended or adjusted under 35 U.S.C. 154(b) by 259 days.

This patent is subject to a terminal disclaimer.

(21) Appl. No.: 18/338,341

(22) Filed: Jun. 20, 2023

(65) Prior Publication Data

US 2023/0330420 A1 Oct. 19, 2023

Related U.S. Application Data

(63) Continuation of application No. 17/221,404, filed on Apr. 2, 2021, now Pat. No. 11,717,688.

(Continued)

(51) Int. Cl.
*A61N 1/365* (2006.01)
*A61N 1/02* (2006.01)
(Continued)

(52) U.S. Cl.
CPC ......... *A61N 1/36578* (2013.01); *A61N 1/025* (2013.01); *A61N 1/36507* (2013.01);
(Continued)

(58) Field of Classification Search
CPC ................ A61N 1/025; A61N 1/36507; A61N 1/36535; A61N 1/36542; A61N 1/36578; A61N 1/36585; A61N 1/37211
See application file for complete search history.

(56) References Cited

U.S. PATENT DOCUMENTS

| | | | |
|---|---|---|---|
| 4,485,813 A | 12/1984 | Anderson et al. |
| 5,052,388 A | 10/1991 | Sivula et al. |

(Continued)

FOREIGN PATENT DOCUMENTS

| | | |
|---|---|---|
| EP | 3260167 A1 | 12/2017 |
| WO | 2006086435 A2 | 8/2006 |
| WO | 2016171891 A1 | 10/2016 |

OTHER PUBLICATIONS

International Search Report and Written Opinion for International Application No. PCT/US2021/025846 mailed Jul. 12, 2021.

(Continued)

*Primary Examiner* — Brian T Gedeon

(57) ABSTRACT

A medical device includes a motion sensor configured to sense a motion signal. The medical device includes a control circuit configured to determine at least one ventricular event metric from the motion signal sensed over multiple of atrial cycles, determine that the ventricular event metric meets atrioventricular block criteria and generate an output in response to determining the atrioventricular block.

20 Claims, 18 Drawing Sheets

Related U.S. Application Data

(60) Provisional application No. 63/006,208, filed on Apr. 7, 2020.

(51) Int. Cl.

| | |
|---|---|
| *A61N 1/362* | (2006.01) |
| *A61N 1/372* | (2006.01) |
| *G16H 20/30* | (2018.01) |
| *G16H 40/67* | (2018.01) |

(52) U.S. Cl.
CPC ..... *A61N 1/36535* (2013.01); *A61N 1/36542* (2013.01); *A61N 1/36585* (2013.01); *A61N 1/37211* (2013.01); *G16H 20/30* (2018.01); *G16H 40/67* (2018.01)

(56) References Cited

U.S. PATENT DOCUMENTS

| | | | |
|---|---|---|---|
| 5,507,782 | A | 4/1996 | Kieval et al. |
| 5,593,431 | A | 1/1997 | Sheldon |
| 5,720,769 | A | 2/1998 | van Oort et al. |
| 5,885,471 | A | 3/1999 | Ruben et al. |
| 6,044,297 | A | 3/2000 | Sheldon et al. |
| 6,654,637 | B2 | 11/2003 | Rouw et al. |
| 8,055,339 | B2 | 11/2011 | Seim |
| 8,204,593 | B2 | 6/2012 | Sheldon et al. |
| 8,532,785 | B1 | 9/2013 | Crutchfield et al. |
| 8,731,662 | B2 | 5/2014 | Imran |
| 8,761,880 | B2 | 6/2014 | Maskara et al. |
| 8,788,028 | B2 | 7/2014 | Kumar et al. |
| 9,592,391 | B2 | 3/2017 | Stahmann et al. |
| 9,694,186 | B2 | 7/2017 | Carney et al. |
| 9,724,518 | B2 | 8/2017 | Sheldon et al. |
| 9,808,633 | B2 | 11/2017 | Bonner et al. |
| 10,207,116 | B2 | 2/2019 | Sheldon et al. |
| 10,463,866 | B2 | 11/2019 | Stahmann et al. |
| 11,504,536 | B2 | 11/2022 | Drake et al. |
| 2007/0179541 | A1 | 8/2007 | Prakash et al. |
| 2008/0234771 | A1 | 9/2008 | Chinchoy et al. |
| 2010/0318150 | A1 | 12/2010 | Graindorge |
| 2012/0095521 | A1 | 4/2012 | Hintz |
| 2012/0215274 | A1 | 8/2012 | Koh et al. |
| 2014/0121720 | A1 | 5/2014 | Bonner et al. |
| 2016/0015984 | A1 | 1/2016 | Demmer et al. |
| 2018/0085588 | A1 | 3/2018 | Splett et al. |
| 2018/0085589 | A1 | 3/2018 | Splett et al. |
| 2018/0117337 | A1 | 5/2018 | Demmer et al. |
| 2018/0161580 | A1 | 6/2018 | Demmer et al. |
| 2019/0029821 | A1 | 1/2019 | Nguyen et al. |
| 2019/0083779 | A1 | 3/2019 | Yang et al. |
| 2019/0321634 | A1 | 10/2019 | Sheldon et al. |

OTHER PUBLICATIONS

International Preliminary Report on Patentability for International Application No. PCT/US2021/025846 mailed Oct. 6, 2022.

350

352

SENSE FFRWs

354

FFRW SENSING LOST?     NO

YES

ENABLE MOTION SIGNAL SENSING     356

DETERMINE VENTRICULAR EVENT METRIC     358

360

NO     AV BLOCK CRITERIA MET?

YES

GENERATE OUTPUT     362

380

382 — ESTABLISH EVENT TEMPLATE(S)

IDENTIFY ATRIAL ELECTRICAL EVENT  384

SET SENSING WINDOW  386

DETERMINE MORPHOLOGY MATCH SCORE(S)  388

390 — V EVENT DETECTION CRITERIA MET?  YES

NO

DETECT AV BLOCK CYCLE  392

UPDATE AV BLOCK CYCLE COUNTER  394

396 — AV BLOCK CRITERIA MET?  NO

YES  398

GENERATE OUTPUT

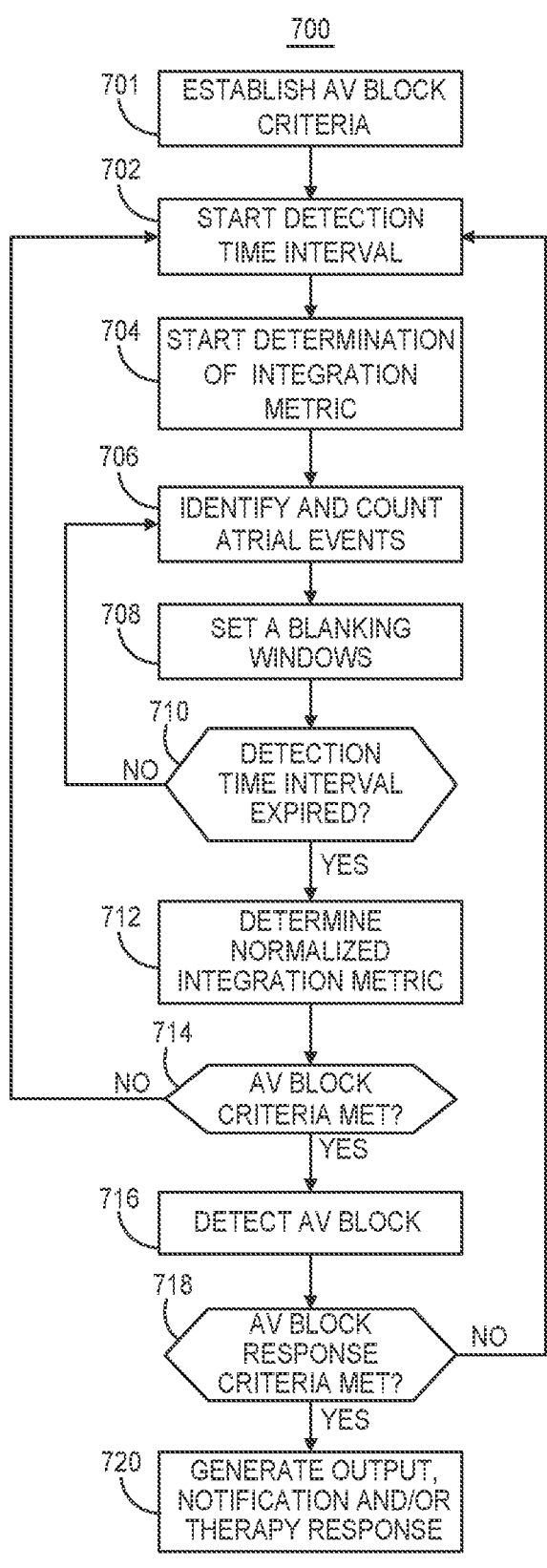

700

701 — ESTABLISH AV BLOCK CRITERIA

702 — START DETECTION TIME INTERVAL

704 — START DETERMINATION OF INTEGRATION METRIC

706 — IDENTIFY AND COUNT ATRIAL EVENTS

708 — SET A BLANKING WINDOWS

710 — DETECTION TIME INTERVAL EXPIRED?

NO

YES

712 — DETERMINE NORMALIZED INTEGRATION METRIC

714 — AV BLOCK CRITERIA MET?

NO

YES

716 — DETECT AV BLOCK

718 — AV BLOCK RESPONSE CRITERIA MET?

NO

YES

720 — GENERATE OUTPUT, NOTIFICATION AND/OR THERAPY RESPONSE

FIG. 15

MEDICAL DEVICE AND METHOD FOR DETECTING ATRIOVENTRICULAR BLOCK

REFERENCE TO RELATED APPLICATION

This application is a Continuation of U.S. patent application Ser. No. 17/221,404, filed Apr. 2, 2021, which claims the benefit of provisional U.S. Patent Application No. 63/006,208, filed Apr. 7, 2020, the entire content of both incorporated herein by reference.

TECHNICAL FIELD

This disclosure relates to a medical device and method for determining atrioventricular block.

BACKGROUND

During normal sinus rhythm (NSR), the heartbeat is regulated by electrical signals produced by the sino-atrial (SA) node located in the right atrial wall. Each atrial depolarization signal produced by the SA node spreads across the atria, causing the depolarization and contraction of the atria, and arrives at the atrioventricular (AV) node. The AV node responds by propagating a ventricular depolarization signal through the bundle of His of the ventricular septum and thereafter to the bundle branches and the Purkinje muscle fibers of the right and left ventricles, sometimes referred to as the "His-Purkinje system."

Patients with a conduction system abnormality, e.g., SA node dysfunction or poor AV node conduction, bundle branch block, or other conduction abnormalities, may receive a pacemaker to restore a more normal heart rhythm. A single chamber pacemaker coupled to a transvenous lead carrying electrodes positioned in the right atrium may provide atrial pacing to treat a patient having SA node dysfunction. When the AV node is functioning normally, single chamber atrial pacing may sufficiently correct the heart rhythm. The pacing-evoked atrial depolarizations may be conducted normally to the ventricles via the AV node and the His-Purkinje system maintaining normal AV synchrony. Some patients, however, may experience conduction abnormalities of the AV node, e.g., partial or complete AV block. AV block may be intermittent and may evolve over time. In the presence of high-grade AV block, atrial depolarizations are not conducted to the ventricles on every atrial cycle. A dual chamber pacemaker may be implanted in some patients to pace both the atrial and ventricular chambers and maintain AV synchrony. The dual chamber pacemaker may be coupled to a transvenous atrial lead and a transvenous ventricular lead, for placing electrodes for sensing and pacing in both the atrial and ventricular chambers. The pacemaker itself is generally implanted in a subcutaneous pocket with the transvenous leads tunneled to the subcutaneous pocket. Intracardiac pacemakers have been introduced or proposed for implantation entirely within a patient's heart eliminating the need for transvenous leads. For example, a ventricular intracardiac pacemaker may provide sensing and pacing from within a ventricular chamber of a patient having AV block to provide ventricular rate support.

SUMMARY

The techniques of this disclosure generally relate to a medical device having a motion sensor for sensing a motion signal that includes ventricular event signals corresponding to ventricular contraction (and/or relaxation) following a ventricular depolarization. The medical device may be configured to determine one or more features or metrics from the motion signal for determining when AV block may be present. The medical device may be a pacemaker configured to deliver atrial pacing and may determine when AV block associated with less than one ventricular event signal occurring with each atrial cycle may be present. In some examples, the medical device is an atrial intracardiac pacemaker or a pacemaker coupled to a transvenous atrial lead such that the motion sensor is positioned in an atrial chamber for sensing an intra-atrial motion signal. A medical device operating according to the techniques disclosed herein determines when AV block may be present based on a motion signal sensed from an atrial location in some examples.

In one example, the disclosure provides a medical device including a motion sensor configured to sense a motion signal and a control circuit coupled to the motion sensor for receiving the motion signal. The control circuit may be configured to determine at least one ventricular event metric from the motion signal sensed over multiple atrial cycles and determine if one or more ventricular event metrics meet AV block criteria. The control circuit generates an output in response to determining that the AV block criteria are met by the ventricular event metric(s). The output may be stored in a memory of the medical device and subsequently used to transmit data, adjust cardiac signal sensing and/or adjust a therapy in various examples.

In another example, the disclosure provides a method including sensing a motion signal, determining at least one ventricular event metric from the motion signal sensed over multiple atrial cycles, and determining that one or more ventricular event metrics meet AV block criteria. The method further includes generating an output in response to determining the AV block criteria are met by the ventricular event metric(s). The method may further include storing the output in a memory and subsequently use the stored output to transmit data, adjust cardiac signal sensing and/or adjust a therapy in various examples.

In another example, the disclosure provides a non-transitory, computer-readable storage medium comprising a set of instructions which, when executed by a control circuit of a medical device, cause the medical device to sense a motion signal, determine at least one ventricular event metric from the motion signal sensed over multiple atrial cycles, and determine that one or more ventricular event metrics meet AV block criteria. The instructions further cause the medical device to generate an output in response to the AV block criteria being met by the ventricular event metric(s). The instructions may cause the device to store the output in memory of the medical device and subsequently use the output to transmit data, adjust cardiac signal sensing and/or adjust a therapy in various examples.

Further disclosed herein is the subject matter of the following clauses:

1. A medical device comprising:
   a motion sensor configured to sense a motion signal;
   a control circuit configured to:
      determine at least one ventricular event metric from the motion signal sensed over a plurality of atrial cycles;
      determine that the at least one ventricular event metric meets atrioventricular block criteria; and
      generate an output in response to determining that the ventricular event metric meets the atrioventricular block criteria; and
   a memory configured to store the generated output.

2. The medical device of clause 1, wherein the control circuit is configured to determine the at least one ventricular event metric by determining an integration metric based on sample point amplitudes of the motion signal during at least a portion of each atrial cycle of the plurality of atrial cycles.

3. The medical device of clause 2, wherein the control circuit is configured to determine the integration metric by one of:
   determining a summation of amplitudes of sample points of the motion signal sensed over the plurality of atrial cycles; and
   determining a count of sample points of the motion signal sensed over the plurality of atrial cycles that are greater than a threshold amplitude.

4. The medical device of any of clauses 2-3, further comprising:
   a sensing circuit configured to sense a cardiac electrical signal and sense P-waves from the cardiac electrical signal; and
   a pulse generator configured to generate atrial pacing pulses;
   wherein the control circuit is configured to:
      determine a count of the plurality of atrial cycles based on at least one of the P-waves sensed by the sensing circuit and the atrial pacing pulses generated by the pulse generator; and
      determine the ventricular event metric by dividing the integration metric by the count of the plurality of atrial cycles.

5. The medical device of any of clauses 2-4, wherein the control circuit is further configured to:
   establish a ventricular event threshold by:
      determining the integration metric for each of a plurality of integration intervals; and
      setting the ventricular event threshold based on the determined integration metrics;
   wherein determining that the at least one ventricular event metric meets the atrioventricular block criteria comprises determining that at least one integration metric determined from the motion signal sensed over the plurality of atrial cycles is less than the ventricular event threshold.

6. The medical device of any of clauses 1-5, wherein the control circuit is configured to:
   determine at least one of a time of day, an atrial rate, a patient physical activity level, and a patient posture;
   set a detection time interval based on at least one of the time of day, the atrial rate, the patient physical activity level, and the patient posture, where the motion signal is sensed over the plurality of atrial cycles occurring during the detection time interval.

7. The medical device of any of clauses 1-6, wherein the control circuit is configured to:
   determine at least one feature of the motion signal during each atrial cycle of the plurality of cycles;
   determine each atrial cycle of the plurality of atrial cycles as one of an atrioventricular block cycle or an atrioventricular conduction cycle based on the at least one feature of the motion signal;
   determine the ventricular event metric by determining a count of the atrioventricular block cycles; and
   determine that the ventricular event metric meets atrioventricular block criteria in response to the count of atrioventricular block cycles being greater than a threshold value.

8. The medical device of clause 7, wherein the control circuit is configured to determine each atrial cycle of the plurality atrial cycles as one of an atrioventricular block cycle or an atrioventricular conduction cycle by:
   setting a sensing window during a portion of the atrial cycle;
   determining the atrial cycle as an atrioventricular block cycle in response to the motion signal not meeting ventricular event criteria during the sensing window; and
   determining the atrial cycle as an atrioventricular conduction cycle in response to the motion signal meeting the ventricular event criteria during the sensing window.

9. The medical device of any of clauses 7-8, wherein the control circuit is configured to determine each atrial cycle of the plurality of atrial cycles as one of an atrioventricular block cycle or an atrioventricular conduction cycle by:
   determining the atrial cycle as an atrioventricular block cycle in response to determining that the motion signal crosses a ventricular event sensing threshold amplitude less than a threshold number of times during the atrial cycle; and
   determining the atrial cycle as an atrioventricular conduction cycle in response to determining that the motion signal crosses the ventricular event sensing threshold amplitude at least the threshold number of times during the atrial cycle.

10. The medical device of any of clauses 1-9, wherein the control circuit is configured to:
   establish a ventricular event morphology template from the motion signal;
   determine a morphology match score between the ventricular event morphology template and the motion signal sensed during a portion of each atrial cycle of the plurality of atrial cycles; and
   determine the ventricular event metric based on the determined morphology match scores.

11. The medical device of any of clauses 1-10, further comprising:
   a sensing circuit configured to sense a cardiac electrical signal;
   wherein the control circuit is further configured to:
      detect an altered morphology of an atrial P-wave sensed by the sensing circuit; and
      determine the atrioventricular block criteria are met in response to detecting the altered P-wave morphology.

12. The medical device of any of clauses 1-11, wherein the control circuit is configured to determine the at least one ventricular event metric by determining from the motion signal at least one of: a maximum peak amplitude, a maximum slope, a signal area, a signal width, a count of sample points greater than a threshold amplitude, a number of threshold crossings, or a number of peaks.

13. The medical device of any of clauses 1-12, wherein the control circuit is configured to determine the at least one ventricular event metric from the motion signal by:
   determining a fiducial point of the motion signal during each atrial cycle of the plurality of atrial cycles;
   for each atrial cycle of the plurality of atrial cycles, determining an atrioventricular activation time from an atrial event to the fiducial point of the motion signal; and determining the ventricular event metric based on the atrioventricular activation times determined over the plurality of atrial cycles.

14. The medical device of clause 13, wherein the control circuit is further configured to:

determine the ventricular event metric by determining an increasing trend of the atrioventricular activation time and at least one previously determined atrioventricular activation time; and determine that the ventricular event metric meets the atrioventricular block criteria in response to determining the increasing trend of the atrioventricular activation time.

15. The medical device of any of clauses 1-14, wherein the control circuit is further configured to:

set an atrial blanking window during each atrial cycle of the plurality of atrial cycles; and determine the ventricular event metric from the motion signal sensed outside the atrial blanking windows.

16. The medical device of any of clauses 1-15, further comprising:

a sensing circuit configured to sense a cardiac electrical signal and sense far-field R-waves from the cardiac electrical signal;

wherein the control circuit is configured to:

determine a loss of far-field R-wave sensing by the sensing circuit; and determine the ventricular event metric from the motion signal over the plurality of atrial cycles in response to determining the loss of far-field R-wave sensing.

17. The medical device of any of clauses 1-16, further comprising a sensing circuit configured to:

sense a cardiac electrical signal; and enable sensing of far-field R-waves from the cardiac electrical signal in response to the control circuit generating the output.

18. The medical device of any of clauses 1-17, further comprising a pulse generator configured to adjust a pacing therapy in response to the control circuit generating the output.

19. The medical device of any of clauses 1-18, further comprising:

a sensing circuit configured to sense a cardiac electrical signal;

a memory; and a telemetry circuit;

wherein the control circuit is configured to generate the output by storing an episode of at least one of the cardiac electrical signal and the motion signal in response to determining the atrioventricular block criteria are met; and the telemetry circuit is configured to transmit the stored episode.

20. The medical device of any of clauses 1-19, wherein the control circuit is configured to:

detect a condition for monitoring for atrioventricular block; and determine the at least one ventricular event metric from the motion signal in response to detecting the condition for monitoring for atrioventricular block.

21. The medical device of clause 20, wherein the control circuit is further configured to set the atrioventricular block criteria based on the detected condition for monitoring for atrioventricular block.

22. The medical device of any of clauses 1-21, wherein the control circuit is further configured to:

determine that the motion signal meets termination criteria after determining that the at least one ventricular event metric meets the atrioventricular block criteria; and determining a duration of atrioventricular block in response to the termination criteria being met.

23. The medical device of any of clauses 1-22, further comprising a sensing circuit configured to sense a cardiac electrical signal, and wherein:

the control circuit is configured to:

determine the at least one ventricular event metric by determining an integration metric from the motion signal over each one of a plurality of integration intervals;

determine that a first one of the determined integration metrics is less than or equal to an atrioventricular block threshold;

start storing a cardiac signal episode in the memory by storing at least one of the motion signal and the cardiac electrical signal in response to determining that the first one of the determined integration metrics is less than or equal to the atrioventricular block threshold;

determine that the at least one ventricular event metric meets the atrioventricular block criteria by:

determining a representative value of the integration metrics determined over each one of the plurality of integration intervals; and determining that the representative value is less than or equal to the atrioventricular block threshold; and generate the output by storing the cardiac signal episode extending through at least a portion of the plurality of integration intervals as an atrioventricular block episode in the memory.

24. A method, comprising:

sensing a motion signal;

determining at least one ventricular event metric from the motion signal sensed over a plurality of atrial cycles;

determining that the at least one ventricular event metric meets atrioventricular block criteria;

generating an output in response to determining the atrioventricular block criteria are met; and storing the generated output.

25. The method of clause 24, wherein determining the at least one ventricular event metric comprises determining an integration metric based on sample point amplitudes of the motion signal during at least a portion of each atrial cycle of the plurality of atrial cycles.

26. The method of clause 25, wherein determine the integration metric comprises one of: determining a summation of amplitudes of sample points of the motion signal sensed over the plurality of atrial cycles; and determining a count of sample points of the motion signal sensed over the plurality of atrial cycles that are greater than a threshold amplitude.

27. The method of any of clauses 25-26, further comprising:

sensing a cardiac electrical signal;

sensing P-waves from the cardiac electrical signal;

generating atrial pacing pulses;

determining a count of the plurality of atrial cycles based on at least one of the sensed P-waves and the atrial pacing pulses; and determining the ventricular event metric by dividing the integration metric by the count of the plurality of atrial cycles.

28. The method of any of clauses 25-27, further comprising:
    establishing a ventricular event threshold by:
        determining the integration metric for each of a plurality of integration intervals; and
        setting the ventricular event threshold based on the determined integration metrics;
    wherein determining that the at least one ventricular event metric meets the atrioventricular block criteria comprises determining that at least one integration metric determined from the motion signal sensed over the plurality of atrial cycles is less than the ventricular event threshold.

29. The method of any of clauses 24-28, further comprising:
    determining at least one of a time of day, an atrial rate, a patient physical activity level, and a patient posture;
    setting a detection time interval based on at least one of the time of day, the atrial rate, the patient physical activity level, and the patient posture, where the motion signal is sensed over the plurality of atrial cycles occurring during the detection time interval.

30. The method of any of clauses 24-29, further comprising:
    determining at least one feature of the motion signal during each atrial cycle of the plurality of cycles;
    determining each atrial cycle of the plurality of atrial cycles as one of an atrioventricular block cycle or an atrioventricular conduction cycle based on the at least one feature of the motion signal;
    determining the ventricular event metric by determining a count of the atrioventricular block cycles; and
    determining that the ventricular event metric meets atrioventricular block criteria in response to the count of atrioventricular block cycles being greater than a threshold value.

31. The method of clause 30, wherein determining each atrial cycle of the plurality of atrial cycles as one of an atrioventricular block cycle or an atrioventricular conduction cycle comprises:
    setting a sensing window during the atrial cycle;
    determining the atrial cycle as an atrioventricular block cycle in response to the motion signal not meeting ventricular event criteria during the sensing window; and
    determining the atrial cycle as an atrioventricular conduction cycle in response to the motion signal meeting the ventricular event criteria during the sensing window.

32. The method of any of clauses 30-31, wherein determining each atrial cycle of the plurality of atrial cycles as one of an atrioventricular block cycle or an atrioventricular conduction cycle comprises:
    determining the atrial cycle as an atrioventricular block cycle in response to determining that the motion signal crosses a ventricular event sensing threshold amplitude less than a threshold number of times during the atrial cycle; and
    determining the atrial cycle as an atrioventricular conduction cycle in response to determining that the motion signal crosses the ventricular event sensing threshold amplitude at least the threshold number of times during the atrial cycle.

33. The method of any of clauses 24-32, further comprising:
    establishing a ventricular event morphology template from the motion signal;
    determining a morphology match score between the ventricular event morphology template and the motion signal sensed during a portion of each atrial cycle of the plurality of atrial cycles; and
    determining the ventricular event metric based on the determined morphology match scores.

34. The method of any of clauses 24-33, further comprising:
    sensing a cardiac electrical signal;
    detecting an altered morphology of an atrial P-wave sensed from the cardiac electrical signal; and
    determining the atrioventricular block criteria are met in response to detecting the altered P-wave morphology.

35. The method of any of clauses 24-34, wherein determining the at least one ventricular event metric comprises determining from the motion signal at least one of: a maximum peak amplitude, a maximum slope, a signal area, a signal width, a count of sample points greater than a threshold amplitude, a number of threshold crossings, or a number of peaks.

36. The method of any of clauses 24-35, wherein determining the at least one ventricular event metric from the motion signal comprises:
    determining a fiducial point of the motion signal during each atrial cycle of the plurality of atrial cycles;
    for each atrial cycle of the plurality of atrial cycles, determining an atrioventricular activation time from an atrial event to the fiducial point of the motion signal; and
    determining the ventricular event metric based on the atrioventricular activation times determined over the plurality of atrial cycles.

37. The method of clause 36, further comprising:
    determining the ventricular event metric by determining an increasing trend of the atrioventricular activation time and at least one previously determined atrioventricular activation time;
    and
    determining that the ventricular event metric meets the atrioventricular block criteria in response to determining the increasing trend of the atrioventricular activation time.

38. The method of any of clauses 24-37, further comprising:
    setting an atrial blanking window during each atrial cycle of the plurality of atrial cycles; and
    determining the ventricular event metric from the motion signal sensed outside the atrial blanking windows.

39. The method of any of clauses 24-38, further comprising:
    sensing a cardiac electrical signal;
    sensing far-field R-waves from the cardiac electrical signal;
    determining a loss of far-field R-wave sensing from the cardiac electrical signal; and
    determining the ventricular event metric from the motion signal over the plurality of atrial cycles in response to determining the loss of far-field R-wave sensing.

40. The method of any of clauses 24-39, further comprising:

sensing a cardiac electrical signal; and enabling sensing of far-field R-waves from the cardiac electrical signal in response to the control circuit generating the output.

41. The method of any of clauses 24-40, further comprising adjusting a pacing therapy in response to generating the output.

42. The method of any of clauses 24-41, further comprising:

sensing a cardiac electrical signal;

generating the output by storing an episode of at least one of the cardiac electrical signal and the motion signal in response to determining the atrioventricular block criteria are met; and transmitting the stored episode.

43. The method of any of clauses 24-42, further comprising:

detecting a condition for monitoring for atrioventricular block; and determining the at least one ventricular event metric from the motion signal in response to detecting the condition for monitoring for atrioventricular block.

44. The method of clause 43, further comprising setting the atrioventricular block criteria based on the detected condition for monitoring for atrioventricular block.

45. The method of any of clauses 24-44, further comprising:

determining that the motion signal meets termination criteria after determining that the at least one ventricular event metric meets the atrioventricular block criteria; and determining a duration of atrioventricular block in response to the termination criteria being met.

46. The method of any of clauses 24-45, further comprising:

sensing a cardiac electrical signal;

determining the at least one ventricular event metric by determining an integration metric from the motion signal over each one of a plurality of integration intervals;

determining that a first one of the determined integration metrics is less than or equal to an atrioventricular block threshold;

starting storage of a cardiac signal episode in the memory by storing at least one of the motion signal and the cardiac electrical signal in response to determining that the first one of the determined integration metrics is less than or equal to the atrioventricular block threshold;

determining that the at least one ventricular event metric meets the atrioventricular block criteria by:

determining a representative value of the integration metrics determined over each one of the plurality of integration intervals; and determining that the representative value is less than or equal to the atrioventricular block threshold; and generating the output by storing the cardiac signal episode extending through at least a portion of the plurality of integration intervals as an atrioventricular block episode in the memory.

47. A non-transitory, computer-readable storage medium comprising a set of instructions which, when executed by a control circuit of a medical device, cause the medical device to:

sense a motion signal;

determine at least one ventricular event metric from the motion signal sensed over a plurality of atrial cycles;

determine that the at least one ventricular event metric meets atrioventricular block criteria;

generate an output in response to determining the atrioventricular block; and store the output in a memory of the medical device.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF DRAWINGS

FIG. 15 is a flow chart of a method performed by a medical device, e.g., such as a pacemaker, for detecting AV block according to another example.

DETAILED DESCRIPTION

Figure 1:
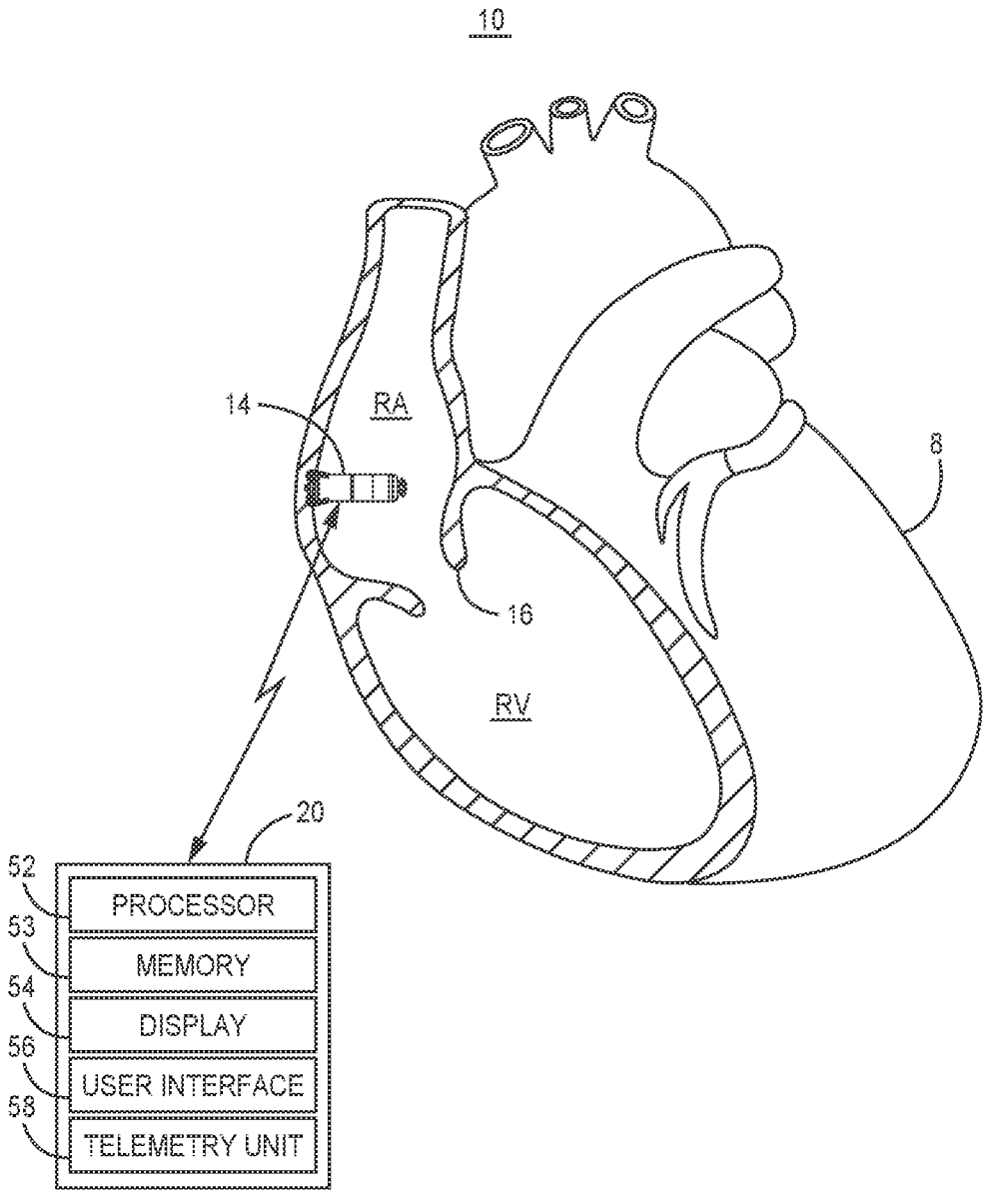
FIG. 1 is a conceptual diagram illustrating an implantable medical device (IMD) system that may be used to sense cardiac electrical signals and cardiac mechanical signals induced by cardiac motion and flowing blood and provide pacing therapy to a patient's heart.

In general, this disclosure describes techniques for determining when AV block criteria are met from a sensor signal that includes ventricular event signals corresponding to ventricular contraction. The sensor may be implanted in an atrial location, e.g., in or on an atrium, for sensing a signal correlated to mechanical heart activity. The sensor may be a motion sensor such as an accelerometer, a pressure sensor, a flow sensor or other sensor or combination thereof capable of generating a signal that includes ventricular event signals corresponding to the mechanical activation (contraction) of the ventricles. As described below, a motion signal, such as an accelerometer signal, may be produced by a motion sensor implanted in or on an atrial chamber. The motion signal may include cardiac event signals attendant to the mechanical contractions of the heart chambers. For example, ventricular mechanical event signals corresponding to ventricular contraction and/or closure of the atrioventricular valves caused by ventricular contraction may be present in a motion signal produced by a motion sensor implanted at a non-ventricular location, e.g., in or on an atrial chamber. A medical device operating according to the techniques disclosed herein may sense ventricular mechanical events, also referred to herein as "ventricular events," e.g., ventricular systolic events corresponding to ventricular contraction and/or ventricular diastolic events corresponding to ventricular relaxation and filling, from a motion sensor signal and detect AV conduction in response to sensing the ventricular mechanical events or detect AV block, or suspected AV block, when sensing of the ventricular mechanical events do not meet AV conduction criteria. AV block may be detected by the medical device when the motion signal meets AV block detection criteria over multiple atrial cycles.

As described below, a medical device including a motion sensor may be configured to determine a ventricular event metric from the motion sensor signal sensed over multiple atrial cycles and determine when one or more ventricular event metrics meet AV block criteria. As used herein, the term "ventricular event metric" refers to a value determined by the medical device from a sensor signal, e.g., a motion signal such as an acceleration signal sensed by an accelerometer, that is correlated to the strength (amplitude), frequency (or rate) and/or regularity (relative to atrial events) of the ventricular event signals in the sensor signal over multiple atrial cycles. The ventricular event metric may be determined as a count of sensed ventricular event signals over multiple atrial cycles, a ratio of sensed ventricular events to atrial events, an integration of the motion signal over multiple atrial cycles, an AV activation time, or variability of the AV activation time, as examples. Other examples of ventricular event metrics that may be determined from a sensor signal over multiple atrial cycles for determining when AV block criteria are met are described herein.

As used herein, the term "AV block criteria" refers to one or more thresholds or other criteria that may be applied to one or more ventricular event metrics or values derived from the ventricular event metrics to discriminate between episodes of relatively low ventricular motion and episodes of relatively higher ventricular motion. The episodes of relatively low ventricular motion, or more generally low cardiac motion, may correspond to episodes of AV block. Episodes of relatively higher cardiac motion as determined based on the ventricular event metric(s) may correspond to episodes of AV conduction. Various examples of AV block criteria are described below as they pertain to different types of ventricular event metrics that may be determined by the medical device.

In some examples, the medical device is an atrial pacemaker, which may be wholly implantable within an atrial heart chamber, having a motion sensor for producing an intra-atrial motion signal. Ventricular event signals may be sensed from within the atrium from the motion sensor signal for determining when AV block criteria are met, without requiring a sensor in or on the ventricles of the patient's heart for sensing ventricular events. Atrial P-waves, and in some examples far field ventricular R-waves, may be sensed using electrodes carried by the atrial pacemaker, and atrial pacing pulses can be delivered by the pacemaker implanted in the atrium. In some examples, the atrial pacemaker may be configured to pace the ventricular conduction system, e.g., the His-Purkinje system, from a location within the right atrium to provide ventricular pacing, which may track the atrial rate. In other examples, the atrial pacemaker may be implanted outside the heart and coupled to an epicardial or transvenous lead for positioning electrodes for sensing atrial P-waves and delivering atrial pacing pulses. The lead may carry a motion sensor for sensing a cardiac motion signal that may include ventricular event signals.

FIG. 1 is a conceptual diagram illustrating an implantable medical device (IMD) system 10 that may be used to sense cardiac electrical signals and cardiac mechanical signals induced by cardiac motion and flowing blood and provide pacing therapy to a patient's heart 8. IMD system 10 includes an atrial pacemaker 14. Pacemaker 14 may be a leadless, transcatheter intracardiac pacemaker which is adapted for implantation wholly within a heart chamber, e.g., wholly within the right atrium (RA) of heart 8 for sensing cardiac signals and delivering atrial pacing pulses. Pacemaker 14 may be reduced in size compared to subcutaneously implanted pacemakers and may be generally cylindrical in shape to enable transvenous implantation via a delivery catheter. Pacemaker 14 is shown positioned in the RA, e.g., along an endocardial wall though other locations are possible within or on the RA different than the location shown. The techniques disclosed herein are not limited to a particular intra-atrial pacemaker location.

Pacemaker 14 is capable of producing electrical stimulation pulses, e.g., pacing pulses, delivered to heart 8 via one or more electrodes on the outer housing of the pacemaker. Pacemaker 14 is configured to deliver RA pacing pulses and sense an RA cardiac electrical signal using housing based electrodes for producing an RA electrogram (EGM) signal. The cardiac electrical signals may be sensed using the housing based electrodes that are also used to deliver pacing pulses to the RA in some examples.

Pacemaker 14 may be a leadless pacemaker as shown, including housing-based electrodes for sensing the cardiac electrical signal and delivering pacing pulses. As described below, pacemaker 14 includes cardiac electrical signal sensing circuitry configured to sense atrial P-waves attendant to the depolarization of the atrial myocardium and a pulse generator for generating and delivering an atrial pacing pulse in the absence of a sensed atrial P-wave. In some examples, the cardiac electrical signal sensing circuitry of pacemaker 14 may be configured to sense far-field R-waves (FFRWs) associated with the depolarization of the ventricular myocardium using the housing based electrodes. For instance, an atrial pacing pulse may be triggered by sensing an FFRW. Examples of cardiac sensing and atrial pacing methods that may be performed by pacemaker 14 are generally disclosed in U.S. Pat. No. 9,808,633 (Bonner, et al.), incorporated herein by reference in its entirety. For example, an atrial pacing pulse may be triggered by a sensed FFRW for promoting synchrony between the atrial and ventricular heart chamber contractions.

According to the techniques described herein, ventricular events associated with ventricular contraction are detected by pacemaker 14 from a motion sensor signal such as an accelerometer signal, produced by a motion sensor that may be enclosed by the housing of pacemaker 14. The motion signal produced by an accelerometer implanted within an atrial chamber, which may be referred to as an "intra-atrial motion signal," may include motion signals caused by ventricular and atrial mechanical events. For example, acceleration of blood due to closure of the tricuspid valve 16 between the RA and RV, the mitral valve between the left atrium and the left ventricle and the heart motion due to ventricular contraction may produce a ventricular event signal. As described below, pacemaker 14 includes a control circuit with processing circuitry that is configured to determine when AV block criteria are met, e.g., due to the absence of ventricular event signals in 1:1 synchrony with atrial cycles and/or a prolonged delay in the ventricular event signal following atrial electrical events (sensed P-waves or atrial pacing pulses).

Pacemaker 14 may be configured to deliver atrial pacing therapy for treating a sinus node dysfunction. In some patients, the AV node may be functioning normally such that the pacing-evoked depolarizations caused by atrial pacing pulses are conducted to the ventricles by the normal conduction pathway, e.g., through the AV node and along the ventricular conduction system including the His bundle and the Purkinje fibers. The motion sensor, e.g., an accelerometer, included in pacemaker 14 produces a signal, e.g., an acceleration signal, that includes ventricular event signals corresponding to ventricular mechanical activation (contraction). In this way, pacemaker 14 may be enabled to detect and verify AV conduction. Pacemaker 14 may be configured to determine when AV block occurs or is likely to be present and may track a progression of AV block. The progression of AV block may be tracked by pacemaker 14 based on detecting an increase in the time between an atrial electrical event and the subsequent ventricular event and/or detecting an increasing frequency of atrial cycles in which the ventricular event does not follow the atrial electrical event at an expected conduction interval. As described below, pacemaker 14 may respond to determining that AV block criteria are met by generating an output, e.g., an AV block notification or alert and/or storing a segment of the motion sensor signal and/or atrial EGM signal.

Pacemaker 14 may be capable of bidirectional wireless communication with an external device 20 for programming the sensing and pacing control parameters, which may be utilized for detecting ventricular events and/or determining when AV block criteria are met from the motion sensor signal. Aspects of external device 20 may generally correspond to the external programming/monitoring unit disclosed in U.S. Pat. No. 5,507,782 (Kieval, et al.), hereby incorporated herein by reference in its entirety. External device 20 is often referred to as a "programmer" because it is typically used by a physician, technician, nurse, clinician or other qualified user for programming operating parameters in pacemaker 14. External device 20 may be located in a clinic, hospital or other medical facility. External device 20 may alternatively be embodied as a home monitor or a handheld device that may be used in a medical facility, in the patient's home, or another location. Operating parameters, including sensing and therapy delivery control parameters, may be programmed into pacemaker 14 by a user interacting with external device 20.

External device 20 may include a processor 52, memory 53, display unit 54, user interface 56 and telemetry unit 58. Processor 52 controls external device operations and processes data and signals received from pacemaker 14. Display unit 54 may generate a display, which may include a graphical user interface, of data and information relating to pacemaker functions to a user for reviewing pacemaker operation and programmed parameters as well as cardiac electrical signals, cardiac motion signals or other physiological data that may be acquired by pacemaker 14 and transmitted to external device 20 during an interrogation session. For example, pacemaker 14 may generate an output including an AV block detection notification and transmit the notification which may include data determined to support the AV block detection and may include an episode of the atrial EGM signal produced by pacemaker sensing circuitry and/or an episode of the motion signal produced by the motion sensor included in pacemaker 14 when AV block criteria are met by the motion signal. Notification of the AV block detection enables a clinician to make patient management decisions, e.g., upgrading from a single atrial chamber pacing therapy to a dual chamber pacing therapy.

User interface 56 may include a mouse, touch screen, keypad or the like to enable a user to interact with external device 20 to initiate a telemetry session with pacemaker 14 for retrieving data from and/or transmitting data to pacemaker 14, including programmable parameters for controlling cardiac event sensing and therapy delivery. Telemetry unit 58 includes a transceiver and antenna configured for bidirectional communication with a telemetry circuit included in pacemaker 14 and is configured to operate in conjunction with processor 52 for sending and receiving data relating to pacemaker functions via communication link 24. Telemetry unit 58 may establish a wireless bidirectional communication link 24 with pacemaker 14. Communication link 24 may be established using a radio frequency (RF) link such as BLUETOOTH®, Wi-Fi, Medical Implant Communication Service (MICS) or other communication bandwidth. In some examples, external device 20 may include a programming head that is placed proximate pacemaker 14 to establish and maintain a communication link 24, and in other examples external device 20 and pacemaker 14 may be configured to communicate using a distance telemetry algorithm and circuitry that does not require the use of a programming head and does not require user intervention to maintain a communication link.

It is contemplated that external device 20 may be in wired or wireless connection to a communications network via a telemetry circuit that includes a transceiver and antenna or via a hardwired communication line for transferring data to a centralized database or computer to allow remote management of the patient. Remote patient management systems including a centralized patient database may be configured to utilize the presently disclosed techniques to enable a clinician to be notified when AV block criteria are determined to be met by pacemaker 14. Review of AV block detection data, EGM, motion sensor signal, and marker channel data may be performed remotely by a clinician who may authorize programming of sensing and therapy control parameters in pacemaker 14, e.g., after viewing a visual representation of AV block related data, EGM, motion sensor signal and marker channel data.

Figure 2:
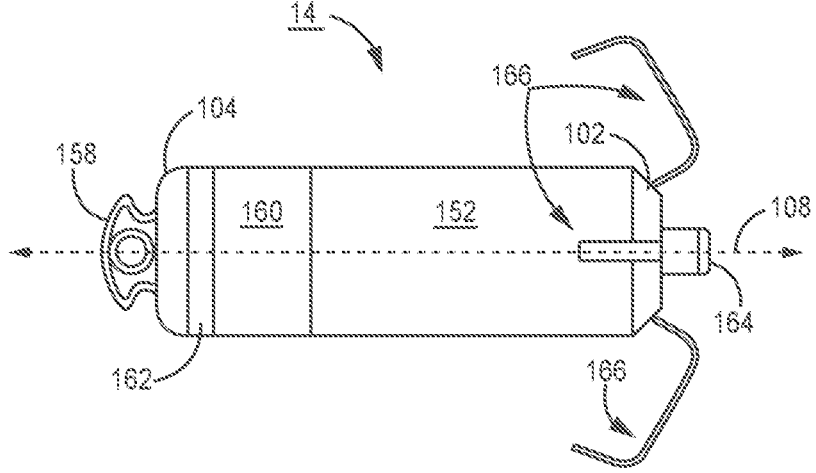
FIG. 2 is a conceptual diagram of the atrial pacemaker shown in FIG. 1.

FIG. 2 is a conceptual diagram of the pacemaker 14 shown in FIG. 1. Pacemaker 14 includes electrodes 162 and 164 spaced apart along the housing 150 of pacemaker 14 for sensing cardiac electrical signals and delivering pacing pulses. Electrode 164 is shown as a tip electrode extending from a distal end 102 of pacemaker 14, and electrode 162 is shown as a ring electrode along a mid-portion of housing 150, for example adjacent proximal end 104. Distal end 102 is referred to as "distal" in that it is expected to be the leading end as pacemaker 14 is advanced through a delivery tool, such as a catheter, and placed against a targeted pacing site.

Electrodes 162 and 164 form an anode and cathode pair for bipolar cardiac pacing and sensing. In alternative embodiments, pacemaker 14 may include two or more ring electrodes, two tip electrodes, and/or other types of electrodes exposed along pacemaker housing 150 for delivering electrical stimulation to heart 8 and sensing cardiac electrical signals. Electrodes 162 and 164 may be, without limitation, titanium, platinum, iridium or alloys thereof and may include a low polarizing coating, such as titanium nitride, iridium oxide, ruthenium oxide, platinum black, among others. Electrodes 162 and 164 may be positioned at locations along pacemaker 14 other than the locations shown.

Housing 150 is formed from a biocompatible material, such as a stainless steel or titanium alloy. In some examples, the housing 150 may include an insulating coating. Examples of insulating coatings include parylene, urethane, PEEK, or polyimide, among others. The entirety of the housing 150 may be insulated, but only electrodes 162 and 164 uninsulated. Electrode 164 may serve as a cathode electrode and be coupled to internal circuitry, e.g., a pacing pulse generator and cardiac electrical signal sensing circuitry, enclosed by housing 150 via an electrical feedthrough crossing housing 150. Electrode 162 may be formed as a conductive portion of housing 150 defining a ring electrode that is electrically isolated from the other portions of the housing 150 as generally shown in FIG. 2. In other examples, the entire periphery of the housing 150 may function as an electrode that is electrically isolated from tip electrode 164, instead of providing a localized ring electrode such as electrode 162. Electrode 162 formed along an electrically conductive portion of housing 150 serves as a return anode during pacing and sensing.

The housing 150 may include a control electronics subassembly 152 and a battery subassembly 160, which provides power to the control electronics subassembly 152. Control electronics subassembly 152 houses the electronics for sensing cardiac signals, producing pacing pulses and controlling therapy delivery and other functions of pacemaker 14 as described herein. A motion sensor may be implemented as an accelerometer enclosed within housing 150 in some examples. The accelerometer provides a signal to a processor included in control electronics subassembly

152 for signal processing and analysis for detecting cardiac mechanical event signals, e.g., ventricular event signals, for use in detecting AV block as described herein.

The accelerometer may be a multi-axis or multi-dimensional accelerometer where each axis of the accelerometer generates an acceleration signal in a different dimension. In some examples, the accelerometer may have one "longitudinal" axis that is parallel to or aligned with the longitudinal axis 108 of pacemaker 14 and two orthogonal axes that extend in radial directions relative to the longitudinal axis 108. Practice of the techniques disclosed herein, however, are not limited to a particular orientation of the accelerometer within or along housing 150 or a particular number of axes. A one-dimensional accelerometer may be used to obtain a motion signal from which cardiac mechanical events may be detected and a ventricular event metric may be determined. In other examples, a two dimensional accelerometer or other multi-dimensional accelerometer may be used. Each axis of a single or multi-dimensional accelerometer may be defined by a piezoelectric element, micro-electrical mechanical system (MEMS) device or other sensor element capable of producing an electrical signal in response to changes in acceleration imparted on the sensor element, e.g., by converting the acceleration to a force or displacement that is converted to the electrical signal. In a multi-dimensional accelerometer, the sensor elements may be arranged orthogonally with each sensor element axis orthogonal relative to the other sensor element axes. Orthogonal arrangement of the elements of a multi-axis accelerometer, however, is not necessarily required.

Each sensor element or axis may produce an acceleration signal corresponding to a vector aligned with the axis of the sensor element. A vector signal of a multi-dimensional accelerometer (also referred to herein as a "multi-axis" accelerometer) for use in sensing cardiac mechanical events or determining cardiac event metrics may be selected as a single axis signal or a combination of two or more axis signals. For example, one, two or all three axis signals produced by a three dimensional accelerometer may be selected for processing and analysis for use in determining when AV block criteria are met by pacemaker 14.

Pacemaker 14 may include features for facilitating deployment and fixation of pacemaker 14 at an implant site. For example, pacemaker 14 may include a set of fixation tines 166 to secure pacemaker 14 to patient tissue, e.g., by actively engaging with the atrial endocardium and/or interacting with the atrial pectinate muscle. Fixation tines 166 are configured to anchor pacemaker 14 to position electrode 164 in operative proximity to a targeted tissue for delivering therapeutic electrical stimulation pulses. Numerous types of active and/or passive fixation members may be employed for anchoring or stabilizing pacemaker 14 in an implant position. Pacemaker 14 may optionally include a delivery tool interface 158. Delivery tool interface 158 may be located at the proximal end 104 of pacemaker 14 and is configured to connect to a delivery device, such as a catheter, used to position pacemaker 14 at an implant location during an implantation procedure, for example within an atrial chamber.

Figure 3:
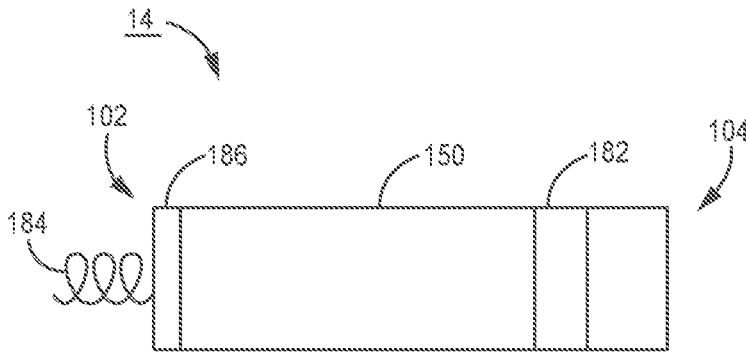
FIG. 3 is a conceptual diagram of an atrial pacemaker according to another example.

FIG. 3 is a conceptual diagram of pacemaker 14 according to another example. In FIG. 2, the cathode tip electrode 164 is shown as a button or hemispherical type electrode that may contact the atrial endocardial tissue when distal end 102 is anchored at an implant site by fixation tines 166. In the example of FIG. 3, the cathode tip electrode 184 is shown as a screw-in helical electrode which may provide fixation of pacemaker 14 at the implant site as well as serving as a pacing/sensing electrode. In the example of FIG. 3, pacemaker 14 may be configured to provide dual chamber pacing when electrode 184 is advanced from within the right atrial chamber to a His bundle pacing location or ventricular septal pacing location.

In this case, tip electrode 184 and return anode electrode 182 may be used for pacing the ventricles, e.g., via the His bundle when AV block is detected by pacemaker 14. A second cathode electrode 186 may be provided at or near distal end 102 for providing atrial pacing and sensing in combination with the return anode 182 in some examples. Pacemaker 14 may include two or more electrodes which may be ring electrodes, helical electrodes, hook electrodes, button electrodes, hemispherical electrodes or other types of electrodes arranged along housing 150 for providing at least atrial sensing and pacing (which may include far field R-wave sensing from the atrial signal) and may further provide ventricular electrical signal sensing (e.g., R-wave sensing) and/or ventricular pacing, e.g., via the His bundle, in some examples. Examples of various electrode arrangements that may be included in a pacemaker configured to perform the AV block determination techniques disclosed herein are generally disclosed in U.S. Publication No. 2019/0083779 (Yang, et al.), incorporated herein by reference in its entirety.

Figure 4:
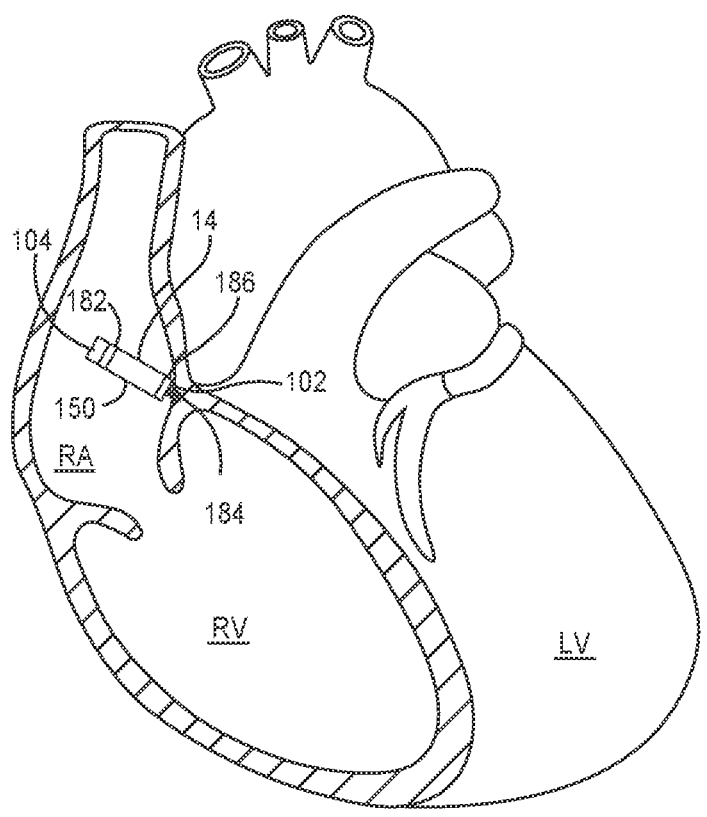
FIG. 4 is conceptual diagram of the pacemaker of FIG. 3 shown implanted in the RA at an implant site for providing dual chamber pacing and sensing according to one example.

FIG. 4 is conceptual diagram of the pacemaker 14 of FIG. 3 shown implanted in the RA at an implant site for providing dual chamber pacing and sensing according to one example. The distal end 102 of pacemaker 14 may be positioned at the inferior end of the interatrial septum, beneath the AV node and near the tricuspid valve annulus to position tip electrode 184 for advancement into the interatrial septum toward the His bundle. Ring electrode 182 spaced proximally from tip electrode 184 may be used as the return electrode with the cathode tip electrode 184 for pacing the right and left ventricles via the His-Purkinje system. The distal ring electrode 186 may be used in combination with the proximal ring electrode 182 for sensing atrial P-waves and delivering atrial pacing pulses. In this position, a motion sensor included in pacemaker 14 may produce a signal including ventricular event signals. Pacemaker 14 may be configured to detect or confirm AV block based on the motion signal produced by the motion sensor. Pacemaker 14 may be configured to respond to determining that AV block criteria are met by delivering ventricular pacing pulses via electrode 184 to provide ventricular rate support.

Figure 5:
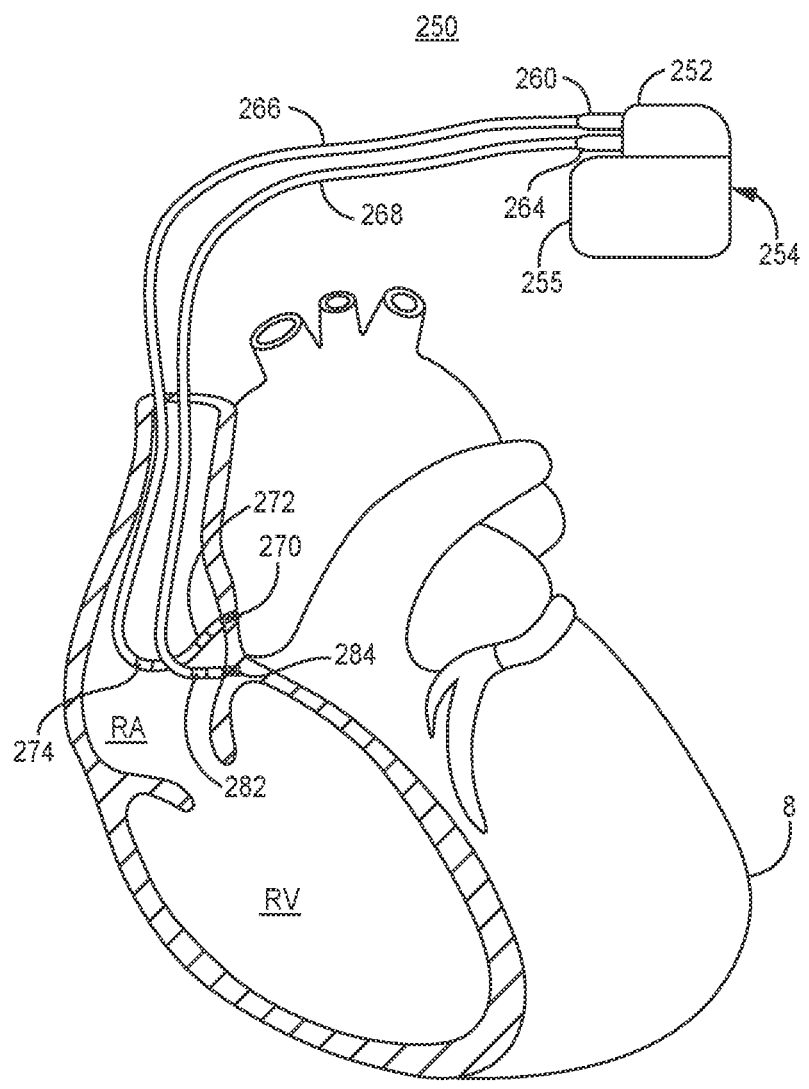
FIG. 5 is a conceptual diagram of a medical device system capable of pacing a patient's heart and sensing cardiac electrical signals and cardiac motion signals for determining AV block according to another example.

FIG. 5 is a conceptual diagram of a medical device system 250 capable of pacing a patient's heart 8 and sensing cardiac electrical signals and cardiac motion signals for determining when AV block criteria are met according to another example. The system 250 includes a pacemaker 254 coupled to a patient's heart 8 via at least one transvenous medical electrical lead 266 and/or lead 268. Pacemaker 254 is shown as a dual chamber device capable of delivering cardiac pacing pulses and sensing cardiac electrical signals in an atrial chamber and in a ventricular chamber using an electrode 284 advanced from the RA to a His bundle pacing location. In other examples, pacemaker 254 may be configured as single chamber device, e.g., coupled to only a signal lead 266 extending into the RA for RA sensing and pacing. Pacemaker housing 255 encloses internal circuitry corresponding to the various circuits and components, for example as described in conjunction with FIG. 6 below, for sensing cardiac electrical signals from heart 8, sensing cardiac motion signals for use in determining when AV block criteria are met, and controlling electrical stimulation therapy, e.g., pacing therapy, delivered by pacemaker 254.

Pacemaker 254 includes a connector block 252 that may be configured to receive the proximal ends of an atrial pacing and sensing lead 266, referred to hereafter as "atrial lead" 266, and/or a ventricular pacing and sensing lead 268, referred to hereafter as "ventricular lead" 268. Each of leads 266 and 268 are advanced transvenously for positioning electrodes for sensing and stimulation of the atria and the ventricles, respectively. Atrial lead 266 may be positioned such that its distal end is in the vicinity of the right atrium (RA). Atrial lead 266 is equipped with pacing and sensing electrodes, shown as a tip electrode 270 and a ring electrode 272 spaced proximally from tip electrode 270. The electrodes 270 and 272 provide sensing and pacing in the RA and are each connected to a respective insulated conductor extending within the elongated body of atrial lead 266. Each insulated conductor is coupled at its proximal end to a connector carried by proximal lead connector 260, and thereby electrically coupled to internal pacemaker circuitry via connector block 252.

Atrial lead 266 may include an accelerometer 274 carried by the atrial lead body for positioning within the RA for sensing cardiac motion signals. Accelerometer 274 may produce cardiac motion signals received by circuitry enclosed by pacemaker housing 255 via an electrical conductor extending within the lead body to proximal connector 260. Accelerometer 274 generates a motion signal sensed from within the RA. The motion signal may include ventricular event signals, e.g., as described below in conjunction with FIGS. 9 and 10 and other diagrams presented herein. The ventricular event signal may be detected by processing circuitry included in pacemaker 250. As described below, a cardiac motion signal sensed from within the RA may be used for detecting ventricular event signals and for detecting AV block. One or more ventricular event metrics correlated to the strength, frequency and/or regularity of ventricular event signal may be determined from the motion signal over multiple atrial cycles for determining when AV block criteria are met. In some examples, pacemaker 254 is a single chamber pacemaker coupled only to the atrial lead 266 for sensing cardiac electrical signals, sensing cardiac motion signals, and delivering atrial pacing pulses.

Ventricular lead 268, when included, may be advanced within the right atrium to position electrodes 282 and 284 for pacing and sensing in the vicinity of the His bundle from a right atrial approach, as shown. Ventricular lead tip electrode 284 may be a helical electrode that may be advanced into the inferior end of the interatrial septum, beneath the AV node and near the tricuspid valve annulus to position tip electrode 284 in or proximate to the His bundle. A ring electrode 282 spaced proximally from tip electrode 284 may be used as the return electrode with the cathode tip electrode 284 for pacing the right and left ventricles via the His-Purkinje system. While lead 268 is referred to herein as a ventricular pacing and sensing lead for delivering pacing pulses for pacing the ventricles, ventricular lead 268 may be referred to as a "His bundle pacing and sensing lead" when positioned for delivering pacing pulses to the ventricles via the His-Purkinje system from the right atrial approach.

The electrodes 282 and 284 are coupled to respective insulated conductors extending within the elongated body of ventricular lead 268, which provide electrical connection to the proximal lead connector 264 coupled to connector block 252, and electrical connection to circuitry enclosed by housing 255 is thereby achieved. Cardiac electrical signal sensing circuitry included in pacemaker 254 may receive a cardiac electrical signal from electrodes 282 and 284 of ventricular lead 268 for sensing ventricular R-waves. While atrial lead 266 and ventricular lead 268 are each shown carrying two electrodes, it is recognized that each lead may carry one or more electrodes for providing one or more selectable pacing and/or sensing electrode vectors, which may include bipolar combinations of electrodes carried by the respective lead or unipolar combinations of an electrode carried by the respective lead and the pacemaker housing 255. Furthermore while atrial lead 266 is shown including accelerometer 274, it is understood that one or both of leads 266 and 268 may include a motion sensor such as acceler-ometer 274 for producing a cardiac motion signal due to acceleration forces imparted on accelerometer 274. Accel-erometer 274 may be a single or multi-axis accelerometer as described above. Circuitry enclosed by housing 255 includes processing circuitry for detecting ventricular event signals and/or determining one or more ventricular event metrics according to techniques disclosed herein from the accelera-tion signal produced by accelerometer 274 and determining when AV block criteria are met based on ventricular event signals (or the absence thereof) and/or the one or more ventricular event metrics.

In some examples, pacemaker 254 is configured as a dual-chamber pacemaker capable of sensing and pacing in the RA and sensing ventricular R-waves and delivering atrial synchronized ventricular pacing pulses, e.g., in atrial-track-ing ventricular pacing modes. In other examples, pacemaker 254 may be coupled to a single lead advanced into the RA for sensing both atrial and ventricular signals (e.g., FFRWs) and delivering at least atrial pacing pulses. In still other examples, pacemaker 254 may be a single chamber pacing device coupled only to ventricular lead 268. In this case, accelerometer 274 may be carried by lead 268 for position-ing within the RA for detecting AV block. Pacemaker 254 may be configured to detect AV block when AV block criteria are met based on an analysis of the signal received from accelerometer 274 for use in controlling ventricular pacing delivered via electrode 284, particularly when ven-tricular electrical signal sensing is compromised, e.g., due to noise or low signal strength.

In some cases, pacemaker 254 may be configured for dual chamber sensing of both atrial electrical signals and ven-tricular electrical signals. AV block may be detected based on the accelerometer signal, which may confirm or support AV block detection made based on electrical signals and/or support AV block detection when electrical signals are unreliable. In response to detecting AV block, ventricular pulses may be delivered by pacemaker 254 to for at least maintaining a minimum ventricular rate and/or delivering atrial synchronized ventricular pacing. It is to be understood that in some examples, pacemaker 254 may be configured as an implantable cardioverter defibrillator capable of deliver-ing both low voltage cardiac pacing therapies and high voltage cardioversion and defibrillation (CV/DF) shocks. In this case, Pacemaker 254 may be coupleable to at least one lead carrying at least one high voltage CV/DF electrode such as an elongated coil electrode.

Figure 6:
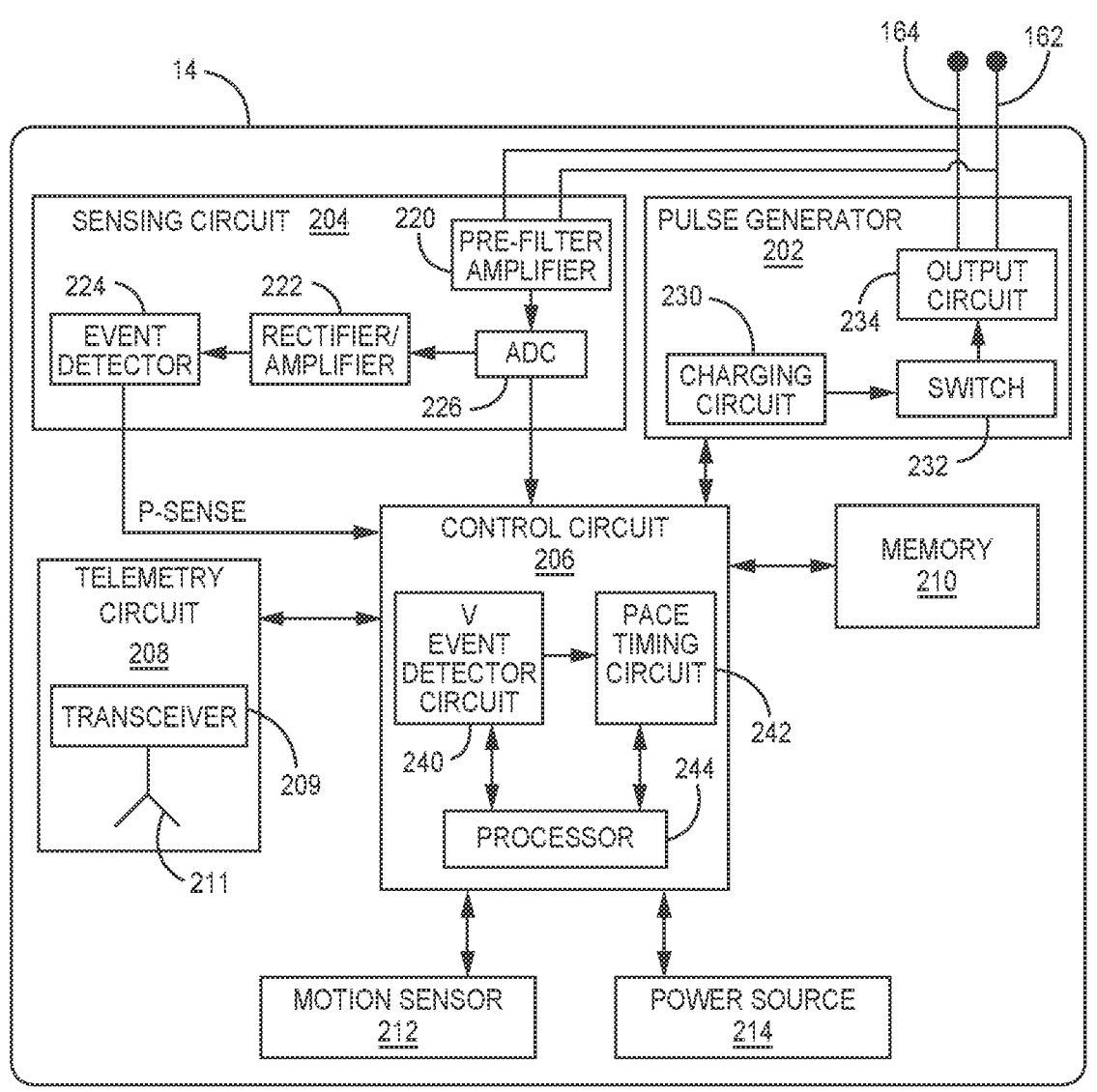
FIG. 6 is a conceptual diagram of an example configuration of the atrial pacemaker shown in FIG. 1.

FIG. 6 is a conceptual diagram of an example configu-ration of pacemaker 14 shown in FIG. 1 or FIG. 4. FIG. 6 is described in the context of pacemaker 14 of FIG. 1; however it is to be understood that circuitry and components and the associated functionality described in conjunction with FIG. 6 may be incorporated in pacemaker 14 shown in FIG. 4 or pacemaker 254 of FIG. 5. Pacemaker 14 includes a pulse generator 202, a cardiac electrical signal sensing circuit 204, a control circuit 206, memory 210, telemetry circuit 208, motion sensor 212 and a power source 214. The various circuits represented in FIG. 6 may be combined on one or more integrated circuit boards which include a specific integrated circuit (ASIC), an electronic circuit, a processor (shared, dedicated, or group) and memory that execute one or more software or firmware programs, a combinational logic circuit, state machine or other suitable components that provide the described functionality.

Motion sensor 212 may include an accelerometer in the examples described herein. Motion sensor 212 is not limited to being an accelerometer, however, and other motion sen-sors may be utilized successfully in pacemaker 14 for detecting cardiac motion signals according to the techniques described herein. Examples of motion sensors that may be implemented in motion sensor 212 include piezoelectric sensors and MEMS devices. Motion sensor 212 may be enclosed by the housing 150 (shown in FIG. 2) of leadless pacemaker 14. However, in the case of a pacemaker coupled to epicardial or transvenous leads, such as pacemaker 254 of FIG. 5, including a motion sensor 212 within the pacemaker housing 255 may be optional. Instead a motion sensor is carried by a transvenous lead coupled to pacemaker 254, e.g., accelerometer 274 as shown in FIG. 5, for positioning within the atrial chamber for sensing intra-atrial motion signals. In some examples, motion sensor 212 may be included within the housing 255 of the pacemaker 254, in addition to a lead-based motion sensor, and configured for sensing motion due to patient physical activity and/or accel-eration signal changes due to patient posture changes.

Motion sensor 212 (or lead-based accelerometer 274) may include a multi-axis sensor, e.g., a two-dimensional or three-dimensional accelerometer, with each axis providing an axis signal that may be analyzed individually or in combination for detecting cardiac mechanical events and determining ventricular event metrics as described below. Motion sensor 212 produces an electrical signal correlated to motion or vibration of sensor 212 (and pacemaker 14), e.g., when subjected to flowing blood and cardiac motion. The motion sensor 212 may include one or more filter, amplifier, rectifier, analog-to-digital converter (ADC) and/or other components for producing a motion signal that is passed to control circuit 206. For example, each vector signal pro-duced by each individual axis of a multi-axis accelerometer may be filtered by a high pass filter, e.g., a 10 Hz high pass filter, or a bandpass filter, e.g., a 10 Hz to 30 Hz bandpass filter. The filtered signal may be digitized by an ADC and rectified for use by ventricular (V) event detector circuit 240 for detecting ventricular event signals. The high pass filter may be raised (e.g., to 15 Hz) if needed to detect ventricular event signals that have higher frequency content. In some examples, high pass filtering is performed with no low pass filtering. In other examples, each accelerometer axis signal is filtered by a low pass filter, e.g., a 30 Hz low pass filter, with or without high pass filtering. Other signal processing and analysis techniques may be used for detecting ventricu-lar event signals, such as fast Fourier transform, determining a differential signal, or determining a number of threshold crossings by the motion signal where the threshold may be greater than or less than the amplitude of atrial event signals.

In some examples, a signal from at least one axis of an accelerometer included in motion sensor 212 may be passed to control circuit 206 for determining patient posture and/or a patient physical activity metric in addition to using the motion signal for determining when AV block criteria are met, which may be used for detecting AV block (or con-firming AV conduction when AV block criteria are not met). Acceleration forces on the motion sensor 212 occur due to patient posture changes relative to gravitational acceleration forces and due to patient motion during physical activity, such as exercise and activities of daily living. The accelerometer axis signals may also be used for determining patient posture and discriminating between a horizontal or non-upright position and non-horizontal or upright positions.

Patient posture may be determined by control circuit 206 from one or more accelerometer axis signals for detecting AV block monitoring conditions in some examples. For instance, AV block monitoring may be performed during daytime hours, when the patient is not asleep or resting. Control circuit 206 may detect a non-horizontal or upright patient posture from the accelerometer axis signals and enable AV block monitoring based on detecting the non-horizontal patient posture in some examples.

A patient physical activity metric correlated to the level of physical exertion and metabolic demand of the patient may be determined from the motion sensor signal. The patient activity metric may be used by control circuit 206 to detect AV block monitoring conditions. For example, control circuit 206 may enable determination of a ventricular event metric from the motion signal for AV block monitoring in response to detecting a patient actively level that is less than a threshold level, which may correspond to moderate activity or activities corresponding to exercise induced heart rates of 100 beats per minute or less.

Control circuit 206 may determine the patient activity metric for determining a sensor indicated pacing rate for providing rate responsive pacing during increased patient activity in some examples. The accelerometer axis signal(s) used for determining a patient activity metric may be filtered differently than the axis signals used for determining ventricular event metric(s), detecting ventricular event signals and/or detecting AV block. For example, motion sensor 212 may include a low pass filter having an upper cutoff frequency of 10 Hz for passing a low pass filtered patient activity signal to processor 244 for determining a patient activity metric. Motion sensor 212 may include bandpass filter having a lower cutoff frequency of 10 Hz or higher and an upper cutoff frequency of 30 Hz for passing a bandpass filtered cardiac motion signal from one or more of the accelerometer axes to ventricular event detector circuit 240 for detecting ventricular event signals or more generally for determining a ventricular event metric from the motion signal over multiple atrial cycles.

The patient activity metric may be determined by control circuit 206 at a desired frequency, e.g., every two seconds, for use in determining a sensor-indicated pacing rate (SIR) that meets the metabolic requirements of the patient based on physical activity. The SIR may vary between the programmed minimum lower rate during periods of rest (minimal activity metric) and a maximum upper pacing rate during periods of maximum exertion. The SIR may be determined according to an SIR transfer function, which may include different rates of change of the SIR over different ranges of the patient activity metric. Control circuit 206 may enable AV block monitoring when the SIR is less than a threshold rate, the time of day is daytime, and/or the patient posture is upright, as examples.

In some examples, the activity metric is determined as an activity count. In these instances, control circuit 206 includes a counter that may track the activity count as the number of times the patient activity signal from motion sensor 212 crosses a threshold amplitude during an activity count interval, for example a 2-second interval. The count at the end of each activity count interval is correlated to patient body motion during the activity count interval and is therefore correlated to patient metabolic demand. Example methods for obtaining an activity count over an n-second interval are generally disclosed in U.S. Pat. No. 5,720,769 (van Oort), incorporated herein by reference in its entirety.

In other examples, an activity metric may be obtained from the patient physical activity signal by integrating or summing activity signal sample points over an activity count interval, e.g., a two-second interval though longer or shorter intervals of time may be used for determining an activity metric. The activity metric may be converted to a target heart rate to meet the patient's metabolic demand. The target heart rate may be converted to an SIR based on an SIR transfer function that includes a lower rate set point and an activity of daily living (ADL) range and a maximum upper rate. Examples of methods for establishing an SIR transfer function applied to patient activity metrics determined from an intracardiac motion signal are generally disclosed in U.S. Pat. No. 9,724,518 (Sheldon, et al.), incorporated herein by reference in its entirety.

One example of an accelerometer for use in implantable medical devices that may be implemented in conjunction with the techniques disclosed herein is generally disclosed in U.S. Pat. No. 5,885,471 (Ruben, et al.), incorporated herein by reference in its entirety. An implantable medical device arrangement including a piezoelectric accelerometer for detecting patient motion is disclosed, for example, in U.S. Pat. No. 4,485,813 (Anderson, et al.) and U.S. Pat. No. 5,052,388 (Sivula, et al.), both of which patents are hereby incorporated by reference herein in their entirety. Examples of three-dimensional accelerometers that may be implemented in pacemaker 14 and used for detecting cardiac mechanical events and determining ventricular event metrics using the presently disclosed techniques are generally described in U.S. Pat. No. 5,593,431 (Sheldon) and U.S. Pat. No. 6,044,297 (Sheldon), both of which are incorporated herein by reference in their entirety. Other accelerometer designs may be used for producing an electrical signal that is correlated to motion imparted on pacemaker 14 due to ventricular and atrial mechanical events.

Sensing circuit 204 is configured to receive at least one cardiac electrical signal via electrodes coupled to pacemaker 14, e.g., electrodes 162 and 164. The cardiac electrical signal is received by a pre-filter and amplifier circuit 220. Pre-filter and amplifier circuit 220 may include a high pass filter to remove DC offset, e.g., a 2.5 to 5 Hz high pass filter, or a wideband filter having a bandpass of 2.5 Hz to 100 Hz or narrower to remove DC offset and high frequency noise. Pre-filter and amplifier circuit 220 may further include an amplifier to amplify the "raw" cardiac electrical signal passed to analog-to-digital converter (ADC) 226. ADC 226 may pass a multi-bit, digital electrogram (EGM) signal to control circuit 206 for storage in memory 210 and/or further analysis. For example, the EGM signal may be used by ventricular event detector circuit 240 in identifying atrial electrical events (e.g., sensed P-waves) and/or FFRWs. Identification of FFRWs may be used in confirming ventricular events. Identification of sensed P-wave may be used in setting windows for detecting ventricular events from the motion signal, comparing an atrial rate to a ventricular event rate, and/or normalizing a ventricular event metric determined from the motion signal for detecting AV block as described below in conjunction with the accompanying diagrams and flow charts. An episode of the EGM signal passed to control circuit 206 from ADC 226 may be stored in memory 210 in response to AV block criteria being met.

The digital signal from ADC 226 may be passed to rectifier and amplifier circuit 222, which may include a rectifier, bandpass filter, and amplifier for passing a cardiac signal to cardiac event detector 224. Cardiac event detector

224 may include a sense amplifier or other detection circuitry that compares the incoming rectified, cardiac electrical signal to a cardiac event sensing threshold, which may be an auto-adjusting threshold. For example, when the incoming signal crosses a P-wave sensing threshold, the cardiac event detector 224 produces a P-wave sensed event signal (P-sense) that is passed to control circuit 206. In other examples, cardiac event detector 224 may receive the digital output of ADC 226 for detecting P-waves by a comparator, morphological signal analysis of the digital EGM signal or other P-wave detection techniques.

Processor 244 may provide sensing control signals to sensing circuit 204, e.g., P-wave sensing threshold, sensitivity, and various blanking and refractory intervals applied to the cardiac electrical signal for controlling P-wave sensing. P-wave sensed event signals passed from cardiac event detector 224 to control circuit 206 may be used for scheduling atrial pacing pulses by pace timing circuit 242 and for use in setting windows for detecting ventricular events by ventricular event detector circuit 240 from a signal received from motion sensor 212. P-wave sensed event signals may be used by control circuit 206 for identifying multiple atrial cycles over which a ventricular event metric is determined for use in AV block detection.

In some examples, cardiac event detector 224 may be configured to detect FFRWs from the atrial signal received by electrodes 162 and 164. FFRWs may be sensed based on an R-wave sensing threshold crossing, which may occur after an atrial pacing pulse or sensed P-wave. In other examples, control circuit 206 may detect FFRWs from the digital EGM signal passed to control circuit 206 from ADC 226. FFRWs may be detected based on a morphological analysis of the atrial EGM signal or an FFRW sensing threshold amplitude crossing by the atrial EGM signal. Sensing circuit 204 may include a P-wave sensing channel and an FFRW sensing channel. Components included in the P-wave sensing channel and the FFRW sensing channel may be shared between both channels in some examples. For example, pre-filter/amplifier 220 and ADC 226 may be shared by both channels with the output of ADC 226 being passed to a P-wave detector and to an FFRW detector. Different filtering and amplification may be applied to the output of ADC 226 before passing the signal to the respective P-wave detector and FFRW detector.

In examples that include an electrode advanced to the His bundle for ventricular pacing, additional electrode(s) may be coupled to cardiac electrical signal sensing circuit 204. For example, tip electrode 184 as shown in FIGS. 3 and 4 may be coupled to sensing circuit 204 for sensing ventricular R-waves by cardiac event detector 224 based on an R-wave sensing threshold crossing. In the case of pacemaker 254 which may be coupled to both an atrial lead and a ventricular lead, sensing circuit 204 may include two sensing channels, one for sensing atrial P-waves and one for sensing ventricular R-waves.

Control circuit 206 includes a ventricular event detector circuit 240, pace timing circuit 242, and processor 244. Control circuit 206 may receive P-wave sensed event signals and/or digital cardiac electrical signals from sensing circuit 204 for use in detecting and confirming cardiac events and controlling atrial pacing (and in some examples ventricular pacing via the His bundle). For example, P-wave sensed event signals may be passed to pace timing circuit 242 for starting a new atrial pacing escape interval. In some examples, FFRW or R-wave sensed event signals may also be passed to control circuit 206 for use in detecting or confirming ventricular events and AV block.

Ventricular event detector circuit 240 is configured to detect ventricular events or determine ventricular event metric(s) from a signal received from motion sensor 212. Techniques for detecting ventricular events and determining ventricular event metrics are described below. In some examples, ventricular event detector circuit 240 receives a motion signal from motion sensor 212 and may start a ventricular event window in response to identifying an atrial event, e.g., a P-wave sensed event signal from sensing circuit 204 or an atrial pacing pulse delivered by pulse generator 202. The ventricular event window may correspond to a time period after the atrial electrical event during which ventricular mechanical contraction is expected to occur if AV conduction is intact. Ventricular event detector circuit 240 determines if the motion sensor signal satisfies ventricular event detection criteria during the sensing window in some examples. Control circuit 206 may determine a ventricular event metric as a count of ventricular events detected over multiple atrial cycles. Processor 244 may receive ventricular event detection signals from detector circuit 240 for counting the detected ventricular events and determining when AV block criteria are met. A ventricular event may be detected based on a threshold crossing by the motion signal or one or more motion signal features determined during the sensing window as described below in conjunction with FIGS. 7-11 and 14.

In other examples, control circuit 206 may determine a ventricular event metric over multiple atrial cycles without requiring sensing windows. For instance, the ventricular event metric may be an AV activation time in some examples, as described below in conjunction with FIGS. 12-13. In other examples, as described below in conjunction with FIGS. 15-16, the ventricular event metric may include an integration metric determined over a detection time interval that includes multiple atrial cycles. Control circuit 206 may detect AV block, store cardiac signal episodes, generate an alert, adjust a pacing therapy or provide other output in response to the ventricular event metric meeting AV block criteria.

Pace timing circuit 242 may additionally receive P-wave sensed event signals from P-wave detector 224 for use in controlling the timing of pacing pulses delivered by pulse generator 202. Processor 244 may include one or more clocks for generating clock signals that are used by pace timing circuit 242 to time out an atrial pacing interval, e.g., a permanent lower rate pacing interval for treating bradycardia or a temporary lower rate interval for providing rate response pacing. The atrial pacing interval, sometimes referred to as an "escape interval" may be restarted by pace timing circuit 242 in response to each atrial electrical event, e.g., upon receipt of each P-wave sensed event signal and upon delivery of each atrial pacing pulse by pulse generator 202.

Pace timing circuit 242 may include one or more pacing rate interval timers or counters used to time out the pacing escape interval. For example, pace timing circuit 242 may include a timer or counter for timing out the atrial pacing interval, which may be a programmable interval stored in memory 210 and retrieved by processor 244. If a P-wave sensed event signal is not received by control circuit 206 before expiration of the atrial pacing interval, pulse generator 202 generates an atrial pacing pulse in response to the atrial pacing interval expiration.

In examples that include ventricular pacing capabilities by pacemaker 14 (or pacemaker 254), control circuit 206 may control pulse generator 202 to generate ventricular pacing pulses, e.g., delivered by a His bundle pacing electrode 184 or 284. The ventricular pacing pulses may be delivered in a non-atrial tracking ventricular pacing mode, e.g., during atrial tachyarrhythmia. Pace timing circuit 242 may set a ventricular pacing interval set to a lower pacing rate interval or a temporary interval to provide ventricular rate support. The ventricular pacing pulses may be delivered in an atrial tracking pacing mode when control circuit 206 detects AV block. In this case, an AV pacing interval may be set by pace timing circuit 242 in response to P-wave sensed event signals and atrial pacing pulses to synchronize the ventricular pacing pulses to the sensed P-waves and atrial pacing pulses. Upon expiration of an AV pacing interval, pulse generator 202 generates a ventricular pacing pulse delivered via a ventricular pacing electrode vector (e.g., electrodes 184 and 182 shown in FIG. 3 or electrodes 284 and 282 shown in FIG. 5).

While only electrodes 162 and 164 are shown in FIG. 6, it is to be understood from the conceptual diagrams of FIGS. 4 and 5 that any housing-based electrodes, e.g., electrodes 182, 184, and 186, and/or lead-based electrodes, e.g., electrodes 270, 272, 282, and 284, may be electrically coupled to circuitry depicted in FIG. 6 and enclosed by the housing of the pacemaker 14 or 254. As such, housing based electrodes 182, 184, and 186 may be electrically coupled to pulse generator 202 and/or cardiac electrical signal sensing circuit 204 for providing cardiac electrical event signal sensing and delivering pacing pulses. Lead based electrodes 270, 272, 282 and 284 shown in FIG. 5 may be electrically coupled to pulse generator 202 and/or cardiac electrical signal sensing circuit 204 via the conductors carried by the lead bodies 266 and 268 and connector block 252.

Pulse generator 202 generates electrical pacing pulses that are delivered to the RA of the patient's heart via cathode electrode 164 and return anode electrode 162 (or in other examples via electrodes 182 and 186 shown in FIG. 4 or electrodes 270 and 272 shown in FIG. 5). In examples including ventricular pacing capabilities, pulse generator 202 may generate electrical pacing pulses, which may be delivered to the His-Purkinje conduction system using electrodes 184 and 182 (FIG. 4) or electrodes 282 and 284 (FIG. 5). In addition to providing control signals to pace timing circuit 242 and pulse generator 202 for controlling the timing of atrial pacing pulses, processor 244 may retrieve programmable pacing control parameters, such as pacing pulse amplitude and pacing pulse width, which are passed to pulse generator 202 for controlling pacing pulse delivery.

Pulse generator 202 may include charging circuit 230, switching circuit 232 and an output circuit 234. Charging circuit 230 is configured to receive current from power source 214 and may include a holding capacitor that may be charged to a pacing pulse amplitude under the control of a voltage regulator included in charging circuit 230. The pacing pulse amplitude may be set based on a control signal from control circuit 206. Switching circuit 232 may control when the holding capacitor of charging circuit 230 is coupled to the output circuit 234 for delivering the pacing pulse. For example, switching circuit 232 may include a switch that is activated by a timing signal received from pace timing circuit 242 upon expiration of a pacing escape interval and kept closed for a programmed pacing pulse width to enable discharging of the holding capacitor of charging circuit 230. The holding capacitor, previously charged to the pacing pulse voltage amplitude, is discharged across electrodes 162 and 164 (or other selected pacing electrode vector) through the output capacitor of output circuit 234 for the programmed pacing pulse duration. Examples of pacing circuitry generally disclosed in U.S. Pat.

No. 5,507,782 (Kieval, et al.) and in U.S. Pat. No. 8,532,785 (Crutchfield, et al.), both of which patents are incorporated herein by reference in their entirety, may be implemented in pacemaker 14 (or pacemaker 254) for charging a pacing capacitor to a predetermined pacing pulse amplitude under the control of control circuit 206 and delivering a pacing pulse.

Memory 210 may include computer-readable instructions that, when executed by control circuit 206, cause control circuit 206 to perform various functions attributed throughout this disclosure to pacemaker 14 (or pacemaker 254). The computer-readable instructions may be encoded within memory 210. Memory 210 may include any non-transitory, computer-readable storage media including any volatile, non-volatile, magnetic, optical, or electrical media, such as a random access memory (RAM), read-only memory (ROM), non-volatile RAM (NVRAM), electrically-erasable programmable ROM (EEPROM), flash memory, or other digital media with the sole exception being a transitory propagating signal.

Memory 210 may store sensed ventricular event data corresponding to the number and/or timing of ventricular events sensed by ventricular event detector circuit 240 from the signal from motion sensor 212. In some examples, memory 210 includes a buffer that stores a flag for indicating when no ventricular event is detected for an atrial cycle (for counting AV block cycles) and may store a flag when the ventricular event is detected for an atrial cycle (AV conduction cycle). Memory 210 may include a buffer for storing the ventricular event time for use in detecting AV block and/or detecting a trend in AV activation time for monitoring a worsening AV block condition. Memory 210 may store episodes of cardiac electrical signals sensed by sensing circuit 204 and/or episodes of motion signals sensed by motion sensor 212 in response to control circuit 206 determining that AV block criteria are met. Memory 210 may additionally or alternatively store data determined by control circuit 206 relating to sensed cardiac events, from both the cardiac electrical signal and the motion sensor signal, particularly data relating to ventricular event metrics, an AV block detection, data that can be used for determining the percentage of time the patient is likely in AV block and/or severity of an AV block condition.

Control circuit 206 may detect AV block when the motion signal meets AV block criteria over multiple atrial cycles. Control circuit 206 may generate an alert or notification indicating the AV block detection. Telemetry circuit 208 may transmit the AV block detection notification to external device 20. In some examples, pulse generator 202 may generate and deliver ventricular pacing pulses as described above in response to determining that AV block criteria are met or in response to detecting AV block.

Telemetry circuit 208 includes a transceiver 209 and antenna 211 for transferring and receiving data via a radio frequency (RF) communication link. Telemetry circuit 208 may be capable of bi-directional communication with external device 20 (FIG. 1) as described above. Motion sensor signals and cardiac electrical signals, and/or data derived therefrom such as ventricular event metrics may be transmitted by telemetry circuit 208 to external device 20. Programmable control parameters and algorithms for sensing cardiac events, including P-waves (and in some examples FFRWs or R-waves) and ventricular events from the motion signal, and for controlling pacing therapies delivered by pulse generator 202 may be received by telemetry circuit 208 and stored in memory 210 for access by control circuit 206.

Power source 214 provides power to each of the other circuits and components of pacemaker 14 as required. Power source 214 may include one or more energy storage devices, such as one or more rechargeable or non-rechargeable batteries. The connections between power source 214 and other pacemaker circuits and components are not shown in FIG. 6 for the sake of clarity but are to be understood from the general block diagram of FIG. 6. For example, power source 214 may provide power as needed to charging and switching circuitry included in pulse generator 202; amplifiers, ADC 226 and other components of sensing circuit 204; telemetry circuit 208; memory 210 and motion sensor 212.

The functions attributed to pacemaker 14 (and pacemaker 254) herein may be embodied as one or more processors, controllers, hardware, firmware, software, or any combination thereof. Depiction of different features as specific circuitry is intended to highlight different functional aspects and does not necessarily imply that such functions must be realized by separate hardware, firmware or software components or by any particular circuit architecture. Rather, functionality associated with one or more circuits described herein may be performed by separate hardware, firmware or software components, or integrated within common hardware, firmware or software components. For example, determination of ventricular event features or metrics from the motion sensor signal may be implemented in control circuit 206 executing instructions stored in memory 210 and relying on input from sensing circuit 204 and motion sensor 212. Providing software, hardware, and/or firmware to accomplish the described functionality in the context of any modern pacemaker, given the disclosure herein, is within the abilities of one of skill in the art.

Figure 7:
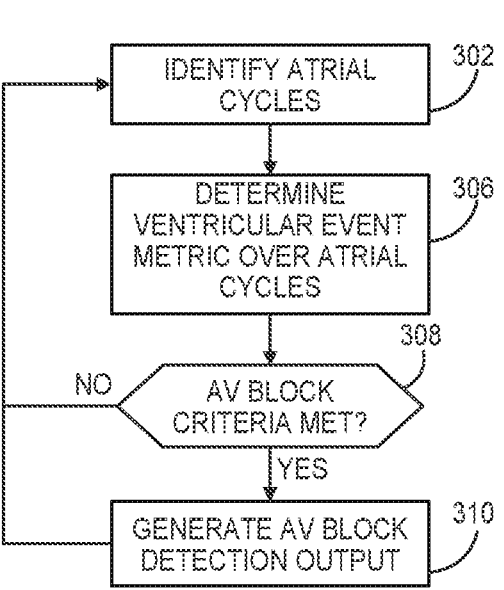
FIG. 7 is a flow chart of a method performed by a medical device for detecting AV block from an intra-atrial motion signal according to one example.

FIG. 7 is a flow chart 300 of a method performed by a medical device for detecting AV block from an intra-atrial motion signal according to one example. At block 302, control circuit 206 identifies multiple atrial cycles. The atrial cycles may each be identified by identifying a leading atrial event that starts the atrial cycle. The atrial events identified by control circuit 206 may be atrial electrical events, e.g., P-waves sensed by sensing circuit 204 and/or atrial pacing pulses generated by pulse generator 202. In some examples, the atrial events are identified by control circuit 206 from the motion signal and correspond to atrial chamber contraction. Control circuit 206 may identify a predetermined number of consecutive atrial cycles in some examples. The atrial cycles may be sampled over time, however, and are not necessarily consecutive. In some examples, non-consecutive groups of consecutive atrial cycles may be identified at block 302. In one illustrative example, three or more consecutive atrial cycles may be identified every thirty seconds, once per minute or other sampling period.

At block 306, control circuit 206 determines a ventricular event metric from the motion sensor signal over the identified atrial cycles. Examples of ventricular event metrics are described below in conjunction with FIGS. 8-16. In some examples, control circuit 206 determines if a ventricular event signal is present in the motion signal received from motion sensor 212 following each identified atrial electrical event, during each identified atrial cycle. For instance, control circuit 206 may set a ventricular event sensing window in response to identifying each atrial event starting an associated atrial cycle. The sensing window may begin 100 ms or less after the atrial electrical event and end up to 500 ms or more after the atrial electrical event. The sensing window starting time and/or ending time may be set differently in response to a sensed P-wave than in response to an atrial pacing pulse because the timing of a ventricular contraction following an intrinsic P-wave may be different than the timing of the ventricular contraction following an atrial pacing pulse. In some examples, the sensing window starting time and/or ending time may be adjusted based on the atrial rate, e.g., based on one or more preceding atrial cycle lengths determined between two consecutively identified atrial events.

Control circuit 206 may determine the ventricular event metric at block 306 by detecting the ventricular events from the motion signal present over the atrial cycles based on a sensing threshold crossing by the motion signal within the sensing window. In other examples, one or more motion signal features may be determined during each sensing window (or during all or a portion of each atrial cycle) for detecting ventricular events over the identified atrial cycles. Such motion signal features may include one or more of, with no limitation intended, the ventricular event time from the atrial event to a sensing threshold crossing, the maximum absolute peak acceleration, the maximum peak-to-peak acceleration, the maximum slope of the acceleration signal, the area of the acceleration signal (e.g., the integral or summation of sample point amplitudes during the sensing window), the time from the atrial electrical event to the maximum absolute peak acceleration, or the morphology of the overall acceleration signal waveform. A motion signal feature or any combination of features may be determined for each atrial cycle for determining the ventricular event metric over the atrial cycles. In some examples, the motion signal feature or combination of features is compared to ventricular event detection criteria for detecting each ventricular event over the atrial cycles, which may include requiring that the ventricular event be detected within a sensing window following each atrial event.

The ventricular event metric may be determined as a count of the detected ventricular events over the atrial cycles, which may be referred to as a count of AV conduction cycles. Alternatively, the ventricular event metric may be determined as a count of the atrial cycles without a ventricular event detection, which may be referred to as a count of AV block cycles. Examples of techniques performed by control circuit 206 for detecting a ventricular event signal during identified atrial cycles are described below in conjunction with FIGS. 9-11 and 14.

In some examples, determining the ventricular event metric at block 306 includes updating an AV conduction cycle count and/or an AV block cycle count. For example, an AV block cycle counter may be increased each time a ventricular event is not detected during an atrial cycle. The counter value may be compared to an AV block threshold value at block 308. In one example, if at least two (or other selected threshold number) of the identified atrial electrical events are identified without detecting a ventricular event following each of the two atrial electrical events, control circuit 206 may determine that AV block criteria are satisfied at block 308. In some instances, control circuit 206 detects AV block in response to a threshold number of consecutive atrial cycles occurring without detection of the ventricular event signal from the motion signal. An AV block cycle counter may be increased for each atrial electrical event that is identified without detecting a ventricular event before the next atrial electrical event (that ends the current atrial cycle). If a ventricular event is detected during an atrial cycle before the AV block cycle counter value reaches an AV block detection threshold, control circuit 206 may reset the AV block cycle counter to zero.

In another example, control circuit 208 may set a flag indicating the detection or absence of a ventricular event signal following each atrial electrical event in a series of consecutive atrial electrical events. A first-in-first out buffer may store the value of the flag (e.g., high or low indicating ventricular event detection or no ventricular event detection, respectively) for each of a series of consecutive atrial cycles. When the ventricular event is not detected from the motion signal by ventricular event detector circuit 240 for two, three, four or more out of a selected number of atrial cycles, e.g., six, eight, ten, twelve or other selected number of atrial cycles, AV block criteria may be determined to be satisfied at block 308 by control circuit 206. A percentage or ratio of the atrial cycles with no ventricular event signal detection out of a predetermined number of atrial cycles may be determined by control circuit 206 as the ventricular event metric at block 306 and compared to AV block criteria at block 308.

In other examples, the ventricular event metric determined at block 306 may be determined by control circuit 206 from the motion signal over multiple atrial cycles without requiring setting sensing windows. For example, a ventricular event metric may be determined as an AV activation time metric based on the time of the ventricular event signal during each atrial cycle as described below in conjunction with FIGS. 12-13. In other examples, control circuit 206 may determine the ventricular event metric by determining an integration metric from the motion signal over a detection time interval that includes the identified atrial cycles. Examples of determining when AV block criteria are met based on a ventricular event metric determined as an integration metric are described below in conjunction with FIGS. 15-16.

In still other examples, the ventricular event metric may be a time interval over which ventricular event signals are not detected. For example, control circuit 206 may start a timer each time ventricular event signal is detected and determine the time until the next ventricular event signal is detected. At block 308, control circuit 206 may compare the time interval to a threshold time interval that indicates AV block is likely. The threshold time interval may be longer during the day than at night in some examples and/or based on the atrial rate. For example, when the time interval between two consecutively detected ventricular event signals is greater than three seconds or other selected threshold, AV block criteria may be determined to be met by control circuit 206 at block 308. In some examples, a longer time interval threshold may be set at night for determination of AV block, e.g., five seconds, six seconds or more. Determination of the time interval between two consecutive ventricular event signals does not necessarily require identifying atrial cycles making block 302 optional for the purpose of determining when AV block criteria are met.

AV block criteria applied by control circuit 206 at block 308 may include determining whether AV block is detected a threshold number of times or for a threshold number of consecutive sequences of atrial cycles. For example, control circuit 206 may detect AV block when the ventricular event signal is detected from the motion signal on less than six out of a sequence of eight consecutive atrial cycles for at least two, three or other selected number of sequences of eight consecutive atrial cycles. The sequences of consecutive atrial cycles may be overlapping or non-overlapping and may be consecutive or non-consecutive sequences of atrial cycles. For instance, control circuit 206 may determine that the ventricular event is detected in less than a threshold number of atrial cycles in the first and third sequences of n consecutive atrial cycles and the ventricular event is detected in more than the threshold number of atrial cycles in the second sequence of n consecutive atrial cycles. Control circuit 206 may determine that AV block criteria are met at block 308 in response to the first and third sequences of consecutive atrial cycles having fewer than a threshold number of atrial cycles associated with a detected ventricular event.

When AV block criteria are unmet at block 308, control circuit 206 may return to block 302 to wait for the next atrial electrical event (or sequence of atrial events or other defined time interval) and continue monitoring the motion signal for determining the next ventricular event metric. When control circuit 206 determines that AV block criteria are met at block 308, control circuit 206 generates an output at block 310. The output may include an AV block alert or notification stored in memory 210, which may be transmitted to external device 20 by telemetry circuit 208. The generated output that may be stored in memory 210 and transmitted to external device 20 may include AV block detection data determined by control circuit 206 and/or an associated episode of the motion signal and/or the cardiac electrical signal, both of which may be stored in memory 210 until a telemetry session is initiated. Control circuit 206 may determine and generate an output of AV block related data by determining the percentage of atrial cycles for which a ventricular event was not detected by ventricular event detector circuit 240, the time or total number of atrial cycles over which AV block was detected, the atrial rate when AV block was detected, and/or the percentage of sensed and paced atrial events associated with no ventricular event detections, as examples.

In some examples, the output generated at block 310 may include a pacing therapy adjustment. In some cases, an atrial pacing rate may be reduced by control circuit 206 in response to AV block criteria being met. Reduction of the atrial pacing rate may promote AV conduction. When pacemaker 14 (or pacemaker 254) is capable of delivering ventricular pacing, as in the example configurations of FIG. 4 and FIG. 5, control circuit 206 may generate an AV block detection output at block 310 by enabling pulse generator 202 to generate ventricular pacing pulses.

In some examples, when pacemaker 14 (or 254) is configured to deliver ventricular pacing pulses, e.g., from an atrial implant location for delivering His bundle pacing, pulse generator 202 may generate a ventricular pacing pulse at block 310 in response to a ventricular event not being detected following an atrial electrical event. For instance, control circuit 206 may enable ventricular back-up pacing in response to detecting AV block. Pace timing circuit 242 may set a back-up ventricular pacing interval. Pulse generator 202 may deliver a ventricular pacing pulse when the back-up ventricular pacing interval expires without a ventricular event signal being detected (from the cardiac electrical signal as a FFRW and/or from the motion signal). The back-up ventricular pacing interval may be started in response to the most recent preceding ventricular event detected. In other examples, the back-up ventricular pacing pulse may be delivered in response to the expiration of a relatively long AV pacing interval, e.g. 300 ms or more, expiring without a ventricular event being detected by ventricular event detector circuit 240. The long AV pacing interval may be started when a P-wave is sensed by sensing circuit 204 or an atrial pacing pulse is delivered by pulse generator 202. In this way, ventricular pacing support may be provided in the absence of a ventricular event during an atrial cycle. In some examples, control circuit 206 may enable delivery of a back-up ventricular pacing pulse during each atrial cycle that a ventricular event is not detected without waiting for the AV block criteria to be met at block 308.

In other examples, at block 310 control circuit 206 may switch the pacing mode from an atrial-only pacing mode to a pacing mode that includes atrial-tracking ventricular pacing in response to AV block criteria being met. Pace timing circuit 242 may set an AV pacing interval in response to each atrial electrical event, and pulse generator 202 may generate ventricular pacing pulses when the AV pacing interval expires without a sensed FFRW, R-wave, or mechanical ventricular event.

Enabling ventricular pacing at block 310 is optional, however. Pacemaker 14 may be configured for delivering single chamber pacing to the RA without having ventricular pacing capabilities but may still be configured to detect AV block to enable other responses to AV block criteria being met, such as generating a notification or alert, storing AV block related data including ventricular event metric(s), motion signal features, EGM and/or motion sensor signal episodes, and/or providing other therapy responses. The AV block data and notification may be transmitted by telemetry circuit 208. The output generated at block 310 may include storing a digital EGM signal episode and/or a digital motion signal episode associated with the AV block criteria being met in memory 210 for later transmission by telemetry circuit 208. To facilitate confirmation of the AV block detection and/or controlling ventricular pacing therapy, the output generated by control circuit 206 at block 310 may include enabling sensing circuit 204 to sense R-waves or FFRWs from a cardiac electrical signal.

The process of FIG. 7 may be performed continuously on a beat by beat basis for detecting whether AV conduction (or block) occurs on each atrial cycle. In other examples, the process of FIG. 7 may be performed on a scheduled and/or triggered basis. For example, control circuit 206 may perform the process of flow chart 350 at one or more scheduled times of day for a predetermined monitoring time period or predetermined number of atrial cycles. The process of detecting whether AV block criteria are met may be scheduled to occur once, twice, three, four, six, or eight times a day, for example, and may be performed over one minute, several minutes, one hour, two hours or other selected time period or predetermined number of atrial cycles (e.g., 10 cycles, 60 cycles, or more). In other examples, the process of flow chart 300 may be performed by control circuit 206 when ventricular electrical events, e.g., R-waves or FFRWs, are not being sensed by sensing circuit 204. For instance, the process of flow chart 300 may be initiated by control circuit 206 when control circuit 206 has not received a sensed ventricular event signal, corresponding to a sensed R-wave or FFRW, from sensing circuit 204 for a predetermined number of atrial cycles or a predetermined time interval.

Figure 8:
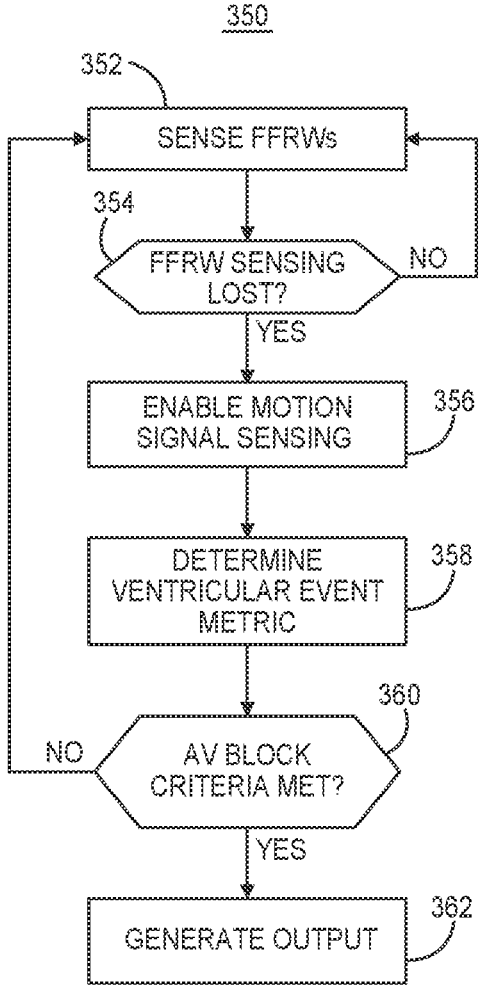
FIG. 8 is a flow chart of a method performed by a pacemaker for detecting AV block according to another example.

FIG. 8 is a flow chart 350 of a method performed by pacemaker 14 (or pacemaker 254) for detecting AV block according to another example. Pacemaker 14 may be configured to sense FFRWs from the cardiac electrical signal received via electrodes 162 and 164. FFRWs may be sensed at block 352 based on an FFRW sensing threshold crossing of the cardiac electrical signal after an atrial blanking period that may follow a sensed P-wave or delivered atrial pacing pulse. In some examples, the cardiac electrical signal is filtered using two different bandpass frequencies for enabling FFRW sensing from one filtered signal and P-wave sensing from a differently filtered signal. The near field P-wave generally has higher frequency components than the FFRW. Sensing circuit 204 may include one filter having a relatively higher bandpass, e.g., 20-60 Hz, for passing P-wave signals enabling event detector 224 of sensing circuit 204 to detect P-waves from the cardiac electrical signal. Sensing circuit 204 may have a second filter having a relatively lower bandpass, e.g., 7-60 Hz, for passing FFRWs. Cardiac event detector 224 may detect FFRWs from the lower bandpass filtered signal, which may be blanked for an atrial blanking period upon each sensed P-wave. Other techniques for sensing FFRWs may be performed by control circuit 206 using the digital EGM signal received from ADC 226, which may include determining a signal width, signal area, peak amplitude, waveform morphology or other signal features or combination of features for sensing FFRWs from the cardiac electrical signal. A variety of techniques may be used for sensing FFRWs from a cardiac electrical signal sensed from the atrial chamber. The techniques disclosed herein are not limited to a particular method for sensing FFRWs from a cardiac electrical signal.

Control circuit 206 may determine when FFRW sensing is lost at block 354. FFRW sensing may be determined to be lost by control circuit 206 when FFRWs are not being sensed in a 1:1 ratio with atrial electrical events (i.e., sensed P-waves and atrial pacing pulses). For example, control circuit 206 may determine that FFRW sensing is lost when no FFRW is sensed during a predetermined number of consecutive atrial cycles, e.g., two, three or other predetermined number of atrial cycles. In other examples, control circuit 206 may determine that FFRW sensing is lost when no FFRW is sensed during more than a predetermined percentage of atrial cycles, e.g., when no FFRW is sensed during more than 20%, 25% or other percentage of the atrial cycles. In some examples, control circuit 206 detects a loss of FFRW sensing when at least X of Y atrial cycles, e.g., 2 out 8 atrial cycles, occur without a sensed FFRW.

In other examples, FFRW sensing may be suspended by control circuit 206 when an atrial tachycardia or atrial fibrillation is present since FFRWs may not be reliably sensed from an atrial EGM signal during a fast atrial rate. Suspended FFRW sensing may be determined as lost FFRW sensing at block 354.

In response to detecting a loss of FFRW sensing, control circuit 206 enables sensing and analysis of the motion signal at block 356. The motion sensor 212 may be powered down until FFRW sensing is lost in some examples to conserve power source 214. When the loss of FFRW sensing is detected, control circuit 206 may enable AV block detection based on the motion signal by controlling power source 214 to deliver current to motion sensor 212. One or more axis signals of a three dimensional accelerometer may be selected for use in determining a ventricular event metric. Accordingly, each accelerometer axis selected for use by control circuit 206 for detecting AV block may be powered by power source 214 at block 356.

In other examples, at least one axis of an accelerometer included in motion sensor 212 may powered to produce an acceleration signal for use in determining a patient physical activity metric. Control circuit 206 may enable AV block monitoring from the motion signal at block 356 by powering additional accelerometer axes for producing axis signals used for determining motion signal features, enable bandpass filtering of one or more accelerometer axis signals by motion sensor 212, and/or enable processor 244 and/or ventricular event detector circuit 240 to perform processing and analysis of the accelerometer axis signal(s) received from motion sensor 212 for AV block detection.

At block 358, control circuit 206 may determine a ventricular event metric over multiple atrial cycles. In some examples, ventricular event detector circuit 240 may determine one or more motion signal features from the motion signal over one or more atrial cycles as described above for determining an AV block cycle count for comparison to AV block criteria at block 360. Additional examples of techniques for determining motion signal features for determining when AV block criteria are met are described below in conjunction with FIGS. 9-16. When control circuit 206 determines that AV block criteria are unmet, control circuit 206 may return to block 352. If FFRW sensing is regained (e.g., when any of the example criteria for detecting a loss of FFRW sensing are no longer met), control circuit 206 may power down the motion sensor or stop processing the motion signal for AV block monitoring and continue sensing FFRWs at block 352. Control circuit 206 may continue to monitor for a loss of FFRW sensing. If a loss of FFRW sensing is still being detected, control circuit 206 continues to process and analyze the motion signal for determining when AV block criteria are met. If the AV block criteria are met at block 360, control circuit 206 generates an output at block 362. Any of the examples given above in conjunction with FIG. 7 as responses to AV block criteria being met may be performed by control circuit 206 at block 362 and may be performed in cooperation with storing an output in memory 210, which may be used by or subsequently passed to sensing circuit 204, pulse generator 202, and/or telemetry circuit 208 as needed. For example, storing a cardiac electrical signal and/or motion signal segment, adjusting a therapy, transmitting data, etc. may be included in the output generated at block 362.

In other examples, instead of sensing FFRWs and enabling motion signal monitoring for AV block when FFRW sensing is lost, control circuit 206 may monitor the motion signal to detect ventricular event signals as evidence of AV conduction. When ventricular event signal sensing from the motion signal is lost, e.g., less than a 1:1 ratio of detected ventricular events to atrial cycles, control circuit 206 may enable FFRW sensing for confirming AV block based on an absence of FFRWs following each atrial event.

Figures 9, 10:
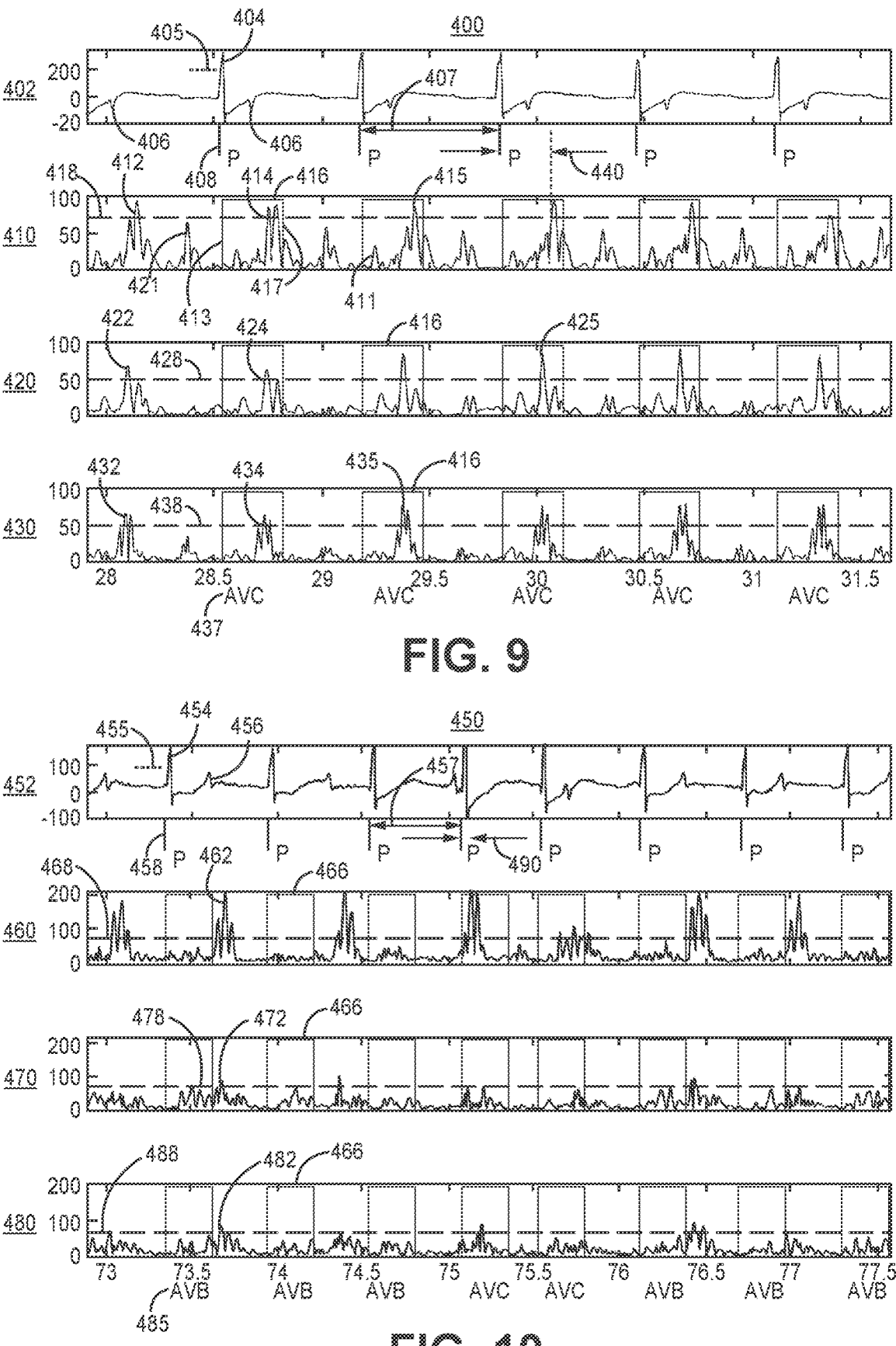
FIG. 9 is an example of a cardiac electrical signal and corresponding accelerometer axis signals that may be produced by a medical device from signals sensed from the patient's heart during AV conduction.
FIG. 10 is diagram of a cardiac electrical signal and accelerometer axis signals that may be produced by a pacemaker during AV block.

FIG. 9 is a diagram 400 of a cardiac electrical signal 402 and simultaneously recorded accelerometer axis signals 410, 420 and 430 during normal AV conduction. The cardiac electrical signal is an atrial EGM signal that may be produced by sensing circuit 204 from signals sensed from the patient's heart via electrodes 162 and 164. The accelerometer axis signals 410, 420 and 430 are rectified filtered signals produced by motion sensor 212. Each accelerometer axis signal 410, 420 and 430 may be produced from a respective axis signal of a three dimensional accelerometer included in motion sensor 212. Each accelerometer axis signal 410, 420 and 430 is bandpass filtered, e.g., by a 10 to 30 Hz bandpass filter, and rectified by motion sensor 212 and passed to control circuit 206.

Cardiac electrical signal 402 includes atrial P-waves 404, each followed by an FFRW 406. Each axis signal 410, 420, and 430 includes ventricular event signals 412, 422 and 432, respectively, following each FFRW 406. In the example of FIG. 9, AV conduction is intact such that each atrial P-wave 404 is conducted to the ventricles as evidenced by the FFRW 406 that follows each P-wave 404 and the subsequent mechanical contraction of the ventricles as evidenced by the ventricular systolic event signals 412, 422 and 432 of each axis signal 410, 420 and 430 (respectively) following each P-wave 404. The term "ventricular systolic event signals" may generally refer to signals present in the motion signal due to closure of the tricuspid and mitral valves, ventricular contraction, and/or opening of the pulmonary and aortic valves.

As illustrated by axis signal 410, each axis signal may include a ventricular diastolic event signal 421 following the ventricular systolic event signal 412. The ventricular diastolic event signal 421 may correspond to the end of ventricular systole and start of ventricular diastole with the closure of the pulmonary and aortic valves and the ventricular relaxation and filling phase of the ventricular cycle. The techniques described herein for detecting a ventricular event may correspond to detecting the ventricular systolic event signals 412 (or 422 or 432) corresponding to ventricular contraction because the ventricular systolic event signal 412 is generally the largest amplitude signal in the motion signal and therefore has the greatest signal strength promoting reliable discrimination between AV conduction and AV block. It is recognized, however, that ventricular signals of the motion signal may include multiple signal peaks corresponding to mechanical activity of the ventricles during ventricular systole and/or diastole, such as the ventricular systolic signal 412 and diastolic signal 421, which may be detected when AV conduction is intact. The absence of those signals 412 and 421 may be evidence for detecting AV block. In some examples, both ventricular systolic event signals and ventricular diastolic event signals present in the motion signal may contribute to a ventricular event metric determined from the motion signal for determining when AV block criteria are met and detecting AV block. Examples of ventricular event metrics determined from the motion signal that may include contributions of both ventricular systolic and ventricular diastolic event signals are described below, e.g., in conjunction with FIGS. 16 and 17 where the ventricular event signal is determined as an integration metric.

Each axis signal may include an atrial event signal 411 (as shown in signal 410) corresponding to atrial contraction subsequent to each P-wave 404. As mentioned previously herein, in some examples, atrial cycles may be identified by identifying the atrial event signals 411 from the motion signal. Since the atrial event signal 411 is relatively small compared to the ventricular event signals 412 and 421, however, when sensing electrodes are available in or on an atrial chamber, the atrial P-wave 404 may be a more reliable signal for identifying atrial cycles than the atrial event signal 411 of the motion signal.

Sensing circuit 204 generates a P-wave sensed event signal 408 in response to sensing each P-wave 404, e.g., in response to the cardiac electrical signal 402 crossing a P-wave sensing threshold 405. Control circuit 206 may identify atrial cycles 407 by identifying an atrial electrical event in response to receiving each P-wave sensed event signal 408. Control circuit 206 may identify multiple atrial cycles 407 by identifying two consecutive atrial events associated with each atrial cycle 407. In some examples, control circuit 206 is configured to identify an atrial cycle 407 in response to receiving a P-wave sensed event signal 408 and, in response to receiving the P-wave sensed event signal, set a ventricular event sensing window 416 applied to one, two or all three accelerometer axis signals 410, 420 and 430 or a combined signal determined as a combination (e.g., a summation) of any two or all three accelerometer axis signals 410, 420 and 430. The ventricular event sensing window 416 may be set by control circuit 206 in response to each P-wave sensed event signal 408.

Sensing window 416 may begin without a delay at starting time 413 upon receipt of P-wave sensed event signal 408. In other examples, sensing window 416 may have a starting time 413 that occurs at a predetermined delay after the P-wave sensed event signal 408, e.g., after 50 ms, 100 ms, 150 ms or other interval, which may serve to blank any atrial motion signals, e.g., atrial event signal 411, present in the accelerometer axis signals 410, 420 and 430 immediately following the P-wave 404. While intrinsic P-waves 404 are shown to be sensed on each atrial cycle in the example of diagram 400, it is to be understood that control circuit 206 may set a ventricular event sensing window 416 following any atrial electrical event, sensed intrinsic P-wave or atrial pacing pulse, when monitoring for AV block.

In the example shown, the ventricular event sensing window 416 has an ending time 417, which may be set to a predetermined time interval after the atrial electrical event, after P-wave sensed event signal 408 in this example. The ending time 417 may be set to 300 ms, 400 ms, 500 ms, 550 ms, 600 ms, 650 ms or other selected time interval after the atrial electrical event. In some examples, the ending time 417 is adjustable by control circuit 206 and may vary with the atrial rate, e.g., increase with longer atrial cycles and decrease with shorter atrial cycles, and/or set differently depending on whether the atrial electrical event is paced or sensed.

The sensing windows 416 are shown to have the same starting time 413 and ending time 417 for all three axis signals 410, 420 and 430. However, the sensing windows 416 may be set uniquely for each axis signal or combinations of signals when more than one axis signal and/or combinations of axis signals are being used for detecting AV block. For example, the sensing window 416 may start earlier or later and/or end earlier or later for a particular axis signal due to the timing relative to the P-wave sensed event signal 408 of the maximum acceleration associated with ventricular contraction along the associated axis of the motion sensor 212.

Control circuit 206 may set a ventricular event sensing threshold 418, 428, or 438 applied to a selected one, two or all three of the accelerometer axis signals 410, 420, or 430, respectively, during the sensing window 416. In some examples, any two or all three axis signals 410, 420 and 430 may be combined by control circuit 206, e.g., by summing time-aligned sample point amplitudes of the filtered and rectified axis signals. The various operations performed by control circuit 206 for determining when AV block criteria are met as described herein, including setting a sensing window 416 and setting a ventricular event sensing threshold may be performed on the resulting signal determined as a combination of two or all three accelerometer axis signals 410, 420 and 430. The ventricular event sensing threshold, the selected axis signal (or combination of signals), and the sensing window starting and ending times may be AV block detection parameters that may be programmable by a user using external device 20.

In response to a ventricular event threshold crossing 414, 424, or 434 during the sensing window 416 by the respective accelerometer axis signal 410, 420 or 430, control circuit 206 detects the ventricular event and determines the associated atrial cycle to be an AV conduction cycle (labeled "AVC" 437). In some examples, the ventricular event sensing threshold may be set lower, even lower than the atrial event peak amplitude, and the number of sensing threshold crossings may be counted. When at least a threshold number of sensing threshold crossings is reached during the sensing window 416 or during an atrial cycle, the atrial cycle may be determined to be an AV conduction cycle by control circuit 206. The threshold number of sensing threshold crossings may be one, two, three, four or more and may include only positive-going crossings, only negative-going crossings or both positive and negative-going crossings.

Control circuit 206 may count an AV conduction cycle (or not count an AV block cycle) when at least one axis signal 410, 420 or 430 crosses the ventricular event threshold 418, 428 or 438 at least a threshold number of times during the sensing window 416. In other examples, control circuit 206 may require that at least two or all three axis signals and/or one or more combinations of two or all three axis signals cross a respective ventricular event threshold in order to detect the associated atrial cycle as an AV conduction cycle. Control circuit 206 may count the number of atrial cycles that AV conduction is not determined over a predetermined number of atrial cycles in some examples. Control circuit 206 may detect AV block when a threshold number of atrial cycles are associated with AV conduction not being determined (i.e., AV block cycles). In some examples, control circuit 206 may set an AV block or AV conduction (AVC) flag (shown as AVC labels 437) for each atrial cycle in a buffer in memory 210 to facilitate counting atrial cycles associated with AV conduction determinations and/or count AV block cycles. In the example of FIG. 400, the ventricular event sensing threshold is crossed during each sensing window 416 resulting in no AV block cycles and therefore AV block criteria are determined to be unmet by control circuit 206 for the atrial cycles shown.

In the example of FIG. 9, the ventricular event sensing threshold 418 is set to 75 ADC units for axis signal 410, and the ventricular event sensing thresholds 428 and 438 are set to 50 ADC units for axis signals 420 and 430. One ADC unit may correspond to 11.8 milli-g (where 1 g is the acceleration of gravity) and 100 milli-g may correspond to 1 $m/s^2$ acceleration. Accordingly a threshold of 50 to 75 ADC units may correspond to an acceleration of approximately 6 $m/s^2$ to approximately 9 $m/s^2$. In other examples, the ventricular event threshold may be between 3 $m/s^2$ and 10 $m/s^2$. The ventricular event sensing threshold may be selected for a given axis signal or combination of axis signals and may be set differently for different single-axis signals or combinations of axis signals when more than one single-axis signal and/or combination of axis signals are being monitored for detecting AV block.

The ventricular event sensing threshold may be set and periodically updated based on a maximum peak amplitude 415, 425 or 435 of one or more respective ventricular event signals 412, 422 or 432 that are sensed from a respective axis signal 410, 420 or 430. The ventricular event sensing threshold may be updated when AV conduction is being detected by control circuit 206 or AV conduction is confirmed by a user interacting with external device 20 of FIG. 1. When a combination of two or more axis signals 410, 420 and 430 is used for detecting AV block the applied sensing threshold for detecting ventricular event signals from the combination signal may be based on a maximum peak amplitude of the motion signal determined from the combination signal during known AV conduction.

In other examples, the threshold for detecting ventricular event signals may be set based on lower amplitude motion signals that are not intended to be detected, which may correspond to atrial contraction or other non-ventricular events. The motion signal may be filtered to attenuate the amplitude of lower amplitude signals that are not desired to be sensed. The amplitude of other non-ventricular event signals (such as atrial events or baseline noise) may be determined and the threshold may be set greater than the amplitude of non-ventricular event signals (but less than a peak amplitude of ventricular event signals).

The ventricular event sensing threshold 418, 428, or 438 may be set to a percentage of or a difference less than a mean maximum peak amplitude, median maximum peak amplitude, greatest maximum peak amplitude, least maximum peak amplitude, or a specified nth largest maximum peak amplitude of the motion signal that is determined by control circuit 206 over a specified number of atrial cycles when AV conduction is determined to be intact. For example, control circuit 206 may set the ventricular event sensing threshold to 50%, 60%, 70% or other selected percentage of a minimum (or lowest) maximum peak amplitude determined over 3, 6, 8, 10, 12 or other specified number of atrial cycles when AV conduction is determined to be intact. Furthermore, the ventricular event sensing threshold applied to a selected motion signal following sensed P-waves may be set uniquely from the ventricular event sensing threshold applied to the same motion signal following delivered atrial pacing pulses.

Control circuit 206 may be configured to determine an AV activation time 440 during one or more atrial cycles. The term "AV activation time" as used herein refers to the time from an atrial electrical event (sensed P-wave or atrial pacing pulse) to a selected feature or fiducial point of the ventricular event signal. In other examples, the AV activation time may be determined from an atrial event, electrical or mechanical (e.g., atrial event signal 421) to the next ventricular event, which may be the systolic event signal (e.g., signal 412) or the diastolic event signal (e.g., signal 421) in the motion signal. In the example of FIG. 9, control circuit 206 may determine the AV activation time 440 as the time from the P-wave sensed event signal 408 generated by sensing circuit 204 to the ventricular event sensing threshold crossing 414, 424 or 434 by the respective ventricular systolic event signal 412, 422 or 432 of a given axis signal 410, 420 or 430, respectively. A sensed AV activation time 440 may be determined separately following P-wave sensed event signals from a paced AV activation times determined following atrial pacing pulses.

Control circuit 206 may determine a trend of the AV activation time 440 over time to detect an increasing trend or prolongation of the AV activation time. An increasing or increased AV activation time may be an indication of disease progression of the conduction system. Accordingly, AV activation times may be determined on a beat-by-beat basis or on a sampled basis and a mean or median AV activation time may be determined from a specified number of atrial cycles, e.g., 6, 8 or more atrial cycles. An hourly, daily, or weekly mean or median AV activation time may be determined in various examples. In some examples, the AV activation time 440 is determined for a specified number of atrial cycles or over a specified time interval at one or more scheduled times of day or at predetermined time intervals. A mean or median AV activation time may be determined and compared to a previously determined mean or median AV activation time to determine a trend of AV activation times. If the AV activation time trend is determined to be increasing, e.g., an increase by more than a threshold percentage or specified difference from a previously determined AV activation time, AV block criteria may be determined to be met. An alert may be generated by control circuit 206 to notify a clinician of the increasing trend in AV activation time. An increasing trend in AV activation time may be detected by control circuit 206 in response to an AV activation time being greater than at least one previously determined AV activation time. An increasing trend in AV activation time, determined to meet AV block criteria, may be determined even when other AV block criteria based on a ventricular event metric(s) are unmet to enable control circuit 206 to generate a notification of a possible AV conduction abnormality or worsening condition.

In other examples, the AV activation times determined when AV block criteria are not met may be used in setting the starting time 413 and/or ending time 417 of sensing window 416. For example, a minimum, median or mean, and/or maximum AV activation time may be determined over a predetermined number of atrial cycles and used by control circuit 206 to adjust the sensing window 416. For instance, the starting time 413 may be adjusted to include the minimum AV activation time. The ending time 417 may be adjusted to include the maximum AV activation time. The sensing window 416 may be set to be centered on the mean or median AV activation time. The sensing window 416 may be set by control circuit 206 to a fixed duration or the duration may be adjusted (by adjusting the starting and/or ending times 413 and 417) to include at least a predetermined percentage of all of the AV activation times determined when the sensing window 416 is centered on the mean or median activation time.

FIG. 10 is diagram 450 of a cardiac electrical signal 452 and accelerometer axis signals 460, 470 and 480 that may be produced by pacemaker 14 during AV block. Cardiac electrical signal 450 is an atrial EGM signal produced by sensing circuit 204. Cardiac electrical signal 450 includes atrial P-waves 454 and asynchronous FFRWs 456 occurring at varying times during each atrial cycle 457 due to AV block. Each accelerometer axis signal 460, 470 and 480 is a rectified bandpass filtered signal, which may be produced by motion sensor 212 from each signal generated by a respective axis of a three dimensional accelerometer. Each accelerometer signal 460, 470 and 480 includes a ventricular systolic event signal 462, 472 and 482, respectively, following a FFRW 456.

Sensing circuit 204 generates a P-wave sensed event signal 458 in response to the cardiac electrical signal 452 crossing a P-wave sensing threshold 455. Control circuit 206 may set a ventricular event sensing window 466 in response to each P-wave sensed event signal 455, as described above in conjunction with FIG. 9. Control circuit 206 may apply the ventricular event sensing threshold 468, 478 or 488 to the respective accelerometer axis signal 460, 470 or 480 during the sensing window 466. As described above, a ventricular event sensing threshold may be applied to one, two or all three axis signals 460, 470 and 480 individually and/or to a combination of two and/or all three axis signals for detecting sensing threshold crossings. Control circuit 206 identifies an atrial cycle with no ventricular event sensing threshold crossing as an AV block cycle (AVB 485).

Control circuit 206 may identify an AV conduction cycle as any atrial cycle associated with a ventricular event sensing threshold crossing during the sensing window 466. As described above, an AV conduction cycle may be detected by control circuit 206 when at least one axis signal 460, 470 or 480 crosses the respective sensing threshold 468, 478 or 488 during the sensing window 466. In this example, an AV block cycle is identified when none of the axis signals (or a combination of axis signals) crosses the ventricular sensing threshold. In other examples, control circuit 206 may detect an AV conduction cycle when at least two or all three axis signals cross a respective ventricular event sensing threshold or a combination of at least two axis signals crosses a ventricular event sensing threshold. In this case, control circuit 206 may detect an AV block cycle as any atrial cycle during which at least one axis signal or a combination of two or more axis signals does not cross the respective ventricular sensing threshold.

Control circuit 206 may determine a ventricular event metric as a count of AV block cycles detected over the identified atrial cycles, as a percentage of AV block cycles out of the identified atrial cycles, or as a ratio of AV block cycles to the identified atrial cycles. To facilitate determination of when AV block criteria are met, control circuit 206 may set a flag in a buffer in memory 210 indicating AV block or AV conduction for each sensing window 466 (associated with each atrial cycle 457). For example, a first-in-first-out buffer in memory 210 may store an AVB flag or an AVC flag (shown as labels 485) for each atrial cycle of a predetermined number of atrial cycles, e.g., 6, 8, 10, 12 or other selected number of atrial cycles. After each atrial cycle 457, control circuit 206 may determine if a threshold number of AVB flags are stored in the buffer. The threshold number of AVB flags may be required to be consecutive in some examples but may be non-consecutive in other examples. In a first-in-first out buffer, the oldest AVB or AVC flag is cleared and a new flag is stored on the next atrial cycle. In other examples, the buffer may fill with AVB or AVC flags for a predetermined number of atrial cycles and then be cleared to store AVB or AVC flags for the next predetermined number of atrial cycles. Control circuit 206 may determine the ventricular event metric by counting the number of AVB cycles each time the buffer is filled, before clearing before the next predetermined number of atrial cycles.

Control circuit 206 may classify a sequence of atrial cycles as AV block in response to a threshold number of AVB flags being reached or exceeded in the buffer and increment an AV block detection counter in response to the AV block classification. When the AV block detection counter reaches a threshold, which may be one or more, AV block may be detected by control circuit 206 in response to AV block criteria being met. Control circuit 206 may generate an output in response to the AV block detection, which may include storing and subsequently transmitting an alert or notification and associated data and/or a therapy response.

In the examples of FIGS. 9 and 10, the motion signal feature used to detect an AV block cycle is based on the amplitude of the motion signal and in particular the amplitude of the motion signal being less than a ventricular event sensing threshold amplitude during a sensing window following each atrial electrical event. In other examples, control circuit 206 may determine one or more features of the motion signal during the sensing windows 416 and 466 for determining if a ventricular event is detected during the sensing window as evidence of AV conduction. For example, control circuit 206 may determine the maximum signal amplitude during the sensing window, the number of peaks, the signal width, the signal area, the maximum slope or other signal features or combinations of features. One or more features may be used to detect an AV block cycle for the associated atrial cycle. Control circuit 206 may determine one or more of these features to determine if the ventricular event signal is detected for determining a ventricular event metric at block 306 of FIG. 7 and at block 358 of FIG. 8.

In still other examples, an integral of the motion signal over each sensing window 416, 466 may be determined for identifying each atrial cycle as an AVB cycle or an AVC cycle. For example, control circuit 206 may sum the rectified sample point amplitudes of the motion signal over sensing window 416 or 466. Control circuit 206 may sum only sample point amplitudes exceeding a specified minimum threshold amplitude in some examples. The summation of the sample point amplitudes may be compared to a threshold value for discriminating between AV block and AV conduction for a given atrial cycle. For example, when the summed amplitudes are less than the threshold, an AVB flag may be set to count the associated cycle as an AVB cycle.

In another example, control circuit 206 may determine a count of sample points that exceed a specified minimum threshold amplitude in the rectified motion signal during a sensing window and compare the count to a threshold count for discriminating between AV block and AV conduction atrial cycles. When the sample point count is greater than the threshold, control circuit 206 detects the ventricular event in the sensing window, and the atrial cycle may be identified as an AV conduction cycle. When the sample point count is less than the threshold, control circuit 206 detects an AV block cycle. The count of AV block cycles or a ratio of AV block cycles to AV conduction cycles may be determined as the ventricular event metric that is compared to AV block detection criteria by control circuit 206.

As described above in conjunction with FIG. 9, control circuit 206 may determine the AV activation time 490 as the time from the P-wave sensed event signal 458 generated by sensing circuit 204 (or from an atrial pacing pulse) to the ventricular event sensing threshold crossing by the motion signal, as shown by axis signal 460 in the example of FIG. 10. Variability of the AV activation time 490 and/or an increasing trend in the AV activation time 490 may be determined by control circuit 206 for determining when AV block criteria are met.

Figure 11:
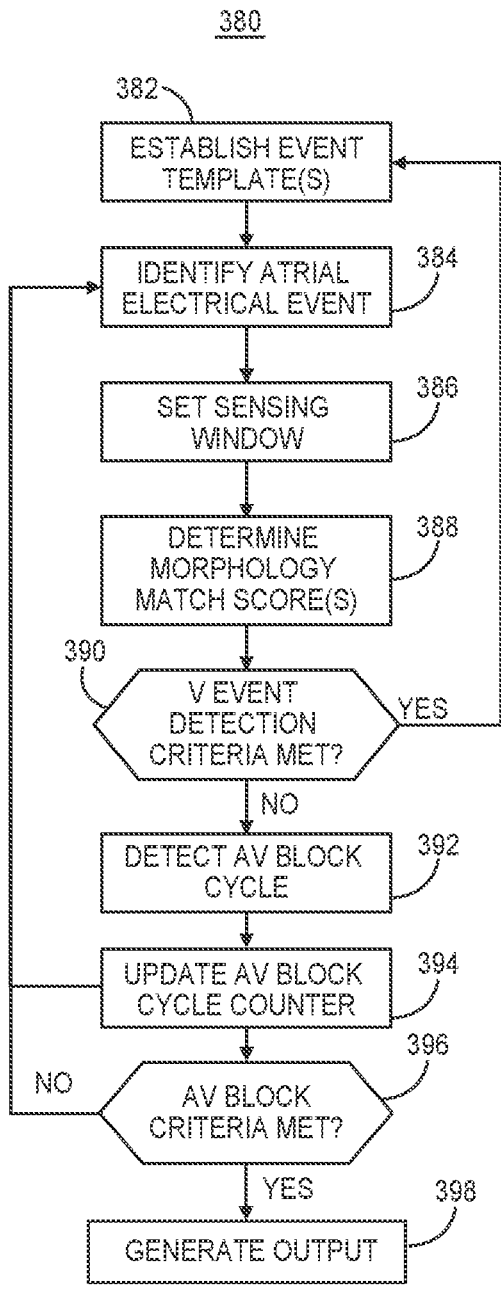
FIG. 11 is a flow chart of a method that may be performed by a medical device for detecting ventricular events according to another example.

FIG. 11 is a flow chart 380 of a method that may be performed by a medical device for discriminating between AV block atrial cycles and AV conduction atrial cycles according to another example. Control circuit 206 may perform morphological analysis of the motion signal waveform for determining if a ventricular event is within a sensing window set in response to an atrial electrical event, e.g., sensing windows 416 and 466 of FIGS. 9 and 10. Control circuit 206 may establish a ventricular event morphology template at block 382 during known AV conduction. Telemetry circuit 208 may receive a command from a user confirming AV conduction. In other examples, control circuit 206 may detect AV conduction based on a 1:1 ratio of atrial electrical events and ventricular event sensing threshold crossings during the sensing windows 416 as shown in FIG. 9.

Additionally, control circuit 206 may establish one or more P-wave morphology metrics or features at block 382. For example, control circuit 206 may establish a P-wave template at block 382 from the cardiac electrical signal. One P-wave template may be established that corresponds to intrinsic P-waves, and another P-wave template may be established that corresponds to pacing-evoked P-waves in some examples. The P-wave template(s) may be established during known AV conduction. In other examples, one or more features of the intrinsic and/or pacing-evoked P-waves may be determined as a morphology feature of a normal P-wave. Such features may include a maximum peak amplitude, a P-wave width, a maximum P-wave slope, a number of signal peaks, a P-wave area or other distinguishing feature or combination of features of a true P-wave signal. During AV block, the FFRW signal may occur at the same time as or overlapping with the P-wave in the atrial EGM signal such that the P-wave morphology is altered compared to normal P-waves. The P-wave template and/or one or more P-wave morphology features may be established by control circuit 206 from the cardiac electrical signal over a P-wave morphology window that includes the time of a P-wave sensed event signal. The pacing-evoked P-wave template may be established by setting a P-wave morphology window in response to the atrial pacing pulse delivery.

The ventricular and/or atrial event morphology template(s) may be established by control circuit 206 at block 382 using wavelet transform techniques in some examples. Wavelet transform coefficients may be determined from the motion signal during the sensing window, e.g., using a Haar wavelet transform method. The digitized averaged motion sensor signal and/or the associated wavelet transform coefficients may be stored in memory 210 as the ventricular event morphology template. The digitized average P-wave signal and/or the associated wavelet transform coefficients may be stored in memory 210 as the P-wave morphology template (for intrinsic and/or paced events). In other examples, the morphology template(s) may be generated from the wavelet transform of a time averaged signal acquired during confirmed AV conduction. The time averaged signal may be determined by determining an ensemble average of the motion signal (or electrical signal for the P-wave templates) from multiple morphology sensing windows. The ensemble average may be obtained by averaging the signal within the window over the duration of multiple sensing windows or aligning each event signal in time based on a fiducial point of the event (ventricular event or P-wave), such as a threshold crossing or maximum peak amplitude, and averaging the time-aligned signals. The processing performed to generate the ventricular event morphology template and optionally the P-wave morphology template(s) and compare an unknown signal to the respective morphology template may include other techniques in the time domain or transformation techniques other than the wavelet transform method.

After establishing a ventricular event template during known AV conduction, control circuit 206 may begin monitoring for AV block. At block 384, control circuit 206 identifies an atrial cycle by identifying an atrial electrical event and sets the ventricular event sensing window at block 386. Control circuit 206 determines a morphology match score at block 388. For example, the morphology match score may be determined by performing a wavelet transform on the motion signal during the ventricular event sensing window to generate a set of wavelet coefficients. The wavelet coefficients may have predetermined weightings representative of the amplitudes of the frequency components of the signal waveform. These wavelet coefficients may be compared to the wavelet coefficients established for the ventricular event template to determine the morphology match score.

The morphology match score represents the correlation between the wavelet coefficients of the ventricular event template corresponding to known AV conduction and the wavelet coefficients of the unknown waveform present in the sensing window, which may be aligned with the template based on a predetermined fiducial point such as a maximum sample point amplitude or the starting time of the sensing window and spanning the sensing window. The morphology match score may be determined using various template or morphology matching techniques for determining correlation between the established ventricular event template and the motion signal during unknown AV conduction status. Such techniques may include various waveform correlation analyses, determination of multiple fiducial points or characteristics of the motion signal waveform during the sensing window such as area of the rectified signal during the sensing window, maximum peak amplitude, number of peaks or zero crossings (prior to rectification), inflection points, peak slopes, etc.

In some examples, at block 388 control circuit 206 may determine the morphology match score between the unknown cardiac electrical signal during an atrial morphology window and the P-wave template, corresponding to a sensed intrinsic P-wave or paced atrial cycle. In this case, a high morphology match score indicates a true P-wave. A low morphology match score may indicate a FFRW occurring concomitantly with the P-wave, which may occur during $3^{rd}$ degree AV block, for example. When this occurs, the subsequent ventricular event signal following the FFRW may appear to be synchronized to the P-wave presenting false evidence of AV conduction. As such, detection of a low P-wave morphology match score or low match of other P-wave morphology features to reference P-wave morphology features, even when the ventricular event morphology match score determined from the motion signal is high, may be evidence of AV block. Detection of a low P-wave morphology match score based on the atrial EGM signal when ventricular event morphology is detected from the motion signal may be used by control circuit 206 to discriminate between different types of AV block and/or more accurately track the frequency and duration of long ventricular pauses (when no ventricular event signals are present based on one or more ventricular event metrics).

At block 390, control circuit 206 compares the ventricular event morphology match score and may compare the P-wave morphology match score and any other determined motion signal features and/or P-wave signal features to ventricular event detection criteria. The ventricular morphology match score may be required to exceed a threshold value in order to detect the ventricular event within the ventricular event sensing window. For example, if the morphology match score has a possible range of 0 to 100, the match threshold may be 50, 60, 70 or other threshold value. The P-wave morphology match score may also be required to exceed an atrial event matching threshold to verify that a FFRW is not coincident with the P-wave, e.g., less than 60, 50, 40, 30 or other selected threshold. In other examples, control circuit 206 may compare the P-wave morphology match score and/or one or more cardiac electrical signal morphology features to established P-wave reference values. When the determined match score and/or cardiac electrical signal features determined from a P-wave morphology window do not match the reference values, control circuit 206 may detect an altered P-wave morphology.

When the ventricular event morphology match score is greater than a threshold score and an altered P-wave morphology is not detected, and any other determined motion signal features satisfy the ventricular event detection criteria, AV conduction is determined to occur for that atrial cycle. AV block is not detected for that cycle. In some examples, control circuit 206 may return to block 382 to update the ventricular electrical event template (and optionally the P-wave template) based on the detected ventricular event associated with AV conduction. Control circuit 206 may use the ventricular event signal detected at block 390 to update the template at block 382. Control circuit 206 may use the P-wave signal to update the associated intrinsic or paced P-wave template. The template(s) may be updated each time an AV conduction cycle is detected or periodically on a scheduled basis. When a template update is not scheduled, control circuit 206 may return to block 384 to identify the next atrial cycle to continue monitoring for AV block cycles.

When the ventricular event morphology match score or other motion signal features do not meet the ventricular event detection criteria at block 390, control circuit 206 detects an AV block cycle at block 392. In some examples, when the ventricular event morphology match score is greater than a match threshold score and an altered P-wave morphology is detected, control circuit 206 may determine that ventricular event detection criteria are met at block 390. When ventricular event detection criteria are not met at block 390, control circuit 206 detects an AV block cycle at block 392. Control circuit 206 may set an AV block flag in a buffer in memory 210 or update an AV block counter at block 394. The AV block detection for the atrial cycle based on the morphological analysis and/or other motion signal features during the sensing window may be used by control circuit 206 to determine when criteria are met for detecting an AV block episode (block 396) and generating an AV block output (block 398).

The AV block episode may be detected based on criteria of a threshold number of consecutive AV block cycles being detected at block 396, indicating a long ventricular pause, e.g., three consecutive AV block cycles or more. The threshold number of AV block cycles required to detect an AV block episode manifesting as a long ventricular pause may be set based on the atrial rate. For example, if the atrial rate is 60 beats per minute, control circuit 206 may set the threshold of at least three consecutive AV block cycles required to detect a ventricular pause corresponding to AV block that is at least 3 seconds long. When the atrial rate is 100 beats per minute, control circuit 206 may set the threshold number of AV block cycles to at least five consecutive AV block cycles to detect an AV block episode of at least three seconds. An AV block episode may be detected by control circuit 206 at block 396 when non-consecutive AV block cycles occur as threshold percentage or frequency out of a predetermined number of atrial cycles in some examples. When a threshold number of AV block episodes are detected (one or more), the duration of one or more AV block episodes reaches a threshold duration, an increasing trend of AV block episode frequency and/or duration, or other metric of AV block severity meets AV block criteria for providing a response to the detected AV block, control circuit 206 may generate a response at block 398 according to any of the examples provided herein, such as an alert or notification, determination of total time in AV block, storage of cardiac signals, and/or adjusting a therapy according to any of the examples given above.

Figures 12, 13:
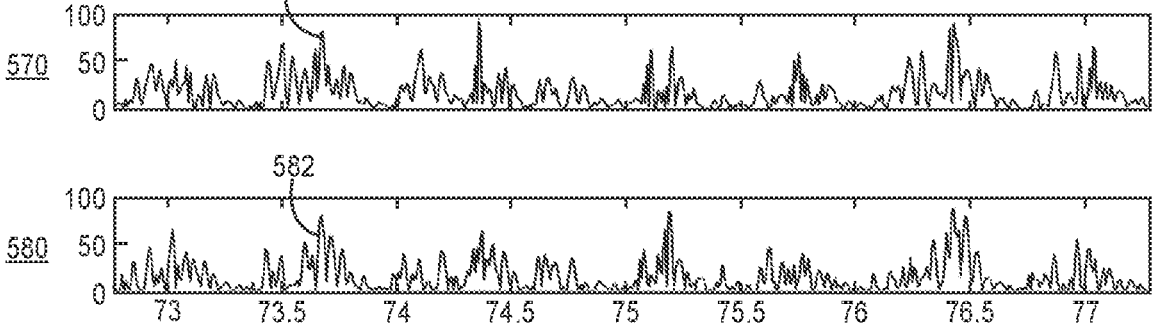
FIG. 12 is a diagram of cardiac signals that may be sensed by a pacemaker in another example.
FIG. 13 is a diagram of a cardiac electrical signal and accelerometer axis signals during AV block.

FIG. 12 is a diagram 500 of cardiac signals that may be sensed by pacemaker 14 in another example. Cardiac electrical signal 502 sensed by sensing circuit 204 includes atrial P-waves 504, each followed by an FFRW 506. Each accelerometer axis signal 510, 520 and 530 produced by a three-dimensional accelerometer included in motion sensor 212 is bandpass filtered and rectified by motion sensor 212 and passed to control circuit 206. Each axis signal 510, 520, and 530 includes ventricular systolic event signals 512, 522 and 532, respectively, each following an FFRW 506. In the example of FIG. 10, AV conduction is intact such that each atrial P-wave 504 is conducted to the ventricles as evidenced by the FFRW 506 that follows each P-wave 504 and the subsequent mechanical contraction of the ventricles as evidenced by the ventricular systolic event signals 512, 522 and 532 following each P-wave 504.

Sensing circuit 204 generates a P-wave sensed event signal 508 in response to sensing each P-wave 504, e.g., in response to the cardiac electrical signal 502 crossing a P-wave sensing threshold 505. In some examples, control circuit 206 is configured to identify the maximum peak amplitude 514 of a motion sensor signal following each P-wave sensed event signal 508 (and before the next P-wave sensed event signal or atrial pacing pulse). While intrinsic P-waves 504 are shown to be sensed on each atrial cycle in the example of diagram 500, it is to be understood that control circuit 206 may identify the maximum peak amplitude of a motion sensor signal following each atrial electrical event, sensed P-wave or atrial pacing pulse. In the illustrative example, control circuit 206 uses the first accelerometer axis signal 510 for monitoring for AV block. In this example, the maximum peak amplitude 514 is identified from accelerometer axis signal 510 during each atrial cycle identified based on receiving a P-wave sensed event signal 508 (or atrial pacing pulse during a paced atrial rhythm). In other examples, the operations performed as described with reference to axis signal 510 may be performed on any one, two or all three of the axis signals 510, 520 or 530, concurrently in parallel operations or sequentially. In other examples, any two or all three axis signals 510, 520 and 530 may be combined by control circuit 206, e.g., by summing time-aligned sample point amplitudes of the filtered and rectified signals. The operations performed for determining when AV block criteria are met may be performed on the resulting signal determined as a combination of two or all three axis signals 510, 520 and 530.

Control circuit 206 may determine the amplitude 518 of each identified maximum peak 514. Additionally or alternatively, control circuit 206 may determine the time interval 516 from each P-wave sensed event signal 508 (or atrial pacing pulse) associated with the start of the atrial cycle to the subsequent maximum peak amplitude 514 (before the next atrial electrical event). The time intervals 516 between each atrial electrical event and the motion signal maximum peak may be analyzed by control circuit 206 for determining a ventricular event metric and detecting AV block. In FIG. 12, the time intervals 516 may be referred to as AV activation time since they are the time from an atrial electrical event until mechanical activation (contraction) of the ventricles. In some examples, control circuit 206 may compare the AV activation time 516 to a threshold activation time for detecting AV block on a given atrial cycle. Control circuit 206 may compare the AV activation time determined for each identified atrial cycle to an upper threshold activation time interval 507. Any AV activation time longer than the upper threshold activation time interval 507 indicates an AV block cycle. In some examples, control circuit 206 may compare the AV activation times to a lower threshold. Any AV activation time less than the lower threshold activation time interval suggests a non-conducted ventricular event and dyssynchrony between the atrial electrical event and the ventricular event as evidence of an AV block cycle. When the AV activation time 516 is greater than the upper threshold time interval 507 or less than a lower threshold time interval, control circuit 206 may determine that AV block is present for that atrial cycle. In some examples, a different upper threshold activation time interval and/or lower threshold activation time interval may be set following a sensed intrinsic P-wave than following a delivered atrial pacing pulse. The AV electrical conduction time (e.g., from the P-wave to a FFRW) and therefore the AV activation time may be different following an intrinsic P-wave than following an atrial pacing pulse. Control circuit 206 may determine a ventricular event metric by counting the atrial cycles identified as AV block cycles (having an AV activation time outside a threshold range) over a predetermined number of identified atrial cycles. If the AV block count reaches a threshold count, control circuit 206 may detect AV block. The AV block counter may be reset or cleared after a predetermined number of atrial cycles or when a threshold number of atrial cycles occur without an AV block determination.

In other examples, control circuit 206 may determine the ventricular event metric by determining one or more metrics of the AV activation times determined over a predetermined number of atrial cycles. Control circuit 206 may determine at least one AV activation time metric that is correlated to the variability or other measure of spread of the AV activation times determined over the predetermined number of atrial cycles. Additionally or alternatively, control circuit 206 may determine at least one AV activation time metric corresponding to the average or other measure of center of the AV activation times determined over the predetermined number of atrial cycles. As examples, with no limitations intended, control circuit 206 may determine the maximum AV activation time, the minimum AV activation time, the average AV activation time, the median AV activation time, the range of the AV activation times, a sum, average or range of successive differences between successive AV activation times, a sum, average or range of the differences between each AV activation time and the maximum, minimum, average or other selected reference AV activation time, or any combination thereof. Control circuit 206 may compare one or more of these AV activation time metrics to criteria for detecting AV block for the predetermined number of atrial cycles. For example, when the AV activation time range exceeds a threshold range, AV block may be detected.

In the illustrative example of FIG. 12, the average AV activation time is 260 milliseconds with a range of 40 milliseconds and standard deviation of 20 milliseconds. As can be observed in FIG. 12, each AV activation time 516 is similar in duration such that the range, standard deviation, and any sum of differences between successive AV activation times will be relatively small. Control circuit 206 may compare these or other metrics of AV activation time to AV block criteria. For example, the average AV activation time may be compared to a threshold activation time and the range may be compared to a threshold range. When the average AV activation time is less than a threshold AV activation time associated with normal AV conduction, e.g., less than 300 ms, and the range is less than a threshold range associated with normal AV conduction, e.g., less than 60 ms, AV block criteria are not met and AV block is not detected by control circuit 206. Control circuit 206 may compare one or more AV activation time metrics corresponding to central tendency and/or spread to AV block criteria for detecting AV block over the predetermined number of atrial cycles.

FIG. 13 is a diagram 550 of a cardiac electrical signal 552 and accelerometer axis signals 560, 570 and 580 during AV block. Cardiac electrical signal 552 includes P-wave signals 554 and FFRWs 556 that occur asynchronously with the P-wave signals 554. Sensing circuit 206 generates a P-wave sensed event signal 558 in response to sensing each P-wave signal 554. Motion sensor 212 produces filtered, rectified accelerometer axis signals 560, 570 and 580, each including ventricular systolic event signals 562, 572 and 582, respectively, corresponding to ventricular contractions. As described above, control circuit 206 may be configured to identify the maximum peak amplitude 564 of a motion signal (axis signal 560 in the example of FIG. 13) following each atrial electrical event (each P-wave sensed event signal 558 and each atrial pacing pulse when present). The maximum peaks of one, two or all three axis signals 560, 570 and/or 580 may be determined or the maximum peak of a combination of two or all three axis signals may be determined by control circuit 206. Criteria for detecting AV block may be applied to each axis signal 560, 570 and 580 and when at least one signal meets the AV block criteria, AV block may be detected by control circuit 206. In other examples, at least two signals may be required to meet AV block criteria in order for an AV block detection to be made over a predetermined number of cycles.

The amplitude 565 of each identified maximum peak 564 may be determined by control circuit 206 in some examples. Additionally or alternatively, the AV activation time 566 between each atrial electrical event and the subsequent maximum peak amplitude 564 of the motion signal during the atrial cycle (before the next atrial electrical event) may be determined by control circuit 206.

In some examples, control circuit 206 may compare each AV activation time determined for each atrial cycle to an AV block detection threshold time interval or range. As observed in FIG. 13, the AV activation times 566, 567, 568 and 569 are variable, with a very short AV activation time 569, which may be shorter than a lower AV activation time threshold and evidence of an asynchronous ventricular event, and a very long AV activation time 567, which may be longer than an upper AV activation time threshold and evidence of AV block. Each AV activation time 566, 567, 568 and 569 may be compared to a threshold AV activation time 555 or an AV activation time range including upper and lower limits on a beat-by-beat basis for counting atrial cycles identified as AV block cycles having an AV activation time outside the AV activation time range. When a threshold count of AV block cycles is reached, e.g., 2 AV block cycles out of 6 atrial cycles or 2 AV block cycles out of 8 atrial cycles or other specified criteria, control circuit 206 may determine that AV block criteria are met and detect AV block.

In other examples, the AV activation times may be determined for each atrial cycle and one or more AV activation time metrics (related to central tendency and/or spread as described above) may be determined by control circuit 206 as a ventricular event metric for comparison to AV block criteria. In the example of FIG. 13, the average AV activation time is 320 ms with a range of 430 ms and standard deviation of 160 ms. In this example, the average AV activation time is greater than a threshold activation time of 300 ms, as an example, corresponding to normal AV conduction. The large range of 430 ms is indicative of large variability of the AV activation time indicating AV dyssynchrony. An AV activation time range greater than a range threshold may meet AV block criteria. As such, in various examples, control circuit 206 may detect AV block for atrial cycles over which the AV activation time metric(s) is(are) representative of a long average AV activation time and/or large range and/or large standard deviation or other measure of variability of the AV activation times, such as a coefficient of variation, the mean of the absolute differences between AV activation times or the like.

Control circuit 206 may compare the amplitude 565 of each identified maximum peak 564 to AV block criteria in some examples. Variation in the maximum amplitude of the peak acceleration during ventricular contraction may occur with differences in ventricular volume and pressure that may occur when the ventricles do not contract during an atrial cycle, in a 1:1 ratio with atrial cycles, or at varying times during the atrial cycles. In some examples, the maximum amplitude 565 may be compared to a ventricular event threshold amplitude to verify that the maximum peak corresponds to a ventricular event signal and not another motion signal. To illustrate, in FIG. 13, the AV activation time 568 may not be a true activation time because the maximum peak amplitude 565 ending AV activation time 568 is very low and does not follow an FFRW signal 556. As such, control circuit 206 may use criteria such as the amplitude 565 of the maximum acceleration signal peak for verifying an AV activation time.

For example, the amplitude of each maximum peak may be compared to a threshold amplitude, which may be based on one or more maximum peak amplitudes determined when AV conduction is known, e.g., based on one or more maximum peak amplitudes 518 determined during the atrial cycles shown in FIG. 12. The maximum peak threshold may be set by control circuit 206 to a percentage, e.g., 40%, 50%, 60%, 65%, 70%, 75% or other percentage of the maximum peak amplitude determined when no AV block is detected. The AV activation times 566, 567, 568 and 569 may be determined by control circuit 206 when the associated maximum peak has an amplitude greater than the maximum peak threshold. Control circuit 206 may ignore AV activation time 568 in this example or set the AV activation time 568 to a maximum AV activation time (e.g., greater than a threshold activation time interval for detecting AV block) when the associated maximum peak has an amplitude less than the maximum peak threshold. The range or variability or other metrics of the amplitudes 565 of the maximum peaks of the motion signal may be used alone or in combination with the AV activation time metric(s) for detecting AV block over the identified atrial cycles.

Figure 14:
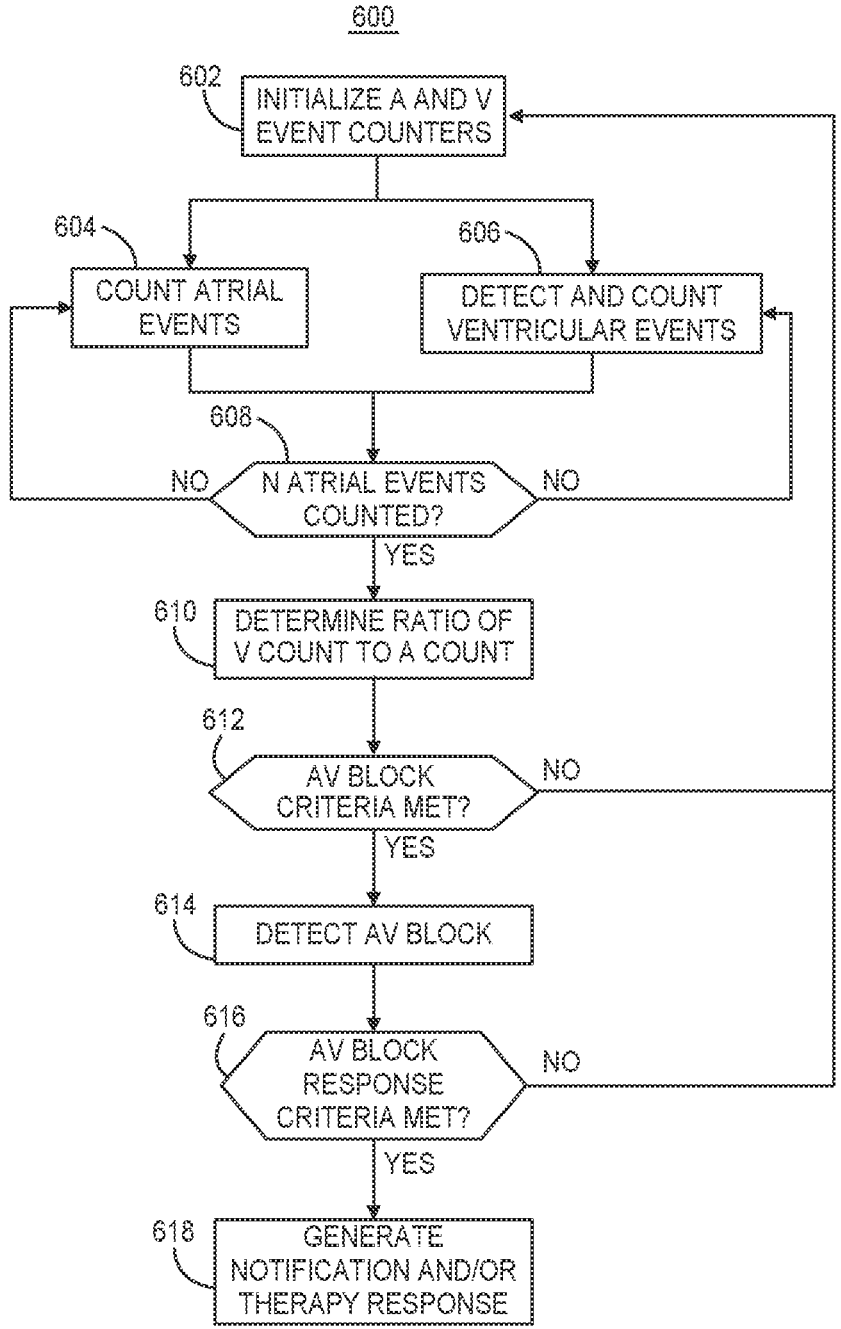
FIG. 14 is a flow chart of a method performed by a pacemaker for detecting AV block according to another example.

FIG. 14 is a flow chart 600 of a method performed by pacemaker 14 (or 254) for detecting AV block according to another example. In the examples of FIGS. 9-10, a ventricular event sensing window is set in response to each atrial electrical event. When a ventricular event is not detected during the sensing window, AV block is determined to occur during the associated atrial cycle. AV block criteria may be set based on the percentage or frequency of AV block cycles. In other examples, a ventricular event sensing window is not required. Ventricular events may be detected from the motion signal and the number of ventricular events (or a corresponding ventricular rate or ventricular rate interval) may be compared to the number of atrial cycles (or a corresponding atrial rate or atrial rate interval) over which the ventricular events are detected. When less than a 1:1 ratio exists between ventricular events and atrial cycles, in other words when the ventricular event rate is less than the atrial rate, AV block may be detected by control circuit 206.

At block 602 of FIG. 14, control circuit 206 may initialize atrial and ventricular event counters. The atrial event counter may be set to zero and as atrial electrical events are identified (sensed P-waves and delivered atrial pacing pulses) the atrial event counter may count up to a predetermined number N at block 604. Alternatively, the atrial event counter may be set to the predetermined number N and count down by 1 each time a P-wave sensed event signal is received from sensing circuit 204 or an atrial pacing pulse is delivered by pulse generator 202.

Control circuit 206 may initialize the ventricular event counter to zero at block 602 and count up by one each time a ventricular event is detected from the motion signal at block 606. The ventricular events may be detected in response to a ventricular event sensing threshold crossing by the motion signal. For example, a positive-going crossing of the sensing threshold may be counted as one ventricular event. A post-ventricular blanking period may be applied after the positive-going crossing to prevent the same ventricular event from being counted more than once. The post-ventricular blanking period may be a 100 to 200 ms time interval, e.g., 120 ms to 150 ms, during which any additional sensing threshold crossings are not counted as ventricular events.

At block 608, control circuit 206 may determine when a predetermined number (e.g., 3, 4, 6, 8, 10, 12, 16 or other selected number) of atrial events (or atrial cycles) have been counted. If N atrial events have not yet been counted, control circuit 206 continues to count atrial events at block 604 and ventricular events at block 606 until the predetermined number of atrial events has been counted. When N atrial events are counted, control circuit 206 determines the ratio of the ventricular event count to the number of atrial events counted at block 610. Control circuit 206 compares the ratio to AV block criteria at block 612. When the ratio is 1:1, AV block is not detected. When the ratio is less than 1:1, AV block may be detected for the predetermined number of atrial cycles. In some examples, a ratio that is slightly less than 1:1 may not result in an AV block detection to allow for slight variation in ventricular event amplitude that may lead to occasional undersensing of the ventricular event, the occurrence of a premature ventricular contraction which may be followed by a long pause, or other variations in the sensed ventricular rate unrelated to AV block. For instance, when the ventricular event count is one or two less than the atrial event count, AV block may not be detected by control circuit at block 612.

A fixed number of atrial events N may be counted for detecting when the ventricular rate is less than the atrial rate. As such, instead of determining a ratio at block 610, control circuit 206 may compare the ventricular event count to a threshold count set based on N, the fixed number of atrial events, for determining when AV block criteria are met at block 612. The threshold may be set equal to N, equal to N−1, equal to N−2, or to a percentage of N, e.g., 80% to 100% of N. When the ventricular event count is less than the threshold count, control circuit 206 determines that the AV block criteria are met at block 612.

In other examples, the control circuit 206 may count atrial event and ventricular events over a predetermined detection time interval, e.g., 10 seconds, 20 seconds, 30 seconds, one minute, two minutes or other selected time interval. In this case the number of atrial events will vary with atrial rate. Control circuit 206 may start the time interval at block 602 when the atrial and ventricular event counters are initialized and determine when the time interval is expired at block 608 (instead of determining that N atrial events have been counted). When the detection time interval expires, control circuit 206 determines the ratio (at block 610) of the number of ventricular events counted to the number of atrial events counted over the predetermined time interval. The ratio is compared to AV block criteria at block 612.

When AV block criteria are unmet for the predetermined number of atrial events (or the predetermined time interval), control circuit 206 returns to block 602 to re-initialize the event counters and repeat the process of counting atrial events and ventricular events. When control circuit 206 determines that the AV block criteria are met at block 612, AV block may be detected at block 614 for the predetermined number of atrial events (or predetermined time interval including the counted atrial events). Control circuit 206 may determine if AV block response criteria are met at block 616. In some examples, control circuit 206 may generate an output in response to each time AV block criteria are met at block 618. In other examples, control circuit 206 may determine that AV block response criteria are met when AV block criteria are met a threshold number of times. AV block may be required to be detected for the predetermined number of atrial cycles (or detection time intervals) a threshold number of times before control circuit 206 generates an output. For instance, the AV block response criteria may be met when the AV block criteria are met for two consecutive sets of N atrial cycles or two consecutive detection time intervals. In other examples, at least two out of three, three out of four or other X out Y sets of N atrial cycles (or N predetermined time intervals) may be required to detected as AV block in order to meet the AV block response criteria at block 616. The sets of N atrial cycles or N predetermined time interval may or may not be required to consecutive AV block detections.

When the AV block response criteria are unmet, control circuit 206 may return to block 602 without providing a response other than to count or flag the AV block detection. When AV block response criteria are met, control circuit 206 may generate an output at block 618, which may include generating a notification or alert that is transmitted by telemetry circuit 208. The output may include generating a cumulative AV block metric. For example, control circuit 206 may update the number of AV block detections determined over a 24 hour or other time period to provide a metric of how much time or what percentage of the time the patient is experiencing AV block. In some examples, a daily cumulative AV block metric may be determined and stored in memory 210. Additionally or alternatively, the cumulative AV block metric may be updated after each AV block detection to track the total time that the patient has experienced AV block since implantation of the pacemaker 14 (or 254).

The response generated at block 618 may include a therapy adjustment response in some examples. For instance, the atrial pacing rate may be decreased by control circuit 206 in an attempt to promote 1:1 AV conduction. In other examples, ventricular pacing (e.g., via the His bundle) may be enabled to provide ventricular rate support when ventricular pacing capabilities are included in the pacemaker 14 (or 254). Any other examples described herein of outputs that may be generated by control circuit 206 in response to AV block criteria being met may be performed at block 618, including AV block related data storage and atrial EGM and/or motion signal episode storage.

FIG. 15 is a flow chart 700 of a method performed by a medical device, e.g., pacemaker 14 or pacemaker 254, for detecting AV block according to another example. At block 701, control circuit 206 may establish an AV block criteria. As described below, control circuit 206 may be configured to determine one or more integration metrics from the motion signal over a detection time interval. The integration metric(s) determined over the detection time interval may be compared to the AV block criteria for detecting AV block. For example, a ventricular event threshold may be set at block 701 that is applied to one or more integration metrics determined over the detection interval. The ventricular event threshold may be a programmable or default value stored in memory 210. In other examples, control circuit 206 may establish the ventricular event threshold based on the motion signal. In order to establish the ventricular event threshold at block 701, control circuit 206 may determine a baseline integration metric of the motion signal during known AV conduction. For example, when pacemaker 14 is initially implanted, it is expected that the patient is not experiencing AV block and being treated for SA node dysfunction by atrial pacing only as needed.

During this initial post-implant time period, or when AV conduction is confirmed by a user, control circuit 206 may determine the integration metric from the motion signal, using techniques described below. The integration metric may be determined during a detection time interval when conditions for AV block monitoring are met but AV conduction is highly likely to be intact (such as just after pacemaker implant). For example, AV block monitoring conditions may require that the atrial rate be less than a threshold rate, e.g., less than 100 beats per minute, and/or require that a patient physical activity metric be below an activity threshold. The integration metric may be determined by control circuit 206 over multiple integration intervals, multiple times per hour or multiple times per day, for one or more days, over one week, over two weeks, or over another selected time period. The ventricular event threshold may be set based on a percentage of the mean, median, or selected percentile of the integration metrics determined during periods that AV conduction is highly likely. To illustrate, the ventricular event threshold may be set to the fifth percentile of the integration metrics determined, to the lowest integration metric determined or to a percentage of the lowest integration metric, e.g., 80%, 90%, 100%, 110% or other selected percentage of the lowest integration metric.

In this way, the ventricular event threshold is set to a level at or below which ventricular activity is absent or diminished as an indication of AV block. An integration metric greater than the ventricular event threshold indicates ventricular activity consistent with AV conduction. The ventricular event threshold may also be referred to as a ventricular activity threshold, ventricular motion threshold or cardiac motion threshold as it is used to discriminate between ventricular motion during AV conduction and ventricular motion during AV block.

At block 702, control circuit 206 may start monitoring for AV block by setting a predetermined detection time interval, which may be started at a time that is independent of the timing of atrial events. The detection time interval may not be sensing window started in response to an atrial event that is intended to encompass a single ventricular event. Rather, the detection time interval may be started anytime relative to an atrial event or cycle and is set to a duration intended to encompass multiple atrial cycles in some examples. The detection time interval may be at least one second long. The detection time interval may be 2, 3, 4, 5, 10, 20, 30, or 60 seconds long as other examples. As indicated above, the detection time interval may be started only when AV block monitoring conditions are met, which may include specified times of day, specified heart rates, specified physical activity levels, and/or specified patient posture.

During the detection time interval, control circuit 206 determines a ventricular event metric at block 704 by determining at least one integration metric of the motion signal (which may be a single axis signal or combination of axis signals). The integration metric may be determined as a summation of sample points of the rectified, filtered signal throughout the duration of the detection time interval. In other examples, multiple integration metrics may be determined over the duration of the detection time interval with each integration metric being determined over one integration interval that is a portion of the detection time interval. The sample points that are summed for determining the integration metric may be only the sample points greater than a predetermined threshold amplitude or may be all sample points spanning the integration interval. In other examples, control circuit 206 may determine the integration metric by counting the number of sample points that are greater than a predetermined threshold amplitude over the duration of each integration interval.

During the detection time interval, control circuit 206 may also identify and count atrial cycles at block 706 in some examples. Control circuit 206 may count atrial cycles by counting each sensed P-wave and each delivered atrial pacing pulse, where each atrial event is associated with the start of an atrial cycle. In some examples, control circuit 206 may optionally set an atrial blanking window following each identified atrial event at block 708. The atrial blanking window may be set to extend from the atrial electrical event to 50 to 100 ms after the atrial electrical event. The atrial blanking window may be set to blank the motion signal during the atrial contraction so that motion signal peaks due to atrial contraction do not contribute to the integration metric. Sample points during the atrial blanking window may be ignored by control circuit 206 and not counted or summed for determining the integration metric. In other examples, no atrial blanking windows are required and all sample points spanning the integration interval may be used in determining the integration metric.

At block 710, control circuit 206 may determine if the detection time interval expires. Prior to expiration, control circuit 206 may continue to identify and count atrial events and continue determining the integration metric(s) over each integration interval during the detection time interval. When the detection time interval expires at block 710, control circuit 206 may determine a normalized integration metric at block 712, in some examples. The normalized integration metric may be determined as the integration metric divided by the number of atrial cycles counted during the corresponding integration interval. In other examples, counting of atrial cycles is optional. The integration metric may be determined without normalizing by the number of atrial cycles. For example, when the integration metric is determined over multiple integration intervals during a detection time interval, each integration metric may be determined without normalizing by the number of atrial cycles. An example method for determining multiple integration intervals over a detection time interval is described below in conjunction with FIG. 17.

At block 714, control circuit 206 compares the normalized integration metric (or non-normalized integration metric) to AV block criteria. When one or more ventricular events occur within an integration interval, the integration metric, which may be normalized by the number of atrial cycles during the integration interval, is expected to be greater than a ventricular event detection threshold value since the relatively large amplitude ventricular event signals in the motion signal are expected to be present for each one of the atrial events. When an integration metric, which may be normalized by the number of atrial cycles during the integration interval, is less than ventricular event threshold value, ventricular event signals may be absent during the integration interval due to AV block. When the integration metric is equal to or greater than the ventricular event threshold, evidence of at least one ventricular event signal during the integration interval may be evidence that AV conduction is occurring during the integration interval. As such, when control circuit 206 determines that the integration metric does not meet ventricular event detection criteria, e.g., by being less than a predetermined ventricular event threshold value, control circuit 206 may determine AV block criteria are met at block 714 for the detection time interval (and associated atrial cycles occurring during the detection time interval). AV block may be detected at block 716 in response to the AV block criteria being met. When multiple integration intervals define the detection time interval, a threshold number of the integration metrics determined during the detection time interval may be required to be less than the ventricular event threshold at block 714 to meet AV block criteria. When the AV block criteria are unmet at block 714, control circuit 206 may return to block 702 to start the next detection time interval, which may follow consecutively without delay or be started after a scheduled delay time (or triggered by a loss of FFRW sensing as described above in conjunction with FIG. 8).

At block 718, control circuit 206 may determine if AV block response criteria are met after making an AV block detection at block 716. In some examples, control circuit 206 may generate an output by storing data in memory 210, which may be transmitted to external device 20, used for transmitting a notification of AV block detection, and/or providing a therapy response at block 720 according to any of the examples give described herein when a single AV block detection is made. In other examples, at least two or more AV block detections corresponding to two or more detection time intervals may be required, consecutively or non-consecutively, in order to meet AV block response criteria at block 718 before control circuit 206 generates an output at block 720, which may include storing data, transmitting an AV block notification, adjusting sensing control parameters, adjusting a therapy control parameter or providing a therapy response.

Figure 16:
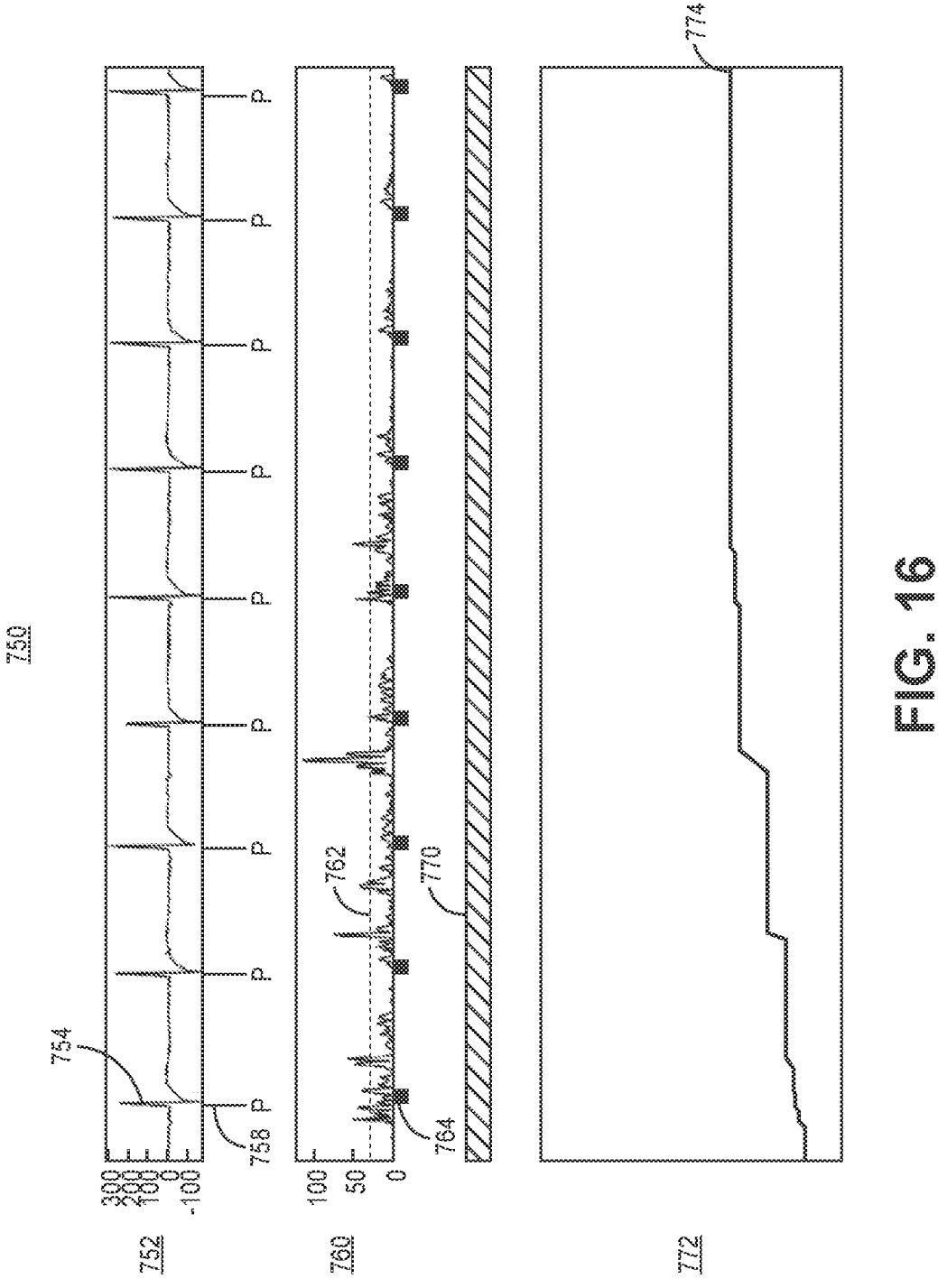
FIG. 16 is a diagram of a cardiac electrical signal and motion signal spanning a detection time interval according to one example.

FIG. 16 is a diagram 750 of a cardiac electrical signal 752 and motion signal 760 spanning a detection time interval 770 according to one example. P-waves 754 of cardiac electrical signal 752 are sensed by sensing circuit 204, which generates the P-wave sensed event signals 758. Control circuit 206 may count P-waves sensed by sensing circuit 204, e.g., by counting the P-wave sensed event signals 758 (and atrial pacing pulses if present) that occur over detection time interval 770. In this example, eight P-waves are sensed and detection time interval 770 may be about eight seconds long.

During the detection time interval 770, control circuit 206 determines a ventricular event metric by determining an integration metric 772. In the example shown, detection time interval 770 includes a single integration interval over which the integration metric 772 is determined. control circuit 206 may sum the sample points of motion signal 760 that are greater than a predetermined threshold amplitude 762. Threshold amplitude 762 is shown set to about 25 ADC units, however higher or lower thresholds may be used. Threshold amplitude 762 is not necessarily set to discriminate ventricular event signals from other motion signals but may be set to reduce the contribution of motion signals associated with atrial systole or other non-ventricular motion signals or baseline noise that may be present in motion signal 760. In some examples, control circuit 206 may set an atrial blanking period 764 following each atrial event. Control circuit 206 may ignore motion signal sample points during the atrial blanking periods 764 for the purposes of determining the integration metric 772. In some cases, both a threshold amplitude 762 and the atrial blanking period 764 are applied to the motion signal 760 by control circuit 206 such that only motion signal sample points having an amplitude greater than threshold 762 that are outside atrial blanking periods 764 are used, e.g., counted or summed, for determining the integration metric 772. In other examples, neither the threshold 762 nor the atrial blanking periods 764 are applied. Control circuit 206 may sum the rectified amplitudes of all sample points of the filtered motion signal 760 during the detection time interval 770 to determine the integration metric.

The integration metric may be determined by control circuit 206 as the value 774 at the expiration of the detection time interval 770. As described above, control circuit 206 may normalize the integration metric value 774 reached at the end of the detection time interval 770 by the number of atrial events counted during the detection time interval 770. The normalized integration metric represents a measure of the number or summation of motion signal sample points per atrial cycle. During 1:1 AV conduction, the normalized integration metric can be expected to be greater than a specified threshold value, indicating the presence of the relatively large ventricular event signal during each atrial cycle that occurs during detection time interval 770. When AV block is present, as in the case of the example of FIG. 16, a large ventricular event signal is not present following each P-wave sensed event signal 758, resulting in a relatively small integration metric 774 at the expiration of the detection time interval 770. Control circuit 206 may detect AV block by determining that the integration metric value 774, which may be normalized by the number of atrial events or cycles during detection time interval 770, is less than a ventricular event threshold value, indicating there are no or fewer than expected ventricular events during the detection time interval 770. The threshold value applied to the integration metric may be established by control circuit 206 during confirmed AV conduction as described above. For example, control circuit 206 may determine the normalized integration metric during known AV conduction and set the threshold value as a percentage of (or offset less than) the normalized integration metric.

Figure 17:
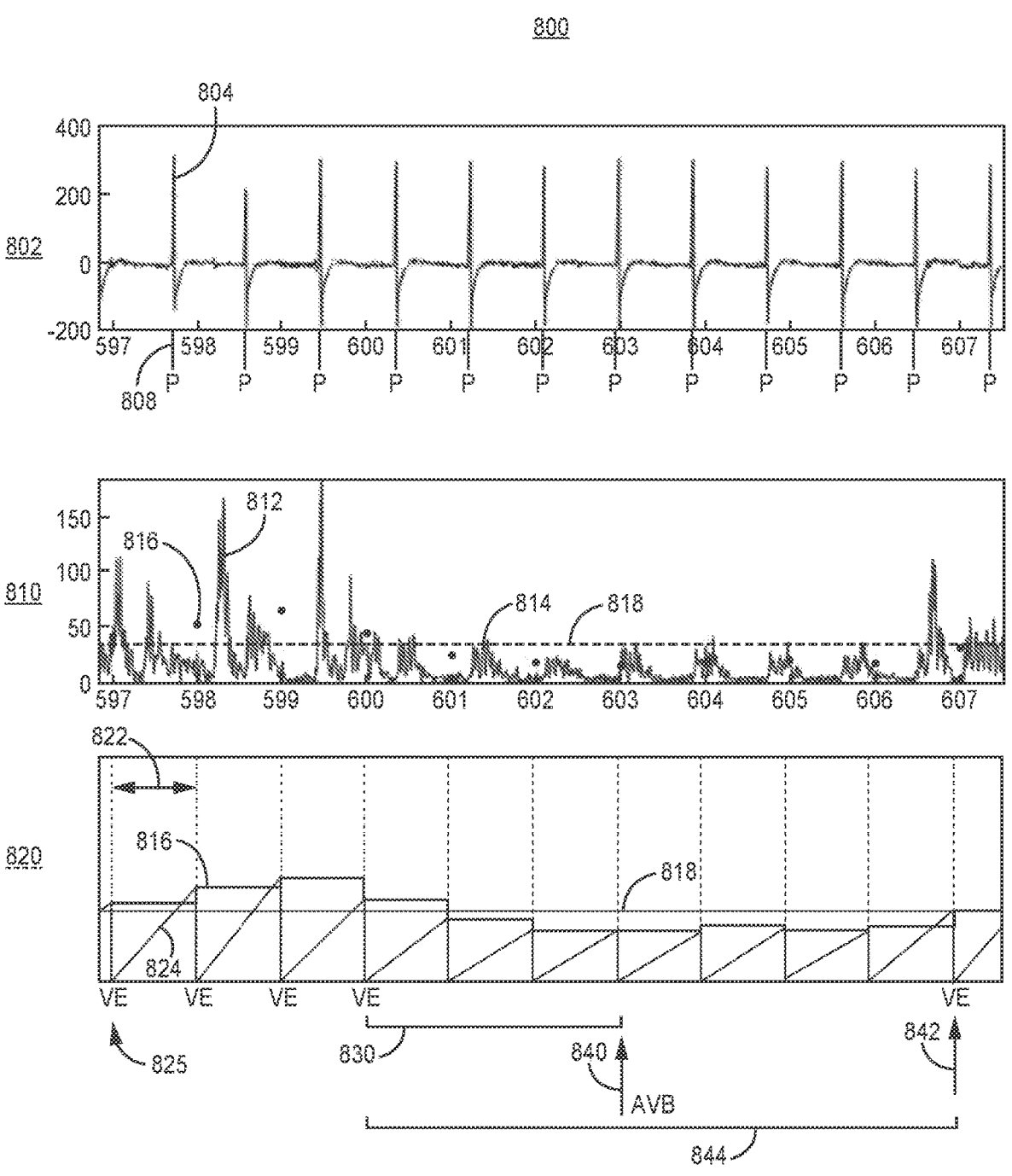
FIG. 17 is a diagram of a cardiac electrical signal and motion signal over multiple integration intervals for determining a ventricular event metric according to one example.

FIG. 17 is a diagram 800 of a cardiac electrical signal 802 and motion signal 810 over multiple integration intervals 822 according to one example. Cardiac electrical signal 802 is an atrial EGM signal including P-waves 804 that are sensed by sensing circuit 204. Sensing circuit 204 generates P-wave signals 808 in response to each sensed P-wave 804.

Motion signal 810 is a filtered, rectified signal that includes multiple atrial event signals 814, each corresponding to an atrial contraction following each P-wave 804. Motion signal 810 includes ventricular event signals 812 when a ventricular contraction occurs. Control circuit 206 may be configured to generate an integration metric signal 820 by determining an integration metric 816 of the motion signal 810 over each integration interval 822 set to a predetermined time interval, e.g., one second, two seconds, three seconds or other predetermined time interval.

The integration metric 816 may be determined by control circuit 206 by summing the sample point amplitudes of the filtered, rectified motion signal 810 during each integration interval 822. In FIG. 17, a solid black dot shown along motion signal 810 corresponds to the current value of the integration metric reached for the preceding integration interval. While not shown in FIG. 17, as described above in conjunction with FIG. 16, control circuit 206 may set an atrial blanking period applied to the motion signal so that sample points during the atrial blanking period, corresponding to atrial event signals 814, are ignored for the purposes of determining the integration metric. Additionally or alternatively, a sample point amplitude threshold may be set by control circuit 206 such that any motion signal sample point having an amplitude less than the sample point amplitude threshold is not used for determining the integration metric 816.

The integration metric signal 820 may be adjusted to the value of the integration metric 816 reached at the expiration of each preceding integration interval 822. In the example shown, the integration interval 822 is one second, though longer or shorter integration intervals may be used. The summation of sample point amplitudes as it is determined by control circuit 206 over the integration interval 822 is represented by the dotted line 824. While the dotted line 824 during each integration interval 822 is shown as a linearly increasing value for the sake of illustration, it is recognized that the value of the summation of sample point amplitudes during each integration interval 822 may increase at varying rates as the amplitude of the motion signal 810 varies. At the expiration of each integration interval 822, the integration metric signal 820 is adjusted to the new integration metric value, e.g., value 816, and held at that value until the expiration of the next integration interval, when the next integration metric value is available. The value of the integration metric may be reset to zero upon expiration of each integration interval 822 to begin summing sample point amplitudes over the next integration interval, as shown by dotted line 824.

At the expiration of the first integration interval 822, the integration metric signal 820 has a value set to the integration metric 816 reached at the end of integration interval 822. It is to be understood that the sample point amplitudes of motion signal 810 may be buffered in memory 210 and summed to obtain the integration metric value at the expiration of the integration interval 822. The integration metric 816 determined for each integration interval is correlated to the area under the filtered, rectified motion signal during the integration interval 822 that has just expired. At the expiration of each integration interval 822, control circuit 206 may compare the integration metric signal 820 (also represented by each solid dot along motion signal 810) to a ventricular event threshold 818. The ventricular event threshold 818 may be a user programmable value or may be established and/or adjustable by control circuit 206. A method for establishing the ventricular event threshold 818 is described below in conjunction with FIG. 18.

When the integration metric signal 820 is adjusted to a value greater than the ventricular event threshold 818 at the expiration of an integration interval 822, control circuit 206 detects evidence of the ventricular event signal 812 occurring during the integration interval 822. Control circuit 206 may generate a ventricular event (VE) signal 825 at the expiration of each integration interval 822 when the integration metric signal 820 is greater than the ventricular event threshold 818. When the integration metric signal 820, defined as the value of the integration metric at the expiration of each integration interval 822, is less than the ventricular event threshold 818, the control circuit 206 does not generate a VE signal. In some examples, control circuit 206 may generate a marker or signal indicating no VE signal during the integration interval.

In this example, the ventricular event metric determined by control circuit 206 for detecting AV block may be the number of integration intervals 822 during the detection time interval 830 that expire with no ventricular event detection (each integration metric less than the ventricular event threshold 818). The AV block criteria may require that a threshold number of integration intervals 822 expire with no ventricular event detection during the detection interval 830. The detection interval 830 may include a specified number of integration intervals 822 and extends over multiple atrial cycles. Each individual integration interval 822 may or may not extend over multiple atrial cycles. In the example shown, the detection interval 830 is three seconds long and includes three consecutive integration intervals 822. The duration of the detection interval 830 may be adjusted by control circuit 206 based on the atrial rate, the time of day, patient physical activity metric, patient posture, or other conditions. For example, if the time of day is nighttime, the detection interval 830 may be set longer than when the time of day is daytime. In an illustrative example, the detection interval 830 is set to six seconds at night and three seconds during the day.

In some examples, the detection interval 830 is restarted each time a ventricular event is detected based on the integration metric reaching the ventricular event threshold 818. For example, control circuit 206 may restart the detection time interval 830 each time a VE signal 825 is generated by control circuit 206. In this case, the AV block criteria may require that none of the consecutive integration intervals 822 defining the detection time interval 830 are associated with ventricular event detection based on the integration metric being greater than the threshold 818. In other examples, the AV block criteria may require that a threshold number of consecutive or non-consecutive integration intervals 822 are not associated with a ventricular event detection within the detection time interval 830.

In other examples, the detection interval 830 is a moving interval that includes a predetermined number of the most recent integration intervals 822. Control circuit 206 may determine if a threshold number of integration intervals 822 with no ventricular event detection is reached the during the moving detection time interval 830. The integration intervals 822 with no ventricular event detection may or may not be required to be consecutive. In some examples, control circuit 206 may increase a counter for each integration interval 822 that expires without generating a VE signal 825, e.g., without the integration metric reaching the ventricular event threshold 818, and the counter value may be compared to a threshold count at the expiration of the detection time interval 830.

Control circuit 206 detects AV block in response to AV block criteria being met as indicated by arrow 840, based on the detection time interval 830 expiring with a threshold number of integration intervals 822 (three in this example) not associated with a ventricular event detection. In the example shown, three consecutive integration metrics do not reach the ventricular event threshold 818 resulting in AV block detection 840 at the expiration of the detection time interval 830. In response to the AV block detection 840, control circuit 206 may start an AV block episode timer to determine the duration of the AV block episode.

Control circuit 206 continues to determine the integration metric over each subsequent integration interval 822. In response to a ventricular event detection, control circuit 206 may detect termination of the AV block episode as indicated by arrow 842. Control circuit 206 may sum the integration intervals from the start of the detection interval 830 that resulted in AV block detection 840 until AV block termination 842 is detected. In the example shown, when each integration interval is one second, the duration 844 of the AV block episode is seven seconds. The AV block detection 840 may also be referred to as a "ventricular pause" detection since a long pause without a detected ventricular event based on the motion signal 810 sensed over multiple cardiac cycles is detected. As described above, control circuit 206 may detect a threshold number of AV block episodes or long ventricular pauses based on the AV block criteria before generation an output or response to the AV block detection. For example, a threshold duration of the AV block episode, a threshold frequency of AV block detections within one hour, one day, one week or other specified monitoring period, a threshold cumulative duration of detected AV block episodes or other criteria may be required to be met before control circuit 206 generates an output or response to the AV block detection.

Figure 18:
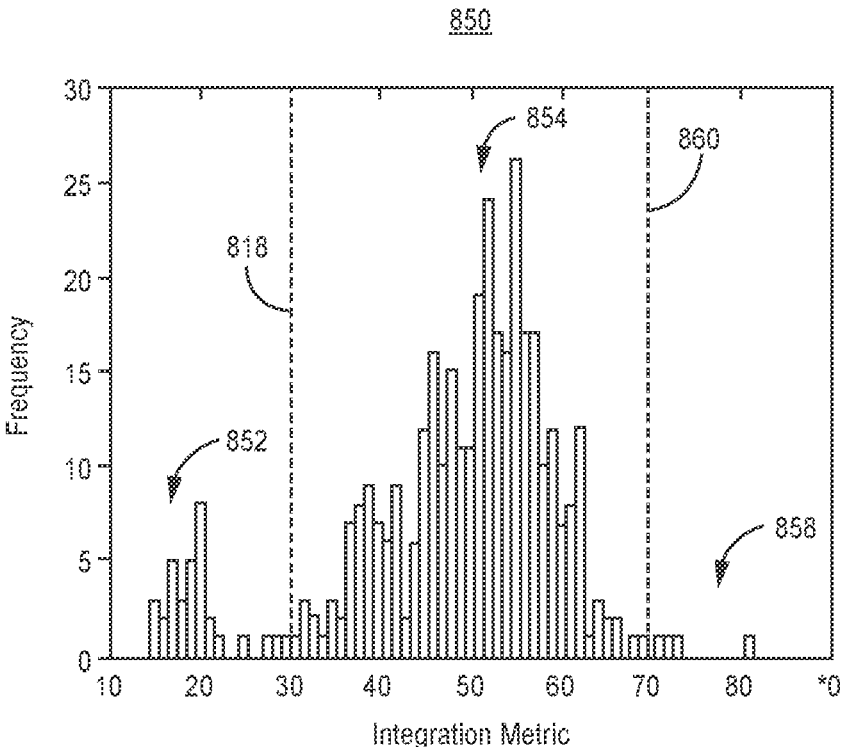
FIG. 18 is a histogram of integration metrics, each determined over an integration interval, e.g., as described in conjunction with FIG. 16 or 17.

FIG. 18 is a histogram 850 of integration metrics, each determined over an integration interval, e.g., as described in conjunction with FIG. 16 or 17. Control circuit 206 may establish the ventricular event threshold 818 by determining the integration metric for multiple integration intervals over a set up time period which may be minutes, hours, days or weeks long. In some examples, a minimum number of integration metrics, e.g., 30, 60, 100, 200, 500 or other selected number of integration metrics may be obtained for generating a histogram of the frequency of the integration metric values.

The ventricular event threshold 818 applied to integration metrics during AV block monitoring may be set based on a mean, median, minimum or specified percentile of the integration metric values. In one example, the ventricular event threshold 818 may be set by control circuit 206 to the fifth percentile integration metric value, the tenth percentile or other selected percentile of the integration metrics. In other examples, the ventricular event threshold 818 may be set by control circuit 206 to the minimum integration metric or a portion, e.g., 80% or 90%, of the minimum integration metric when all integration metrics plotted in the histogram are highly likely to represent intact AV conduction, such as early after pacemaker implant.

In the example shown, relatively low integration metric values 852 occurring at relatively low frequencies may correspond to true ventricular pauses that may be associated with AV block. Relatively higher integration metric values 854 occurring at the highest frequencies likely correspond to intact AV conduction. Very high integration metric values 858 may be considered outliers and may represent noise contaminated integration intervals. In some examples, the ventricular event threshold 818 may be set based on a percentile of the integration metrics determined by control circuit 206 after discarding outliers 858 that are greater than an upper limit 860. Once the ventricular event threshold is established by control circuit 206, control circuit 206 may compare integration metrics to the ventricular event threshold 818 for identifying detection intervals determined to be AV block. When a threshold number of integration metrics fall below the ventricular event threshold 818 during a detection interval, AV block may be detected for the detection interval as described above in conjunction with FIGS. 16 and 17.

In some examples, control circuit 206 may store a frequency or count of integration metric values, each determined over an integration interval, in memory 210. The histogram, such as the histogram represented in FIG. 18, may store each integration metric over a predetermined time period, e.g., over 24 hours, one week, one month or other selected time period. The histogram data stored in memory 210 may be transmitted to external device 20 for generation of a visual, graphical representation of the histogram, e.g., on display unit 54. As described above in conjunction with FIG. 15, when AV block criteria are met, e.g., when at least one (or other threshold number of) integration metric(s) is/are less than a threshold value for detecting normal ventricular activity or motion, control circuit 206 may store an episode of the atrial EGM signal and/or the motion sensor signal.

In an illustrative example, each integration metric represented in histogram 850 may be determined by control circuit 206 over an eight second integration interval (e.g., as shown and described above in conjunction with FIG. 16).

Each eight-second integration interval may be sequential (when the preceding integration interval ends the next integration interval starts) or overlapping. For instance, an eight second integration interval may start every one second or every two seconds such that the eight second integration intervals are overlapping in some examples. When a threshold number of consecutive integration intervals are less than the ventricular event threshold value, control circuit 206 may store a six second (or other duration) segment of the atrial EGM and/or the motion sensor signal in memory 210. The signal segments stored in memory 210 may be transmitted to external device 20 for display by display unit 54 and may be displayed with the histogram data accumulated in memory 210 corresponding to a time period, e.g., a 24 hour time period, encompassing the time of the stored signal segments.

Figure 19:
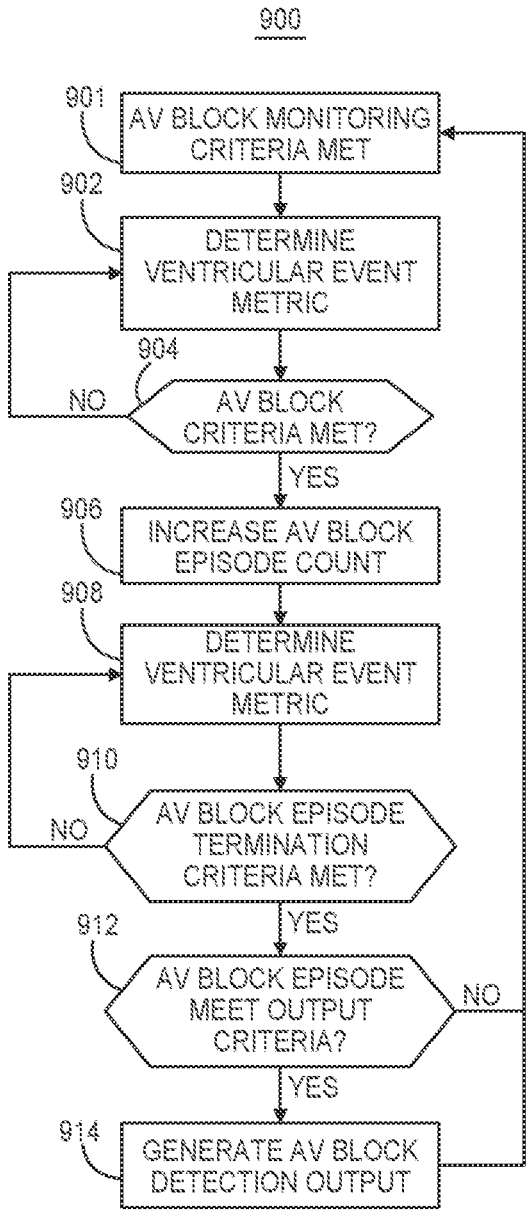
FIG. 19 is a flow chart of a method for determining AV block and generating an output by a medical device according to another example.

FIG. 19 is a flow chart 900 of a method for detecting AV block and generating an AV block detection output by a medical device according to another example. At block 901, control circuit 206 determines that AV block monitoring criteria are met. Control circuit 206 may enable determination of the ventricular event metric over a plurality of atrial cycles at block 902 in response to determining that at least one monitoring condition is satisfied. For example, control circuit 206 may determine the time of day based on a clock included in control circuit 206, determine patient posture based on a signal from the motion sensor 212, determine the atrial rate based on identified atrial events, and/or determine a patient physical activity metric from a signal from motion sensor 212.

AV block monitoring may be suspended during nighttime hours in some instances because AV block during sleep may be clinically less significant than AV block that occurs when the patient is awake. In addition or instead of determining time of day, AV block monitoring may be suspended or disabled when the patient posture is determined to be a horizontal or non-upright posture (e.g., laying or reclined and not sitting or standing). In some examples, the patient physical activity metric or associated SIR may be required to be less than a threshold level (e.g., corresponding to rest or activities of daily living) to avoid oversensing of ventricular events due to motion signal noise caused by patient physical activity. Additionally or alternatively, the control circuit 206 may determine that the AV block monitoring criteria are met at block 901 when the atrial rate is less than a threshold rate, e.g., less than 100 beats per minute. Example AV block monitoring criteria may require that the time of day be specified daytime hours, patient posture is upright or non-horizontal, patient physical activity or the associated SIR is less than a threshold level, and/or the atrial rate is less than a threshold rate or any combination thereof.

In some examples, control circuit 206 may perform a check at block 901 to confirm that undersensing of ventricular event signals is not suspected before enabling AV block monitoring. For example, control circuit 206 may determine that ventricular event signals are detected at a threshold frequency before enabling AV block monitoring. When ventricular event signals are not being detected or detected only occasionally, the selected accelerometer axis signal or combination of signals and/or thresholds or criteria for detecting ventricular event signals may not be optimal and may lead to overdetection of AV block.

Verifying that ventricular event signals are detected at least a threshold frequency may include detecting ventricular event threshold amplitude crossings, performing a morphology analysis of the motion signal over a time interval associated with a threshold amplitude crossing, determining an integration metric of the motion signal over predetermined time intervals or number of atrial cycles, or other analysis to verify the presence of the ventricular event signals for promoting reliable AV block detection. The amplitude crossings, ventricular event morphology analysis, integration metric determination and/or other analysis may occur at any time during an atrial cycle over one atrial cycle, or over multiple atrial cycles. The criteria for determining a minimum frequency of ventricular event signals or the presence of at least one ventricular event signal may be set according to the ventricular event metrics being determined. In some examples, the criteria for determining if ventricular event signals are occurring may correspond to a minimum frequency of ventricular event signals at an expected ventricular escape rate or junctional rate, e.g., a rate of at least 20 to 40 ventricular events per minute. When evidence of reliable sensing of ventricular event signals is detected, control circuit 206 may determine that AV block monitoring conditions are met at block 901.

In some examples, the monitoring criteria determined at block 901 by control circuit 206 may be used by control circuit 206 to adjust how the ventricular event metric is determined during AV block monitoring and/or for setting the AV block criteria. For example, AV block monitoring may be enabled when the atrial rate is less than a threshold rate, e.g., less than 100 beats per minute or less than 90 beats per minute. Control circuit 206 may set a ventricular event sensing window and/or ventricular event threshold applied to a given metric, e.g., an integration metric, based on the atrial rate.

In other examples, control circuit 206 may determine the patient posture and/or the time of day. If the time of day is night and/or the patient is in a horizontal posture, control circuit 206 may set a longer detection time interval or higher number of atrial cycles for determining the ventricular event metric than the detection time interval or number of atrial cycles used when the time of day is daytime and the patient posture is upright. Additionally or alternatively, control circuit 206 may set the AV block criteria differently when the time of day is daytime than when the time of day is during the night. The AV block criteria may be set differently when the patient posture is upright than when the patient posture is non-upright. For example, a threshold or other criteria for detecting AV block may be increased or generally made more stringent for detecting AV block at night and/or the patient is in a horizontal position. The AV block criteria may be adjusted to a lower threshold or generally less stringent criteria during the day and/or when the patient is upright so that AV block is more readily detected.

After enabling AV block monitoring at block 901 (and optionally setting any ventricular event detection and/or AV block monitoring control parameters based on conditions checked at block 901), control circuit 206 determines at least one ventricular event metric at block 902 according to any of the examples described herein. Control circuit 206 determines the ventricular event metric based on the motion signal sensed over multiple atrial cycles. As indicated above, the number of atrial cycles over which the ventricular event metric is determined may be adjusted by control circuit 206 by increasing/decreasing a number of identified atrial cycles or increasing/decreasing a detection time interval based on one or more AV block monitoring conditions in some examples.

When control circuit 206 determines that the AV block criteria are met at block 904 based on one or more ventricular event metrics, according to any of the example criteria described herein, control circuit 206 may detect an episode of AV block (which may also be considered a detection of a long ventricular pause). Control circuit 206 may increase an AV block episode count at block 906. Control circuit 206 may continue to determine the ventricular event metric over multiple atrial cycles at block 908 for determining when the ventricular event metric meets AV block episode termination criteria at block 910.

The AV block episode termination criteria may require one or more ventricular event signals to be detected from the motion sensor signal after detecting AV block. For instance, a single ventricular event signal resulting in detection of an AV conduction cycle may satisfy AV block episode (or long ventricular pause) termination criteria. In some examples, different criteria than the criteria applied for detecting AV block may be applied for detecting termination. For example, a lower percentage of AV block cycles out of identified atrial cycles may be required to detect termination than the percentage of AV block cycles required to detect AV block. In other examples, a higher integration metric threshold or smaller variability in the AV activation time may be required to detect termination than the integration metric threshold or AV activation time variability required to detect AV block. In still other examples, termination detection may require a longer detection time interval or a higher number of identified atrial cycles over which the ventricular event metric is determined. Furthermore, control circuit 206 may wait a predetermined time interval after detecting an AV block episode and its termination before detecting another AV block episode to avoid detecting the same AV block episode more than once and/or to avoid detecting multiple AV block episodes due to intermittent ventricular event sensing issues.

When one or more ventricular event metrics meet AV block episode termination criteria at block 910, control circuit 206 may count and log the detected episode and its duration at block 912 in memory 210 for determining if the AV block episode reaches AV block detection output criteria at block 912. For example, the duration of the AV block episode, the count of AV block episode detections, the total cumulative duration of all AV block episodes detected over a specified time period, a trend in the percentage of AV block cycles, a trend in the AV activation time duration and/or variability, or other metrics corresponding to the frequency, duration and/or severity of the AV block episode(s) detected by control circuit 206 may be compared to the output criteria at block 912. If output criteria are unmet, control circuit 206 may return to block 901. If output criteria are met, control circuit 206 responds to the AV block episode detection at block 914 by transmitting a notification, storing cardiac signal episodes, enabling FFRW sensing, adjusting a pacing therapy and/or other response according to any of the examples given herein.

Figure 20:
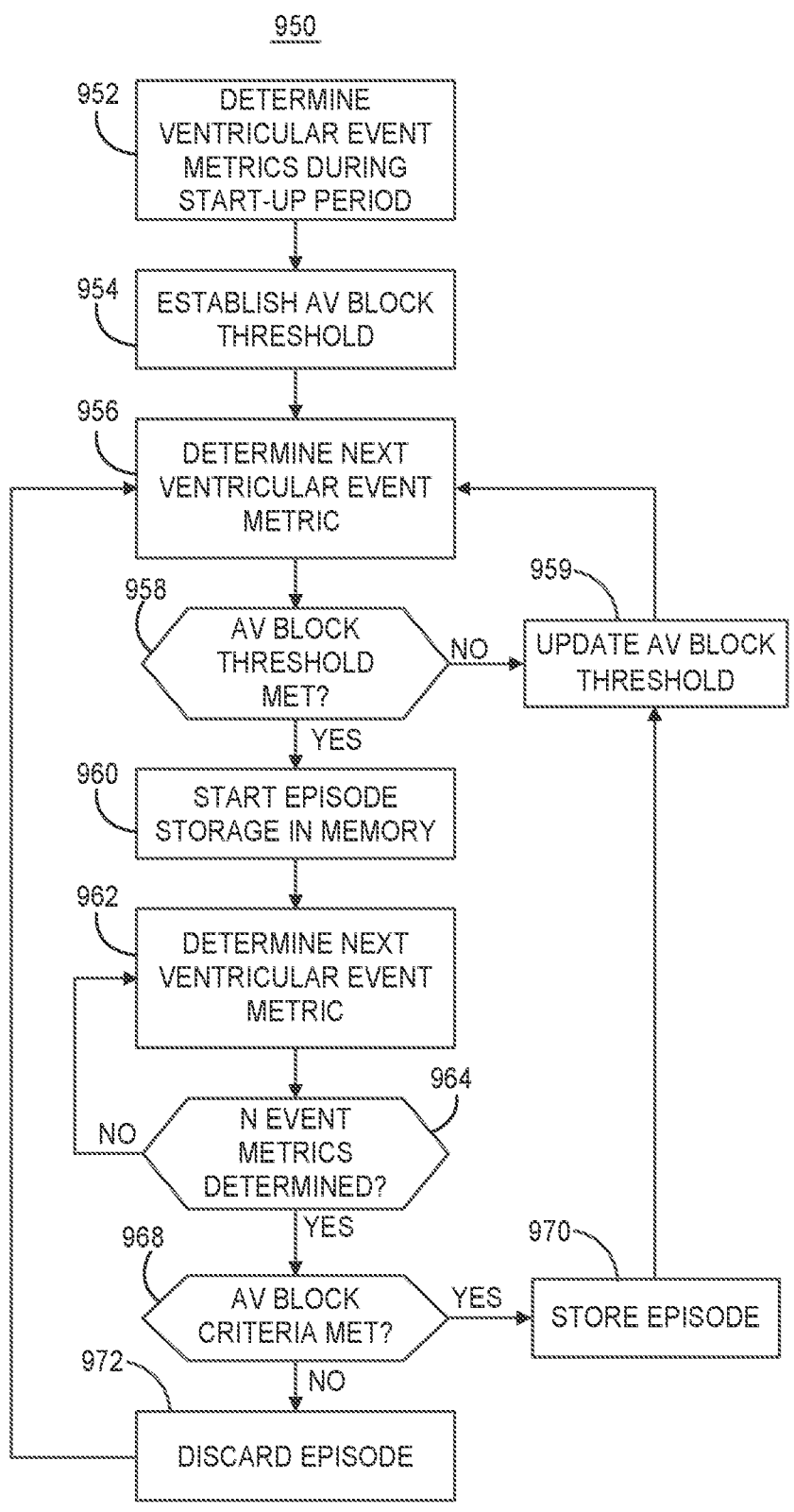
FIG. 20 is a flow chart of a method for determining AV block criteria are met by at least one ventricular event metric and generating an output in response to the AV block criteria being met according to another example.

FIG. 20 is a flow chart 950 of a method for determining AV block criteria are met by at least one ventricular event metric and generating an output in response to the AV block criteria being met according to another example. At block 952, control circuit 206 may determine ventricular event metrics during a start-up period for use in establishing an AV block threshold (or range). The AV block threshold may also be referred to as a "ventricular event threshold" or "ventricular motion threshold" because the threshold is set for discriminating between values of the ventricular event metrics that may correspond to AV block (when no or few ventricular event signals are present in the motion signal) and values of the ventricular event metric that may correspond to AV conduction when ventricular activity and motion are likely to be normal or near normal. For example, control circuit 206 may determine any of the example ventricular event metrics described herein over 1, 4, 8, 12, 24, 48 or 72 hours or other specified start-up period. Control circuit 206 may establish an AV block threshold at block 954 based on the ventricular event metrics determined during the start-up period. For example, during the first 24 hours after enabling the AV block monitoring feature of pacemaker 14, control circuit 206 may accumulate ventricular event metrics and establish an AV block threshold based on the ventricular event metrics, such as based on a mean, median, specified percentile, minimum or maximum value or other representative value of the ventricular event metrics (depending in part on the type of ventricular event metric being determined) that is correlated to a relatively low incidence of ventricular event signals in the motion signal.

At block 956, control circuit 206 may begin AV block monitoring by determining the next ventricular event metric. Control circuit 206 may determine the ventricular event metric over multiple atrial cycles as described in the various examples presented herein. When control circuit 206 determines that the ventricular event metric does not meet the AV block threshold requirement at block 958, control circuit 206 may return to block 956 to determine the next ventricular event metric. Depending on the ventricular event metric being determined and the corresponding AV block threshold, the ventricular event metric may be required to be less than the AV block threshold (e.g., when the ventricular event metric is a detected ventricular event count, integration metric, or AV conduction time). In other examples, the ventricular event metric may be required to be greater than the AV block threshold, e.g., when the ventricular event metric is an AV interval variability or standard deviation.

When the AV block threshold is not met at block 958, control circuit 206 may use the ventricular event metric to update the AV block threshold at block 959 in some examples. In other examples, the AV block threshold established at block 954 is not updated based on ventricular event metrics that do not meet the AV block threshold. In this case, block 959 is skipped. As described below, the AV block threshold may be updated based on ventricular event metrics that are determined to meet AV block criteria, resulting in a generated AV block output by control circuit 206.

When control circuit 206 determines that the ventricular event metric meets the AV block threshold at block 958, control circuit 206 may start storing a cardiac signal episode in memory 210. The motion signal from motion sensor 212 may be stored in memory 210 and/or a cardiac electrical signal received from sensing circuit 204 may be stored in memory 210.

At block 962, control circuit 206 may determine the next ventricular event metric, while the cardiac signal(s) continue to be acquired and written to memory 210. Control circuit 206 may determine a predetermined number of ventricular event metrics, e.g., to span a desired detection time interval, for use in determining when AV block criteria are met based on the ventricular event metrics. For example, control circuit 206 may determine two, three, four, five, six, ten, twelve or other selected number of consecutive ventricular event metrics at block 962. Each ventricular event metric may be determined over multiple atrial cycles. When a desired number of N ventricular event metrics are determined ("yes" branch of block 964), control circuit 206 may determine if the N ventricular event metrics meet AV block criteria at block 968. The N ventricular event metrics may include the first ventricular event metric determined at block 956 that triggered the start of cardiac signal episode storage.

For example, control circuit 206 may determine if the number of individual ventricular event metrics that meet the AV block threshold reaches a threshold number. In other examples, control circuit 206 may determine a mean, median, minimum, maximum, standard deviation, variability or other representative value of the N ventricular event metrics for comparison to a threshold or range in order to determine that AV block criteria are met based on the ventricular event metrics.

When the AV block criteria are not met at block 968, the cardiac signal episode being recorded in memory 210 may be discarded at block 972. Control circuit 206 may return to block 956 to determine the next ventricular event metric. When the N ventricular event metrics meet the AV block criteria as determined at block 968, control circuit 206 generates the AV block output at block 970 by storing the cardiac signal episode in memory 210 as an AV block (or low ventricular motion) episode. Since the N ventricular event metrics satisfied AV block criteria, the N ventricular event metrics (which may include the ventricular event metric that triggered the start of cardiac signal episode storage) may be used by control circuit 206 to update the AV block threshold at block 959 in some examples. Control circuit 206 returns to block 956 to determine the next ventricular event metric.

The AV block episode stored at block 970 may include an episode of the motion signal and/or an episode of the cardiac electrical signal that is recorded during the determination of at least some of the N ventricular event metrics (at block 962), starting from block 960 at the time that the ventricular event metric was determined to meet the AV block threshold (at block 958). In this way, one ventricular event metric determined over multiple atrial cycles may trigger the start of recording a cardiac signal episode in memory 210 when the ventricular event metric meets the established AV block threshold. The cardiac signal episode is recorded in memory as at least one more ventricular event metric is determined. When the at least one additional ventricular event metric meets AV block criteria, the temporarily stored cardiac signal episode may be stored as an AV block episode, e.g., with a date and time stamp and optionally with other ventricular event metric data. Otherwise, the cardiac signal episode may be discarded in response to the AV block criteria not being met by the N ventricular event metrics at block 968. It is to be understood that the AV block episode may or may not be actual AV block but does at least correspond to an episode of time during which ventricular contribution to the motion signal is relatively low or variable, which may be evidence of AV block.

Figure 21:
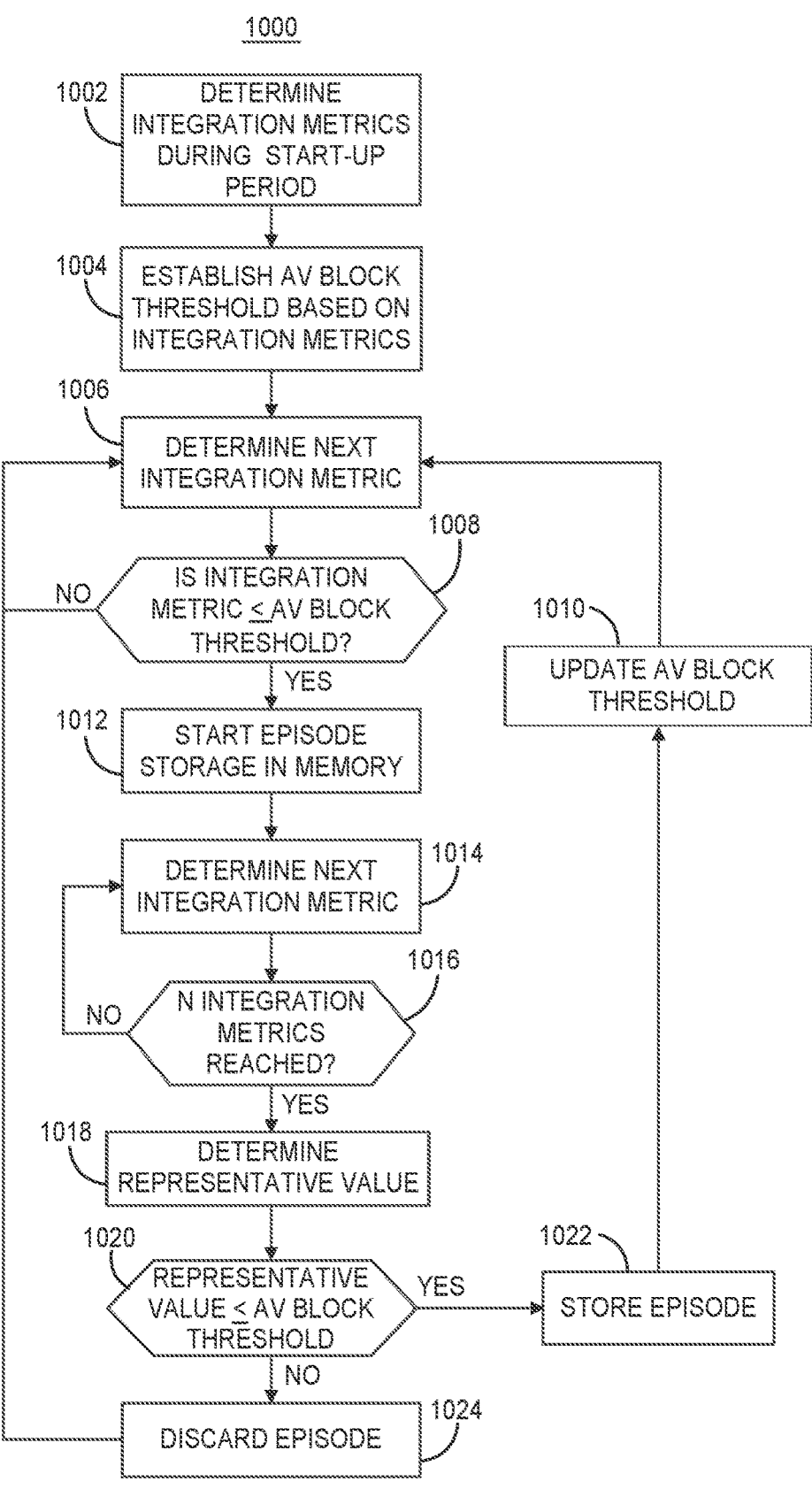
FIG. 21 is a flow chart of a method for determining when AV block criteria are met based on ventricular event metrics determined as integration metrics from the motion signal and generating an AV block output in response to the integration metrics meeting the AV block criteria according to one example.

FIG. 21 is a flow chart 1000 of a method for determining when AV block criteria are met based on ventricular event metrics determined as integration metrics from the motion signal and generating an AV block output in response to the integration metrics meeting the AV block criteria. The method of flow chart 1000 illustrates one example for performing the method generally described above in conjunction with FIG. 20. In this example, one integration metric that is less than an established AV block threshold may trigger cardiac signal episode storage. However, the cardiac signal episode may be discarded when N integration metrics determined over a detection time interval do not meet AV block criteria.

At block 1002, control circuit 206 determines integration metrics from the motion signal during a start-up period, e.g., over an 8, 12, 24, or 48 hour period or other selected time period. The integration metrics may be determined according to any of the examples described above, e.g., in conjunction with FIGS. 15-17. In an illustrative example, control circuit 206 sums the sample points of the filtered, rectified motion signal over a two second integration time interval to obtain one integration metric. The integration metrics may be obtained from each two-second integration time interval over a start-up period of 24 hours, as an example.

At block 1004, control circuit 206 may establish the ventricular event threshold, which in this example may be referred to as the AV block threshold because it distinguishes values of the integration metric expected to correspond to AV conduction and values of the integration metric expected to correspond to AV block, as generally described above in conjunction with FIG. 18. Control circuit 206 may establish the AV block threshold based on the integration metrics determined at block 1002. As described above in conjunction with FIG. 18, a ventricular event threshold (set equal to the AV block threshold in this example) may be established as a percentile of the integration metrics, which may be stored in a histogram in memory 210. In another example, control circuit 206 may determine the AV block threshold at block 1004 by determining a minimum average integration metric from multiple detection time intervals during the start-up period. For example, the detection time interval may be set to 8 seconds such that four 2-second integration metrics may be determined during each detection time interval during the start-up period and during subsequent AV block monitoring. Control circuit 206 may be configured to determine the average 2-second integration metric out of the four 2-second integration metrics determined over each 8 second detection time interval. As described above, the 8-second detection time intervals may be non-overlapping, consecutive time intervals or overlapping consecutive time intervals in various examples. At block 1004, control circuit 206 may determine the average integration metric for each detection time interval (when multiple integration metrics span each detection time interval). The AV block threshold may be based on the average integration metrics. In other examples, the median integration metric, nth smallest integration metric or other representative value of the integration metrics spanning each detection time interval may be determined, and these representative values determined over the start-up period may be used for setting the AV block threshold.

In one example, control circuit 206 may determine the minimum representative value of the values determined over the start-up period at block 1004. Continuing with the example of determining the average integration metric over each detection time interval, control circuit 206 may determine the minimum average integration metric at block 1004 and establish the AV block threshold based on the minimum average integration metric that occurs over the start-up period. For instance, control circuit 206 may establish the AV block threshold at block 1004 by summing together four consecutive 2-second integration metrics and dividing the sum by 4 to determine the average integration metric from each 8 second detection time interval during the start-up period. Control circuit 206 may identify the minimum average integration metric and establish the AV block threshold at block 1004 as the minimum average integration metric. It is to be understood that the example time intervals given in the foregoing example are illustrative in nature and that different time intervals and different combinations of time intervals may be selected as the integration interval, the detection time interval and the start-up period used to establish the AV block threshold.

In other examples, control circuit 80 may establish the AV block threshold at block 1004 as the minimum average integration metric plus an offset or as a percentage of the minimum average integration metric. In still other examples, the AV block threshold may be set as the average integration metric minus an offset or as a percentage of the average integration metric.

After establishing the AV block threshold at block 1004, control circuit 206 starts AV block monitoring by determining the next integration metric at block 1006, e.g., the 2-second integration metric of the motion signal. Control circuit 206 may compare the integration metric to the AV block threshold established at block 1004, e.g., as the minimum average integration metric. When control circuit 206 determines that the current integration metric, e.g., the 2-second integration metric, is greater than the AV block threshold established at block 1004, control circuit 206 returns to block 1006 to determine the next integration metric.

In response to the integration metric being less than or equal to the AV block threshold at block 1008, control circuit 206 starts recording the motion signal from motion sensor 212 and/or the cardiac electrical signal from sensing circuit 204 in memory 210 at block 1012. In some examples, the motion signal used to determine the integration metric at block 1006 may be buffered in memory 210 such that the stored cardiac signal episode may begin at the start of the integration metric that meets the AV block threshold requirement at block 1008. In other examples, the stored cardiac signal episode may begin at the start of the next integration interval in response to the current integration metric being less than or equal to the AV block threshold at block 1008.

At block 1014, control circuit 206 determines the next integration metric. Control circuit 206 may determine if a required number of N integration metrics have been determined at block 1016. In various examples, one, two, three, four or more integration metrics may be required after the first integration metric that meets the AV block threshold to reach N integration metrics required for determining when AV block criteria are met. In an illustrative example, control circuit 206 determines three more 2-second integration metrics after the first integration metric that is less than or equal to the AV block threshold so that four 2-second integration metrics spanning an 8-second detection time interval are determined.

When the required number of integration metrics have been determined over the detection time interval, as determined at block 1016, control circuit 206 may determine the average integration metric out of the N integration metrics at block 1018. In other examples, a different representative value of the N integration metrics may be determined other than the average. For example, a median, minimum, nth smallest or other representative value may be determined from the N integration metrics for use in determining when the N integration metrics meet AV block criteria. Continuing the illustrative example given above, control circuit 80 may sum the four 2-second integration metrics determined (one at block 1006 and three more at block 1014) and divide by four to determine the average integration metric at block 1018. Control circuit 206 may compare this average integration metric to the AV block threshold at block 1020. As described above, the AV block threshold is established at block 1004 as the minimum average integration metric determined from the integration metrics determined during the start-up period. When the average integration metric from the most recent detection time interval is greater than the AV block threshold ("no" branch of block 1020), the cardiac signal episode stored in memory 210 starting at block 1012 is discarded at block 1024. Control circuit 206 returns to block 1006 to determine the next integration metric without determining that AV block criteria are met or generating an AV block output.

When control circuit 206 determines that the average integration metric (or other representative value of the N integration metrics) is less than or equal to the AV block threshold at block 1020, control circuit 206 determines that the AV block criteria are met. In response to the AV block criteria being met, control circuit 206 generates an output at block 1022 by storing the cardiac signal episode in memory 210 as an AV block episode (which may also be referred to as a "low ventricular motion" or more generally "low cardiac motion" episode since true AV block may or may not be actually present). The cardiac signal episode is stored in memory 210, e.g., with a date and time stamp, so that it is available for transmission to external device 20 for review and analysis by a clinician. The cardiac signal episode may be equal to or less than the detection time interval corresponding to the N integration metrics. For instance, when the first integration metric that is less than the AV block threshold triggers the start of episode storage in memory at block 1012, the cardiac signal(s) may be stored over the subsequent three integration intervals for a total of six seconds in the illustrative example of four 2-second integration metrics determined over an 8-second detection time interval.

Control circuit 206 returns to block 1006 to determine the next integration metric to continue monitoring for AV block. In some examples, the average integration metric determined at block 1018, that is less than the AV block threshold at block 1020, may be used to update the AV block threshold at block 1010. For instance, the average integration metric determined at block 1018 that is less than the current value of the AV block threshold may be determined as the new minimum average integration metric and used as the updated AV block threshold at block 1008 after determining the next integration metric. In other examples, the current value of the AV block threshold and the new minimum average integration metric determined at block 1018 (that is less than the current AV block threshold) may be combined, e.g., averaged, to determine the updated AV block threshold at block 1010.

Memory 210 may be configured to store one or more AV block episodes in response to the AV block criteria being met at block 1020. Since the AV block threshold may be updated based on an average integration metric that is less than the current AV block threshold, the cardiac signal episode stored at block 1022 will be the AV block episode associated with the lowest average integration metric. The AV block episode may overwrite the oldest AV block episode stored when memory 210 is configured to store more than one cardiac signal episode.

It should be understood that, depending on the example, certain acts or events of any of the methods described herein can be performed in a different sequence, may be added, merged, or left out altogether (e.g., not all described acts or events are necessary for the practice of the method). Moreover, in certain examples, acts or events may be performed concurrently, e.g., through multi-threaded processing, interrupt processing, or multiple processors, rather than sequentially. In addition, while certain aspects of this disclosure are described as being performed by a single circuit or unit for purposes of clarity, it should be understood that the techniques of this disclosure may be performed by a combination of units or circuits associated with, for example, a medical device.

In one or more examples, the functions described may be implemented in hardware, software, firmware, or any combination thereof. If implemented in software, the functions may be stored as one or more instructions or code on a computer-readable medium and executed by a hardware-based processing unit. Computer-readable media may include computer-readable storage media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPLAs), or other equivalent integrated or discrete logic circuitry. Accordingly, the term "processor," as used herein may refer to any of the foregoing structure or any other structure suitable for implementation of the techniques described herein. Also, the techniques could be fully implemented in one or more circuits or logic elements.

Thus, a medical device has been presented in the foregoing description with reference to specific examples. It is to be understood that various aspects disclosed herein may be combined in different combinations than the specific combinations presented in the accompanying drawings. It is appreciated that various modifications to the referenced examples may be made without departing from the scope of the disclosure and the following claims.

What is claimed is:

1. A medical device comprising:
a motion sensor configured to sense a motion signal;
a control circuit configured to:
for each atrial cycle of a plurality of atrial cycles:
determine a fiducial point of the motion signal;
determine an atrioventricular activation time from an atrial event to the fiducial point of the motion signal;
determine a ventricular event metric based on the atrioventricular activation times determined for the plurality of atrial cycles;
determine that the ventricular event metric meets output criteria; and
generate an output comprising a pacing therapy adjustment in response to determining that the ventricular event metric meets the output criteria;
a memory configured to store the generated output; and
a therapy delivery circuit configured to deliver a pacing therapy according to the pacing therapy adjustment.

2. The medical device of claim 1 wherein the control circuit is further configured to determine the ventricular event metric by determining a trend of the atrioventricular activation time based on the atrioventricular activation times.

3. The medical device of claim 1 wherein the control circuit is further configured to determine the ventricular event metric based on the atrioventricular activation times by determining a variability of the atrioventricular activation times.

4. The medical device of claim 1 wherein the control circuit is further configured to:
compare the atrioventricular activation times to a first threshold activation time;

count each atrioventricular activation time that is greater than the first threshold activation time as an atrioventricular block cycle; and
determine the ventricular event metric as the count of the atrioventricular block cycles.

5. The medical device of claim 4 wherein the control circuit is further configured to:
compare the atrioventricular activation times to a second threshold activation time that is less than the first threshold activation time; and
count each atrioventricular activation time that is less than the second threshold activation time as an atrioventricular block cycle.

6. The medical device of claim 1 wherein the control circuit is further configured to:
determine the ventricular activity metric by:
determining a representative value of the atrioventricular activation times;
determining a range of the atrioventricular activation times; and
determine that the ventricular activity metric meets the output criteria when the representative value is greater than a threshold atrioventricular activation time and the range is greater than a threshold range.

7. The medical device of claim 1 wherein the control circuit is further configured to determine the ventricular activity metric by determining a sum of differences between successive atrioventricular activation times of the determined atrioventricular activation times.

8. The medical device of claim 1 wherein the control circuit is further configured to determine the fiducial point of the motion signal as a maximum peak amplitude of the motion signal sensed during the respective atrial cycle.

9. The medical device of claim 1 wherein the control circuit is further configured to:
detect a condition for monitoring for atrioventricular block; and
determine the ventricular activation times in response to detecting the condition for monitoring for atrioventricular block.

10. The medical device of claim 1 further comprising:
a sensing circuit configured to sense a cardiac electrical signal; and
a telemetry circuit;
wherein the control circuit is further configured to store an episode of at least one of the cardiac electrical signal and the motion signal in response to determining that the ventricular event metric meets the atrioventricular block criteria; and
the telemetry circuit is configured to transmit the stored episode.

11. A method comprising:
sensing a motion signal;
for each atrial cycle of a plurality of atrial cycles:
determining a fiducial point of the motion signal;
determining an atrioventricular activation time from an atrial event to the fiducial point of the motion signal;
determining a ventricular event metric based on the atrioventricular activation times determined for the plurality of atrial cycles;
determining that the ventricular event metric meets output criteria;
generating an output comprising a pacing therapy adjustment in response to determining that the ventricular event metric meets the output criteria;
storing the generated output in a memory; and delivering a pacing therapy according to the pacing therapy adjustment.

12. The method of claim 11 further comprising determining the ventricular event metric by determining a trend of the atrioventricular activation time based on the atrioventricular activation times.

13. The method of claim 11 further comprising determining the ventricular event metric based on the atrioventricular activation times by determining a variability of the atrioventricular activation times.

14. The method of claim 11 further comprising:

comparing the atrioventricular activation times to a first threshold activation time;

counting each atrioventricular activation time that is greater than the first threshold activation time as an atrioventricular block cycle; and determining the ventricular event metric as the count of the atrioventricular block cycles.

15. The method of claim 14 further comprising:

comparing the atrioventricular activation times to a second threshold activation time that is less than the first threshold activation time; and counting each atrioventricular activation time that is less than the second threshold activation time as an atrioventricular block cycle.

16. The method of claim 11 further comprising:

determining the ventricular activity metric by:

determining a representative value of the atrioventricular activation times;

determining a range of the atrioventricular activation times; and determining that the ventricular activity metric meets the output criteria when the representative value is greater than a threshold atrioventricular activation time and the range is greater than a threshold range.

17. The method of claim 11 further comprising determining the ventricular activity metric by determining a sum of differences between successive atrioventricular activation times of the determined atrioventricular activation times.

18. The method of claim 11 further comprising determining the fiducial point of the motion signal as a maximum peak amplitude of the motion signal sensed during the respective atrial cycle.

19. The method of claim 11 further comprising:

detecting a condition for monitoring for atrioventricular block; and determining the ventricular activation times in response to detecting the condition for monitoring for atrioventricular block.

20. The method of claim 11 further comprising:

sensing a cardiac electrical signal;

storing an episode of at least one of the cardiac electrical signal and the motion signal in response to determining that the ventricular event metric meets the atrioventricular block criteria; and transmitting the stored episode.

* * * * *